(12) United States Patent
Cheng et al.

(10) Patent No.: US 12,185,982 B2
(45) Date of Patent: Jan. 7, 2025

(54) EXTERNAL ADJUSTMENT DEVICE FOR DISTRACTION DEVICE

(71) Applicant: NuVasive Specialized Orthopedics, Inc., San Diego, CA (US)

(72) Inventors: Shanbao Cheng, San Diego, CA (US); Michael Moeller, San Diego, CA (US); Jeffrey Schwardt, San Diego, CA (US)

(73) Assignee: Globus Medical Inc., Audubon, PA (US)

( * ) Notice: Subject to any disclaimer, the term of this patent is extended or adjusted under 35 U.S.C. 154(b) by 29 days.

(21) Appl. No.: 18/047,449

(22) Filed: Oct. 18, 2022

(65) Prior Publication Data
US 2023/0059518 A1    Feb. 23, 2023

Related U.S. Application Data

(63) Continuation of application No. 17/066,338, filed on Oct. 8, 2020, now Pat. No. 11,504,162, which is a
(Continued)

(51) Int. Cl.
  *A61B 17/70*   (2006.01)
  *A61B 17/72*   (2006.01)
  (Continued)

(52) U.S. Cl.
  CPC .......... *A61B 17/7016* (2013.01); *A61B 17/70* (2013.01); *A61B 17/7216* (2013.01);
  (Continued)

(58) Field of Classification Search
  CPC ............ A61B 17/7016; A61B 17/7216; A61B 2090/0811; A61B 18/04; A61B 90/98;
  (Continued)

(56) References Cited

U.S. PATENT DOCUMENTS 2,702,031 A    2/1955   Leslie
3,111,945 A   11/1963   Von
(Continued)

FOREIGN PATENT DOCUMENTS

CN       1697630 A    11/2005
CN     101040807 A     9/2007
(Continued)

OTHER PUBLICATIONS

Abe et al., "Experimental external fixation combined with percutaneous discectomy in the management of scoliosis.", SPINE, 1999, pp. 646-653, 24, No. 7.
(Continued)

*Primary Examiner* — Danny Nguyen

(57) ABSTRACT

An external adjustment device includes at least one permanent magnet configured for rotation about an axis with a first handle extending linearly at a first end of the device and a second handle at a second end of the device, the second handle extending in a direction substantially off axis to the first handle. The external adjustment device further includes a motor mounted inside the first handle and a first button located in the proximity to one of the first handle or the second handle, the first button configured to be operated by the thumb of a hand that grips the one of the first handle or second handle. The first button is configured to actuate the motor causing the at least one permanent magnet to rotate about the axis in a first direction.

13 Claims, 37 Drawing Sheets

Related U.S. Application Data continuation of application No. 16/004,099, filed on Jun. 8, 2018, now Pat. No. 10,835,290, which is a continuation of application No. PCT/US2016/066179, filed on Dec. 12, 2016.

(60) Provisional application No. 62/276,196, filed on Jan. 7, 2016, provisional application No. 62/265,430, filed on Dec. 10, 2015.

(51) Int. Cl.
*H01F 7/02* (2006.01)
*H01F 7/06* (2006.01)
*A61B 17/00* (2006.01)
*A61B 90/00* (2016.01)
*A61B 90/92* (2016.01)
*A61B 90/98* (2016.01)

(52) U.S. Cl.
CPC ........... *H01F 7/0205* (2013.01); *H01F 7/064* (2013.01); *A61B 2017/00039* (2013.01); *A61B 2017/00057* (2013.01); *A61B 2017/00199* (2013.01); *A61B 2017/00393* (2013.01); *A61B 2017/00398* (2013.01); *A61B 90/08* (2016.02); *A61B 2090/0811* (2016.02); *A61B 90/92* (2016.02); *A61B 90/98* (2016.02)

(58) Field of Classification Search
CPC ........ H01F 7/064; H01F 7/0205; A61F 5/028; G05B 15/02; A61N 2/00
USPC .................................................. 361/143, 147
See application file for complete search history.

(56) References Cited

U.S. PATENT DOCUMENTS

| | | |
|---|---|---|
| 3,372,476 A | 3/1968 | Richard |
| 3,377,576 A | 4/1968 | Edwin |
| 3,512,901 A | 5/1970 | Law |
| 3,597,781 A | 8/1971 | Eibes |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,204,541 A | 5/1980 | Kapitanov |
| 4,357,946 A | 11/1982 | Dutcher et al. |
| 4,386,603 A | 6/1983 | Mayfield |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,700,091 A | 10/1987 | Wuthrich |
| 4,747,832 A | 5/1988 | Buffet |
| 4,854,304 A | 8/1989 | Zielke |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,064,004 A | 11/1991 | Lundell |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,156,605 A | 10/1992 | Pursley et al. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,364,396 A | 11/1994 | Robinson et al. |
| 5,403,322 A | 4/1995 | Herzenberg et al. |
| 5,429,638 A | 7/1995 | Muschler et al. |
| 5,437,266 A | 8/1995 | McPherson et al. |
| 5,466,261 A | 11/1995 | Richelsoph |
| 5,468,030 A | 11/1995 | Walling |
| 5,480,437 A | 1/1996 | Draenert |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,549,610 A | 8/1996 | Russell et al. |
| 5,573,012 A | 11/1996 | McEwan |
| 5,575,790 A | 11/1996 | Chen et al. |
| 5,582,616 A | 12/1996 | Bolduc et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,700,263 A | 12/1997 | Schendel |
| 5,704,938 A | 1/1998 | Staehlin et al. |
| 5,704,939 A | 1/1998 | Justin |
| 5,720,746 A | 2/1998 | Soubeiran |
| 5,743,910 A | 4/1998 | Bays et al. |
| 5,762,599 A | 6/1998 | Sohn |
| 5,771,903 A | 6/1998 | Jakobsson |
| 5,810,815 A | 9/1998 | Morales |
| 5,827,286 A | 10/1998 | Incavo et al. |
| 5,830,221 A | 11/1998 | Stein et al. |
| 5,879,375 A | 3/1999 | Larson, Jr. et al. |
| 5,902,304 A | 5/1999 | Walker et al. |
| 5,935,127 A | 8/1999 | Border |
| 5,945,762 A | 8/1999 | Chen et al. |
| 5,961,553 A | 10/1999 | Coty et al. |
| 5,976,138 A | 11/1999 | Baumgart et al. |
| 5,979,456 A | 11/1999 | Magovern |
| 6,022,349 A | 2/2000 | McLeod et al. |
| 6,033,412 A | 3/2000 | Losken et al. |
| 6,034,296 A | 3/2000 | Elvin et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,234,956 B1 | 5/2001 | He et al. |
| 6,241,730 B1 | 6/2001 | Alby |
| 6,245,075 B1 | 6/2001 | Betz et al. |
| 6,315,784 B1 | 11/2001 | Djurovic |
| 6,319,255 B1 | 11/2001 | Grundei et al. |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,389,187 B1 | 5/2002 | Greenaway et al. |

(56) References Cited

U.S. PATENT DOCUMENTS

| | | |
|---|---|---|
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,499,907 B1 | 12/2002 | Baur |
| 6,500,110 B1 | 12/2002 | Davey et al. |
| 6,508,820 B2 | 1/2003 | Bales |
| 6,510,345 B1 | 1/2003 | Van Bentem |
| 6,537,196 B1 | 3/2003 | Creighton, IV et al. |
| 6,554,831 B1 | 4/2003 | Rivard et al. |
| 6,565,573 B1 | 5/2003 | Ferrante et al. |
| 6,565,576 B1 | 5/2003 | Stauch et al. |
| 6,582,313 B2 | 6/2003 | Perrow |
| 6,583,630 B2 | 6/2003 | Mendes et al. |
| 6,616,669 B2 | 9/2003 | Ogilvie et al. |
| 6,626,917 B1 | 9/2003 | Craig |
| 6,656,135 B2 | 12/2003 | Zogbi et al. |
| 6,656,194 B1 | 12/2003 | Gannoe et al. |
| 6,667,725 B1 | 12/2003 | Simons et al. |
| 6,673,079 B1 | 1/2004 | Kane |
| 6,702,816 B2 | 3/2004 | Buhler |
| 6,706,042 B2 | 3/2004 | Taylor |
| 6,709,293 B2 | 3/2004 | Mori et al. |
| 6,730,087 B1 | 5/2004 | Butsch |
| 6,761,503 B2 | 7/2004 | Breese |
| 6,769,499 B2 | 8/2004 | Cargill et al. |
| 6,789,442 B2 | 9/2004 | Forch |
| 6,796,984 B2 | 9/2004 | Soubeiran |
| 6,802,844 B2 | 10/2004 | Ferree |
| 6,809,434 B1 | 10/2004 | Duncan et al. |
| 6,835,207 B2 | 12/2004 | Zacouto et al. |
| 6,852,113 B2 | 2/2005 | Nathanson et al. |
| 6,918,838 B2 | 7/2005 | Schwarzler et al. |
| 6,918,910 B2 | 7/2005 | Smith et al. |
| 6,921,400 B2 | 7/2005 | Sohngen |
| 6,923,951 B2 | 8/2005 | Contag et al. |
| 6,971,143 B2 | 12/2005 | Domroese |
| 7,001,346 B2 | 2/2006 | White |
| 7,008,425 B2 | 3/2006 | Phillips |
| 7,011,658 B2 | 3/2006 | Young |
| 7,029,472 B1 | 4/2006 | Fortin |
| 7,029,475 B2 | 4/2006 | Panjabi |
| 7,041,105 B2 | 5/2006 | Michelson |
| 7,060,080 B2 | 6/2006 | Bachmann |
| 7,063,706 B2 | 6/2006 | Wittenstein |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,135,022 B2 | 11/2006 | Kosashvili et al. |
| 7,160,312 B2 | 1/2007 | Saadat |
| 7,163,538 B2 | 1/2007 | Altarac et al. |
| 7,189,005 B2 | 3/2007 | Ward |
| 7,191,007 B2 | 3/2007 | Desai et al. |
| 7,218,232 B2 | 5/2007 | DiSilvestro et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,282,023 B2 | 10/2007 | Frering |
| 7,285,087 B2 | 10/2007 | Moaddeb et al. |
| 7,302,015 B2 | 11/2007 | Kim et al. |
| 7,302,858 B2 | 12/2007 | Walsh et al. |
| 7,314,443 B2 | 1/2008 | Jordan et al. |
| 7,333,013 B2 | 2/2008 | Berger |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,390,007 B2 | 6/2008 | Helms et al. |
| 7,390,294 B2 | 6/2008 | Hassler, Jr. |
| 7,402,134 B2 | 7/2008 | Moaddeb et al. |
| 7,402,176 B2 | 7/2008 | Malek |
| 7,429,259 B2 | 9/2008 | Cadeddu et al. |
| 7,445,010 B2 | 11/2008 | Kugler et al. |
| 7,458,981 B2 | 12/2008 | Fielding et al. |
| 7,485,149 B1 | 2/2009 | White |
| 7,489,495 B2 | 2/2009 | Stevenson |
| 7,530,981 B2 | 5/2009 | Kutsenko |
| 7,531,002 B2 | 5/2009 | Sutton et al. |
| 7,553,298 B2 | 6/2009 | Hunt et al. |
| 7,561,916 B2 | 7/2009 | Hunt et al. |
| 7,611,526 B2 | 11/2009 | Carl et al. |
| 7,618,435 B2 | 11/2009 | Opolski |
| 7,658,754 B2 | 2/2010 | Zhang et al. |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,708,737 B2 | 5/2010 | Kraft et al. |
| 7,708,762 B2 | 5/2010 | McCarthy et al. |
| 7,727,143 B2 | 6/2010 | Birk et al. |
| 7,753,913 B2 | 7/2010 | Szakelyhidi, Jr. et al. |
| 7,753,915 B1 | 7/2010 | Eksler et al. |
| 7,762,998 B2 | 7/2010 | Birk et al. |
| 7,763,080 B2 | 7/2010 | Southworth |
| 7,766,855 B2 | 8/2010 | Miethke |
| 7,775,215 B2 | 8/2010 | Hassler, Jr. et al. |
| 7,776,068 B2 | 8/2010 | Ainsworth et al. |
| 7,776,075 B2 | 8/2010 | Bruneau et al. |
| 7,787,958 B2 | 8/2010 | Stevenson |
| 7,794,476 B2 | 9/2010 | Wisnewski |
| 7,811,328 B2 | 10/2010 | Molz, IV et al. |
| 7,835,779 B2 | 11/2010 | Anderson et al. |
| 7,837,691 B2 | 11/2010 | Cordes et al. |
| 7,862,586 B2 | 1/2011 | Malek |
| 7,867,235 B2 | 1/2011 | Fell et al. |
| 7,875,033 B2 | 1/2011 | Richter et al. |
| 7,901,381 B2 | 3/2011 | Birk et al. |
| 7,909,852 B2 | 3/2011 | Boomer et al. |
| 7,918,844 B2 | 4/2011 | Byrum et al. |
| 7,938,841 B2 | 5/2011 | Sharkawy et al. |
| 7,985,256 B2 | 7/2011 | Grotz et al. |
| 7,988,709 B2 | 8/2011 | Clark et al. |
| 8,002,809 B2 | 8/2011 | Baynham |
| 8,011,308 B2 | 9/2011 | Picchio |
| 8,034,080 B2 | 10/2011 | Malandain et al. |
| 8,043,299 B2 | 10/2011 | Conway |
| 8,043,338 B2 | 10/2011 | Dant |
| 8,057,473 B2 | 11/2011 | Orsak et al. |
| 8,057,513 B2 | 11/2011 | Kohm et al. |
| 8,083,741 B2 | 12/2011 | Morgan et al. |
| 8,092,499 B1 | 1/2012 | Roth |
| 8,095,317 B2 | 1/2012 | Ekseth et al. |
| 8,105,360 B1 | 1/2012 | Connor |
| 8,114,158 B2 | 2/2012 | Carl et al. |
| 8,123,805 B2 | 2/2012 | Makower et al. |
| 8,133,280 B2 | 3/2012 | Voellmicke et al. |
| 8,147,549 B2 | 4/2012 | Metcalf, Jr. et al. |
| 8,162,897 B2 | 4/2012 | Byrum |
| 8,162,979 B2 | 4/2012 | Sachs et al. |
| 8,177,789 B2 | 5/2012 | Magill et al. |
| 8,197,490 B2 | 6/2012 | Pool et al. |
| 8,211,149 B2 | 7/2012 | Justis |
| 8,211,151 B2 | 7/2012 | Schwab et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,331 B2 | 8/2012 | Arnin |
| 8,246,630 B2 | 8/2012 | Manzi et al. |
| 8,252,063 B2 | 8/2012 | Stauch |
| 8,267,969 B2 | 9/2012 | Altarac et al. |
| 8,278,941 B2 | 10/2012 | Kroh et al. |
| 8,282,671 B2 | 10/2012 | Connor |
| 8,323,290 B2 | 12/2012 | Metzger et al. |
| 8,357,182 B2 | 1/2013 | Seme |
| 8,366,628 B2 | 2/2013 | Denker et al. |
| 8,372,078 B2 | 2/2013 | Collazo |
| 8,386,018 B2 | 2/2013 | Stauch et al. |
| 8,394,124 B2 | 3/2013 | Biyani |
| 8,403,958 B2 | 3/2013 | Schwab |
| 8,414,584 B2 | 4/2013 | Brigido |
| 8,419,734 B2 | 4/2013 | Walker ............ A61B 17/88 606/60 |
| 8,425,608 B2 | 4/2013 | Dewey et al. |

(56) References Cited

U.S. PATENT DOCUMENTS

| | | |
|---|---|---|
| 8,435,268 B2 | 5/2013 | Thompson et al. |
| 8,439,926 B2 | 5/2013 | Bojarski et al. |
| 8,444,693 B2 | 5/2013 | Reiley |
| 8,469,908 B2 | 6/2013 | Asfora |
| 8,470,004 B2 | 6/2013 | Reiley |
| 8,486,070 B2 | 7/2013 | Morgan et al. |
| 8,486,076 B2 | 7/2013 | Chavarria et al. |
| 8,486,147 B2 | 7/2013 | De Villiers et al. |
| 8,494,805 B2 | 7/2013 | Roche et al. |
| 8,496,662 B2 | 7/2013 | Novak et al. |
| 8,518,062 B2 | 8/2013 | Cole et al. |
| 8,523,866 B2 | 9/2013 | Sidebotham et al. |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,457 B2 | 10/2013 | Hunziker |
| 8,617,220 B2 | 10/2013 | Skaggs |
| 8,579,979 B2 | 11/2013 | Edie et al. |
| 8,585,595 B2 | 11/2013 | Heilman |
| 8,585,740 B1 | 11/2013 | Ross et al. |
| 8,591,549 B2 | 11/2013 | Lange |
| 8,591,553 B2 | 11/2013 | Eisermann et al. |
| 8,613,758 B2 | 12/2013 | Linares |
| 8,623,036 B2 | 1/2014 | Harrison et al. |
| 8,632,544 B2 | 1/2014 | Haaja et al. |
| 8,632,548 B2 | 1/2014 | Soubeiran |
| 8,632,563 B2 | 1/2014 | Nagase et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,657,856 B2 | 2/2014 | Gephart et al. |
| 8,663,285 B2 | 3/2014 | Dall et al. |
| 8,663,287 B2 | 3/2014 | Butler et al. |
| 8,668,719 B2 | 3/2014 | Alamin et al. |
| 8,709,090 B2 | 4/2014 | Makower et al. |
| 8,758,347 B2 | 6/2014 | Weiner et al. |
| 8,758,355 B2 | 6/2014 | Fisher et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,790,343 B2 | 7/2014 | McClellan et al. |
| 8,790,409 B2 | 7/2014 | Van den Heuvel et al. |
| 8,828,058 B2 | 9/2014 | Elsebaie et al. |
| 8,828,087 B2 | 9/2014 | Stone et al. |
| 8,840,651 B2 | 9/2014 | Reiley |
| 8,870,881 B2 | 10/2014 | Rezach et al. |
| 8,870,959 B2 | 10/2014 | Arnin |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,939,924 B1 | 1/2015 | Paulos |
| 8,945,188 B2 | 2/2015 | Rezach et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,992,527 B2 | 3/2015 | Guichet |
| 9,022,917 B2 | 5/2015 | Kasic et al. |
| 9,044,218 B2 | 6/2015 | Young |
| 9,060,810 B2 | 6/2015 | Kercher et al. |
| 9,078,703 B2 | 7/2015 | Arnin |
| 10,835,290 B2 | 11/2020 | Cheng .............. H01F 7/0205 |
| 2002/0050112 A1 | 5/2002 | Koch et al. |
| 2002/0072758 A1 | 6/2002 | Reo et al. |
| 2002/0164905 A1 | 11/2002 | Bryant |
| 2003/0040671 A1 | 2/2003 | Somogyi et al. |
| 2003/0144669 A1 | 7/2003 | Robinson |
| 2003/0220643 A1 | 11/2003 | Ferree |
| 2003/0220644 A1 | 11/2003 | Thelen et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0055610 A1 | 3/2004 | Forsell |
| 2004/0133219 A1 | 7/2004 | Forsell |
| 2004/0138725 A1 | 7/2004 | Forsell |
| 2004/0193266 A1 | 9/2004 | Meyer |
| 2005/0034705 A1 | 2/2005 | Mcclendon |
| 2005/0049617 A1 | 3/2005 | Chatlynne et al. |
| 2005/0065529 A1 | 3/2005 | Liu et al. |
| 2005/0090823 A1 | 4/2005 | Bartimus |
| 2005/0159754 A1 | 7/2005 | Odrich |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0261779 A1 | 11/2005 | Meyer |
| 2005/0272976 A1 | 12/2005 | Tanaka et al. |
| 2006/0004459 A1 | 1/2006 | Hazebrouck et al. |
| 2006/0009767 A1 | 1/2006 | Kiester |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058792 A1 | 3/2006 | Hynes |
| 2006/0069447 A1 | 3/2006 | DiSilvestro et al. |
| 2006/0074448 A1 | 4/2006 | Harrison et al. |
| 2006/0079897 A1 | 4/2006 | Harrison et al. |
| 2006/0136062 A1 | 6/2006 | DiNello et al. |
| 2006/0142767 A1 | 6/2006 | Green et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0200134 A1 | 9/2006 | Freid et al. |
| 2006/0204156 A1 | 9/2006 | Takehara et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0241767 A1 | 10/2006 | Doty |
| 2006/0249914 A1 | 11/2006 | Dulin |
| 2006/0271107 A1 | 11/2006 | Harrison et al. |
| 2006/0282073 A1 | 12/2006 | Simanovsky |
| 2006/0293683 A1 | 12/2006 | Stauch |
| 2007/0010814 A1 | 1/2007 | Stauch |
| 2007/0010887 A1 | 1/2007 | Williams et al. |
| 2007/0021644 A1 | 1/2007 | Woolson et al. |
| 2007/0031131 A1 | 2/2007 | Griffitts |
| 2007/0038410 A1 | 2/2007 | Tunay |
| 2007/0043376 A1 | 2/2007 | Leatherbury et al. |
| 2007/0050030 A1 | 3/2007 | Kim |
| 2007/0118215 A1 | 5/2007 | Moaddeb |
| 2007/0161984 A1 | 7/2007 | Cresina et al. |
| 2007/0163367 A1 | 7/2007 | Sherman |
| 2007/0173837 A1 | 7/2007 | Chan et al. |
| 2007/0179493 A1 | 8/2007 | Kim |
| 2007/0185374 A1 | 8/2007 | Kick et al. |
| 2007/0233098 A1 | 10/2007 | Mastrorio et al. |
| 2007/0239159 A1 | 10/2007 | Altarac et al. |
| 2007/0239161 A1 | 10/2007 | Giger et al. |
| 2007/0255088 A1 | 11/2007 | Jacobson et al. |
| 2007/0270803 A1 | 11/2007 | Giger et al. |
| 2007/0276368 A1 | 11/2007 | Trieu et al. |
| 2007/0276369 A1 | 11/2007 | Allard et al. |
| 2007/0276373 A1 | 11/2007 | Malandain |
| 2007/0276378 A1 | 11/2007 | Harrison et al. |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0009792 A1 | 1/2008 | Henniges et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0027436 A1 | 1/2008 | Cournoyer et al. |
| 2008/0033431 A1 | 2/2008 | Jung et al. |
| 2008/0033436 A1 | 2/2008 | Song et al. |
| 2008/0051784 A1 | 2/2008 | Gollogly |
| 2008/0082118 A1 | 4/2008 | Edidin et al. |
| 2008/0086128 A1 | 4/2008 | Lewis |
| 2008/0097487 A1 | 4/2008 | Pool et al. |
| 2008/0097496 A1 | 4/2008 | Chang et al. |

(56) References Cited

U.S. PATENT DOCUMENTS

| | | |
|---|---|---|
| 2008/0108995 A1 | 5/2008 | Conway et al. |
| 2008/0154127 A1 | 6/2008 | DiSilvestro et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0177319 A1 | 7/2008 | Schwab |
| 2008/0177326 A1 | 7/2008 | Thompson |
| 2008/0190237 A1 | 8/2008 | Radinger et al. |
| 2008/0228186 A1 | 9/2008 | Gall et al. |
| 2008/0255615 A1 | 10/2008 | Vittur et al. |
| 2008/0272928 A1 | 11/2008 | Shuster |
| 2008/0275557 A1 | 11/2008 | Makower et al. |
| 2009/0030462 A1 | 1/2009 | Buttermann |
| 2009/0076597 A1 | 3/2009 | Dahlgren et al. |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112262 A1* | 4/2009 | Pool ............ A61B 17/68 606/246 |
| 2009/0112263 A1 | 4/2009 | Pool et al. |
| 2009/0163780 A1 | 6/2009 | Tieu |
| 2009/0171356 A1 | 7/2009 | Klett |
| 2009/0192514 A1 | 7/2009 | Feinberg et al. |
| 2009/0198144 A1 | 8/2009 | Phillips et al. |
| 2009/0216113 A1 | 8/2009 | Meier et al. |
| 2009/0231073 A1* | 9/2009 | Horisaka ......... A61B 1/00158 335/209 |
| 2009/0275984 A1 | 11/2009 | Kim et al. |
| 2010/0004654 A1 | 1/2010 | Schmitz et al. |
| 2010/0057127 A1 | 3/2010 | McGuire et al. |
| 2010/0094306 A1 | 4/2010 | Chang et al. |
| 2010/0100185 A1 | 4/2010 | Trieu et al. |
| 2010/0106192 A1 | 4/2010 | Barry |
| 2010/0114322 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0217271 A1 | 8/2010 | Pool et al. |
| 2010/0249782 A1 | 9/2010 | Durham |
| 2010/0256626 A1 | 10/2010 | Muller et al. |
| 2010/0262239 A1 | 10/2010 | Boyden et al. |
| 2010/0318129 A1 | 12/2010 | Seme et al. |
| 2010/0331883 A1 | 12/2010 | Schmitz et al. |
| 2011/0004076 A1 | 1/2011 | Janna et al. |
| 2011/0057756 A1 | 3/2011 | Marinescu et al. |
| 2011/0066188 A1 | 3/2011 | Seme et al. |
| 2011/0098748 A1 | 4/2011 | Jangra |
| 2011/0152725 A1 | 6/2011 | Demir et al. |
| 2011/0196435 A1 | 8/2011 | Forsell |
| 2011/0202138 A1 | 8/2011 | Shenoy et al. |
| 2011/0230883 A1 | 9/2011 | Zahrly et al. |
| 2011/0237861 A1 | 9/2011 | Pool |
| 2011/0238126 A1 | 9/2011 | Soubeiran |
| 2011/0257655 A1 | 10/2011 | Copf, Jr. |
| 2011/0284014 A1 | 11/2011 | Cadeddu et al. |
| 2012/0004494 A1 | 1/2012 | Payne et al. |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0088953 A1 | 4/2012 | King |
| 2012/0109207 A1 | 5/2012 | Trieu |
| 2012/0116535 A1 | 5/2012 | Ratron et al. |
| 2012/0158061 A1 | 6/2012 | Koch et al. |
| 2012/0172883 A1 | 7/2012 | Sayago |
| 2012/0179215 A1 | 7/2012 | Soubeiran |
| 2012/0221106 A1 | 8/2012 | Makower et al. |
| 2012/0271353 A1 | 10/2012 | Barry |
| 2012/0296234 A1 | 11/2012 | Wilhelm et al. |
| 2012/0329882 A1 | 12/2012 | Messersmith et al. |
| 2013/0013066 A1 | 1/2013 | Landry et al. |
| 2013/0072932 A1 | 3/2013 | Stauch |
| 2013/0123847 A1 | 5/2013 | Anderson et al. |
| 2013/0138017 A1 | 5/2013 | Jundt et al. |
| 2013/0138154 A1 | 5/2013 | Reiley |
| 2013/0150863 A1 | 6/2013 | Baumgartner |
| 2013/0150889 A1 | 6/2013 | Fening et al. |
| 2013/0178903 A1 | 7/2013 | Abdou |
| 2013/0211521 A1 | 8/2013 | Shenoy et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261672 A1 | 10/2013 | Horvath |
| 2013/0296863 A1 | 11/2013 | Globerman et al. |
| 2013/0296864 A1 | 11/2013 | Burley et al. |
| 2013/0296940 A1 | 11/2013 | Northcutt et al. |
| 2013/0325006 A1 | 12/2013 | Michelinie et al. |
| 2013/0325071 A1 | 12/2013 | Niemiec et al. |
| 2014/0005788 A1 | 1/2014 | Haaja et al. |
| 2014/0025172 A1 | 1/2014 | Lucas et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0088715 A1 | 3/2014 | Ciupik |
| 2014/0128920 A1 | 5/2014 | Kantelhardt |
| 2014/0163664 A1 | 6/2014 | Goldsmith |
| 2014/0236234 A1 | 8/2014 | Kroll et al. |
| 2014/0236311 A1 | 8/2014 | Vicatos et al. |
| 2014/0257412 A1 | 9/2014 | Patty et al. |
| 2014/0261793 A1* | 9/2014 | Shah ............ A61M 27/006 137/553 |
| 2014/0277446 A1 | 9/2014 | Clifford et al. |
| 2014/0296918 A1 | 10/2014 | Fening et al. |
| 2014/0303538 A1 | 10/2014 | Baym et al. |
| 2014/0303539 A1 | 10/2014 | Baym et al. |
| 2014/0358150 A1 | 12/2014 | Kaufman et al. |
| 2015/0105782 A1 | 4/2015 | D'Lima et al. |
| 2015/0105824 A1 | 4/2015 | Moskowitz et al. |
| 2015/0313745 A1 | 11/2015 | Cheng |
| 2021/0100588 A1 | 4/2021 | Cheng et al. |

FOREIGN PATENT DOCUMENTS

| | | |
|---|---|---|
| DE | 1541262 A1 | 6/1969 |
| DE | 8515687 U1 | 12/1985 |
| DE | 19626230 A1 | 1/1998 |
| DE | 19745654 A1 | 4/1999 |
| DE | 102005045070 | 4/2007 |
| EP | 0663184 A1 | 7/1995 |
| EP | 1803413 A2 | 7/2007 |
| EP | 1905388 A1 | 4/2008 |
| FR | 2901991 A1 | 12/2007 |
| FR | 2900563 B1 | 8/2008 |
| FR | 2892617 B1 | 9/2008 |
| FR | 2916622 B1 | 9/2009 |
| FR | 2961386 B1 | 7/2012 |
| JP | H0956736 | 3/1997 |
| JP | 2002500063 A | 1/2002 |
| JP | 2014521386 A | 8/2014 |
| WO | WO1998044858 A1 | 1/2002 |
| WO | WO1999051160 A1 | 1/2002 |
| WO | WO2001024697 A1 | 1/2002 |
| WO | WO2001045485 A3 | 1/2002 |
| WO | WO2001045487 A2 | 1/2002 |
| WO | WO2001067973 A2 | 1/2002 |
| WO | WO2001078614 A1 | 1/2002 |
| WO | 2002034131 | 5/2002 |
| WO | 2007144489 A2 | 12/2007 |
| WO | WO2007015239 A3 | 1/2008 |
| WO | WO2007013059 A3 | 4/2009 |
| WO | WO2011116158 A3 | 1/2012 |
| WO | WO2013119528 A1 | 8/2013 |
| WO | WO2014040013 A1 | 3/2014 |
| WO | 2015168175 A1 | 11/2015 |
| WO | 2017100774 | 6/2017 |

OTHER PUBLICATIONS

Ahlbom et al., "Guidelines for limiting exposure to time-varying electric, magnetic, and electromagnetic fields (up to 300 GHz).

(56) References Cited

OTHER PUBLICATIONS

International Commission on Non-Ionizing Radiation Protection.", Health Physics, 1998, pp. 494-522, 74, No. 4.

Amer et al., "Evaluation of treatment of late-onset tibia vara using gradual angulation translation high tibial osteotomy", ACTA Orthopaedica Belgica, 2010, pp. 360-366, 76, No. 3.

Angrisani et al., "Lap-Band® Rapid Port™ System: Preliminary results in 21 patients", Obesity Surgery, 2005, p. 936, 15, No. 7.

Baumgart et al., "A fully implantable, programmable distraction nail (Fitbone)—new perspectives for corrective and reconstructive limb surgery.", Practice of Intramedullary Locked Nails, 2006, pp. 189-198.

Baumgart et al., "The bioexpandable prosthesis: A new perspective after resection of malignant bone tumors in children.", J Pediatr Hematol Oncol, 2005, pp. 452-455, 27, No. 8.

Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.

Boudjemline et al., "Off-label use of an adjustable gastric banding system for pulmonary artery banding.", The Journal of Thoracic and Cardiovascular Surgery, 2006, pp. 1130-1135, 131, No. 5.

Brown et al., "Single port surgery and the Dundee Endocone.", SAGES Annual Scientific Sessions: Emerging Technology Poster Abstracts, 2007, ETP007, pp. 323-324.

Buchowski et al., "Temporary internal distraction as an aid to correction of severe scoliosis", J Bone Joint Surg Am, 2006, pp. 2035-2041, 88-A, No. 9.

Burghardt et al., "Mechanical failure of the Intramedullary Skeletal Kinetic Distractor in limb lengthening.", J Bone Joint Surg Br, 2011, pp. 639-643, 93-B, No. 5.

Burke, "Design of a minimally invasive non fusion device for the surgical management of scoliosis in the skeletally immature", Studies in Health Technology and Informatics, 2006, pp. 378-384, 123.

Carter et al., "A cumulative damage model for bone fracture.", Journal of Orthopaedic Research, 1985, pp. 84-90, 3, No. 1.

Chapman et al., "Laparoscopic adjustable gastric banding in the treatment of obesity: A systematic literature review.", Surgery, 2004, pp. 326-351, 135, No. 3.

Cole et al., "Operative technique intramedullary skeletal kinetic distractor: Tibial surgical technique.", Orthofix, 2005.

Cole et al., "The intramedullary skeletal kinetic distractor (ISKD): first clinical results of a new intramedullary nail for lengthening of the femur and tibia.", Injury, 2001, pp. S-D-129-S-D-139, 32.

Dailey et al., "A novel intramedullary nail for micromotion stimulation of tibial fractures.", Clinical Biomechanics, 2012, pp. 182-188, 27, No. 2.

Daniels et al., "A new method for continuous intraoperative measurement of Harrington rod loading patterns.", Annals of Biomedical Engineering, 1984, pp. 233-246, 12, No. 3.

De Giorgi et al., "Cotrel-Dubousset instrumentation for the treatment of severe scoliosis.", European Spine Journal, 1999, pp. 8-15, No. 1.

Dorsey et al., "The stability of three commercially available implants used in medial opening wedge high tibial osteotomy.", Journal of Knee Surgery, 2006, pp. 95-98, 19, No. 2.

Edeland et al., "Instrumentation for distraction by limited surgery in scoliosis treatment.", Journal of Biomedical Engineering, 1981, pp. 143-146, 3, No. 2.

Elsebaie, "Single growing rods (Review of 21 cases). Changing the foundations: Does it affect the results?", Journal of Child Orthop, 2007, 1:258.

Ember et al., "Distraction forces required during growth rod lengthening.", J of Bone Joint Surg BR, 2006, p. 229, 88-B, No. Suppl. II.

European Patent Office, "Observations by a third party under Article 115 EPC in EP08805612 by Soubeiran.", 2010.

Fabry et al., "A technique for prevention of port complications after laparoscopic adjustable silicone gastric banding.", Obesity Surgery, 2002, pp. 285-288, 12, No. 2.

Fried et al., "In vivo measurements of different gastric band pressures towards the gastric wall at the stoma region.", Obesity Surgery, 2004, p. 914, 14, No. 7.

Gao et al., CHD7 gene polymorphisms are associated with susceptibility to idiopathic scoliosis, American Journal of Human Genetics, 2007, pp. 957-965, 80.

Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).

Gillespie et al. "Harrington instrumentation without fusion.", J Bone Joint Surg Br, 1981, p. 461, 63-B, No. 3.

Goodship et al., "Strain rate and timing of stimulation in mechanical modulation of fracture healing.", Clinical Orthopaedics and Related Research, 1998, pp. S105-S115, No. 355S.

Grass et al., "Intermittent distracting rod for correction of high neurologic risk congenital scoliosis.", SPINE, 1997, pp. 1922-1927, 22, No. 16.

Gray, "Gray's anatomy of the human body.", http://education.yahoo.com/reference/gray/subjects/subject/128, published Jul. 1, 2007.

Grimer et al. "Non-invasive extendable endoprostheses for children—Expensive but worth it!", International Society of Limb Salvage 14th International Symposium on Limb Salvage, 2007.

Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.

Guichet et al. "Gradual femoral lengthening with the Albizzia intramedullary nail", J Bone Joint Surg Am, 2003, pp. 838-848, 85-A, No. 5.

Gupta et al., "Non-invasive distal femoral expandable endoprosthesis for limb-salvage surgery in paediatric tumours.", J Bone Joint Surg Br, 2006, pp. 649-654, 88-B, No. 5.

Hankemeier et al., "Limb lengthening with the Intramedullary Skeletal Kinetic Distractor (ISKD).", Oper Orthop Traumatol, 2005, pp. 79-101, 17, No. 1.

Harrington, "Treatment of scoliosis. Correction and internal fixation by spine instrumentation.", J Bone Joint Surg Am, 1962, pp. 591-610, 44-A, No. 4.

Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.

Hofmeister et al., "Callus distraction with the Albizzia nail.", Practice of Intramedullary Locked Nails, 2006, pp. 211-215.

Horbach et al., "First experiences with the routine use of the Rapid Port™ system with the Lap-Band®.", Obesity Surgery, 2006, p. 418, 16, No. 4.

Hyodo et al., "Bone transport using intramedullary fixation and a single flexible traction cable.", Clinical Orthopaedics and Related Research, 1996, pp. 256-268, 325.

International Commission on Non-Ionizing Radiation Protection, "Guidelines on limits of exposure to static magnetic fields." Health Physics, 2009, pp. 504-514, 96, No. 4.

INVIS®/Lamello Catalog, 2006, Article No. 68906A001 GB.

Kasliwal et al., "Management of high-grade spondylolisthesis.", Neurosurgery Clinics of North America, 2013, pp. 275-291, 24, No. 2.

Kenawey et al., "Leg lengthening using intramedullay skeletal kinetic distractor: Results of 57 consecutive applications.", Injury, 2011, pp. 150-155, 42, No. 2.

Kent et al., "Assessment and correction of femoral malrotation following intramedullary nailing of the femur.", Acta Orthop Belg, 2010, pp. 580-584, 76, No. 5.

Klemme et al., "Spinal instrumentation without fusion for progressive scoliosis in young children", Journal of Pediatric Orthopaedics. 1997, pp. 734-742, 17, No. 6.

(56) References Cited

OTHER PUBLICATIONS

Korenkov et al., "Port function after laparoscopic adjustable gastric banding for morbid obesity.", Surgical Endoscopy, 2003, pp. 1068-1071, 17, No. 7.
Krieg et al., "Leg lengthening with a motorized nail in adolescents.", Clinical Orthopaedics and Related Research, 2008, pp. 189-197, 466, No. 1.
Kucukkaya et al., "The new intramedullary cable bone transport technique.", Journal of Orthopaedic Trauma, 2009, pp. 531-536, 23, No. 7.
Lechner et al., "In vivo band manometry: A new method in band adjustment", Obesity Surgery, 2005, p. 935, 15, No. 7.
Lechner et al., "Intra-band manometry for band adjustments: The basics", Obesity Surgery, 2006, pp. 417-418, 16, No. 4.
Li et al., "Bone transport over an intramedullary nail: A case report with histologic examination of the regenerated segment.", Injury, 1999, pp. 525-534, 30, No. 8.
Lonner, "Emerging minimally invasive technologies for the management of scoliosis.", Orthopedic Clinics of North America, 2007, pp. 431-440, 38, No. 3.
Matthews et al., "Magnetically adjustable intraocular lens.", Journal of Cataract and Refractive Surgery, 2003, pp. 2211-2216, 29, No. 11.
Micromotion, "Micro Drive Engineering. General catalogue.", 2009, pp. 14-24.
Mineiro et al., "Subcutaneous rodding for progressive spinal curvatures: Early results.", Journal of Pediatric Orthopaedics, 2002, pp. 290-295, 22, No. 3.
Moe et al., "Harrington instrumentation without fusion plus external orthotic support for the treatment of difficult curvature problems in young children.", Clinical Orthopaedics and Related Research, 1984, pp. 35-45, 185.
Montague et al., "Magnetic gear dynamics for servo control.", Melecon 2010—2010 15th IEEE Mediterranean Electrotechnical Conference, Valletta, 2010, pp. 1192-1197.
Montague et al., "Servo control of magnetic gears.", IEEE/ASME Transactions on Mechatronics, 2012, pp. 269-278, 17, No. 2.
Nachemson et al., "Intravital wireless telemetry of axial forces in Harrington distraction rods in patients with idiopathic scoliosis.", The Journal of Bone and Joint Surgery, 1971, pp. 445-465, 53, No. 3.
Nachlas et al., "The cure of experimental scoliosis by directed growth control.", The Journal of Bone and Joint Surgery, 1951, pp. 24-34, 33-A, No. 1.
Newton et al., "Fusionless scoliosis correction by anterolateral tethering . . . can it work?. ", 39th Annual Scoliosis Research Society Meeting, 2004.
Oh et al., "Bone transport over an intramedullary nail for reconstruction of long bone defects in tibia.", Archives of Orthopaedic and Trauma Surgery, 2008, pp. 801-808, 128, No. 8.
Ozcivici et al., "Mechanical signals as anabolic agents in bone.", Nature Reviews Rheumatology, 2010, pp. 50-59, 6, No. 1.
Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.
Prontes, "Longest bone in body.", eHow.com, 2012.
Rathjen et al., "Clinical and radiographic results after implant removal in idiopathic scoliosis.", SPINE, 2007, pp. 2184-2188, 32, No. 20.
Ren et al., "Laparoscopic adjustable gastric banding: Surgical technique", Journal of Laparoendoscopic & Advanced Surgical Techniques, 2003, pp. 257-263, 13, No. 4.
Reyes-Sanchez et al., "External fixation for dynamic correction of severe scoliosis", The Spine Journal, 2005, pp. 418-426, 5, No. 4.
Rinsky et al., "Segmental instrumentation without fusion in children with progressive scoliosis.", Journal of Pediatric Orthopedics, 1985, pp. 687-690, 5, No. 6.
Rode et al., "A simple way to adjust bands under radiologic control", Obesity Surgery, 2006, p. 418, 16, No. 4.
Schmerling et al., "Using the shape recovery of nitinol in the Harrington rod treatment of scoliosis.", Journal of Biomedical Materials Research, 1976, pp. 879-892, 10, No. 6.
Scott et al., "Transgastric, transcolonic and transvaginal cholecystectomy using magnetically anchored instruments.", SAGES Annual Scientific Sessions, Poster Abstracts, Apr. 18-22, 2007, P511, p. 306.
Sharke, "The machinery of life", Mechanical Engineering Magazine, Feb. 2004, Printed from Internet site Oct. 24, 2007 http://www.memagazine.org/contents/current/features/moflife/moflife.html.
Shiha et al., "Ilizarov gradual correction of genu varum deformity in adults.", Acta Orthop Belg, 2009, pp. 784-791, 75, No. 6.
Simpson et al., "Femoral lengthening with the intramedullary skeletal kinetic distractor.", Journal of Bone and Joint Surgery, 2009, pp. 955-961, 91-B, No. 7.
Smith, "The use of growth-sparing instrumentation in pediatric spinal deformity.", Orthopedic Clinics of North America, 2007, pp. 547-552, 38, No. 4.
Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).
Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).
Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.
Sun et al., "Masticatory mechanics of a mandibular distraction osteogenesis site: Interfragmentary micromovement.", Bone, 2007, pp. 188-196, 41, No. 2.
Synthes Spine, "VEPTR II. Vertical Expandable Prosthetic Titanium Rib II: Technique Guide.", 2008, 40 pgs.
Synthes Spine, "VEPTR Vertical Expandable Prosthetic Titanium Rib, Patient Guide.", 2005, 26 pgs.
Takaso et al., "New remote-controlled growing-rod spinal instrumentation possibly applicable for scoliosis in young children.", Journal of Orthopaedic Science, 1998, pp. 336-340, 3, No. 6.
Teli et al., "Measurement of forces generated during distraction of growing rods.", Journal of Children's Orthopaedics, 2007, pp. 257-258, 1, No. 4.
Tello, "Harrington instrumentation without arthrodesis and consecutive distraction program for young children with severe spinal deformities: Experience and technical details.", The Orthopedic Clinics of North America, 1994, pp. 333-351, 25, No. 2.
Thaller et al., "Limb lengthening with fully implantable magnetically actuated mechanical nails (PHENIX®)—Preliminary results.", Injury, 2014 (E-published Oct. 28, 2013), pp. S60-S65, 45.
Thompson et al., "Early onset scoliosis: Future directions", 2007, J Bone Joint Surg Am, pp. 163-166, 89-A, Suppl 1.
Thompson et al., "Growing rod techniques in early-onset scoliosis", Journal of Pediatric Orthopedics, 2007, pp. 354-361, 27, No. 3.
Thonse et al., "Limb lengthening with a fully implantable, telescopic, intramedullary nail.", Operative Techniques in Orthopedics, 2005, pp. 355-362, 15, No. 4.
Trias et al., "Dynamic loads experienced in correction of idiopathic scoliosis using two types of Harrington rods.", SPINE, 1979, pp. 228-235, 4, No. 3.
Verkerke et al., "An extendable modular endoprosthetic system for bone tumor management in the leg", Journal of Biomedical Engineering, 1990, pp. 91-96, 12, No. 2.
Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.

(56) References Cited

OTHER PUBLICATIONS

Verkerke et al., "Development and test of an extendable endoprosthesis for bone reconstruction in the leg.", The International Journal of Artificial Organs, 1994, pp. 155-162, 17, No. 3.
Weiner et al., "Initial clinical experience with telemetrically adjustable gastric banding", Surgical Technology International, 2005, pp. 63-69, 15.
Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.
White, III et al., "The clinical biomechanics of scoliosis.", Clinical Orthopaedics and Related Research, 1976, pp. 100-112, 118.
Yonnet, "A new type of permanent magnet coupling.", IEEE Transactions on Magnetics, 1981, pp. 2991-2993, 17, No. 6.
Yonnet, "Passive magnetic bearings with permanent magnets.", IEEE Transactions on Magnetics, 1978, pp. 803-805, 14, No. 5.
Zheng et al., "Force and torque characteristics for magnetically driven blood pump.", Journal of Magnetism and Magnetic Materials, 2002, pp. 292-302, 241, No. 2.

\* cited by examiner

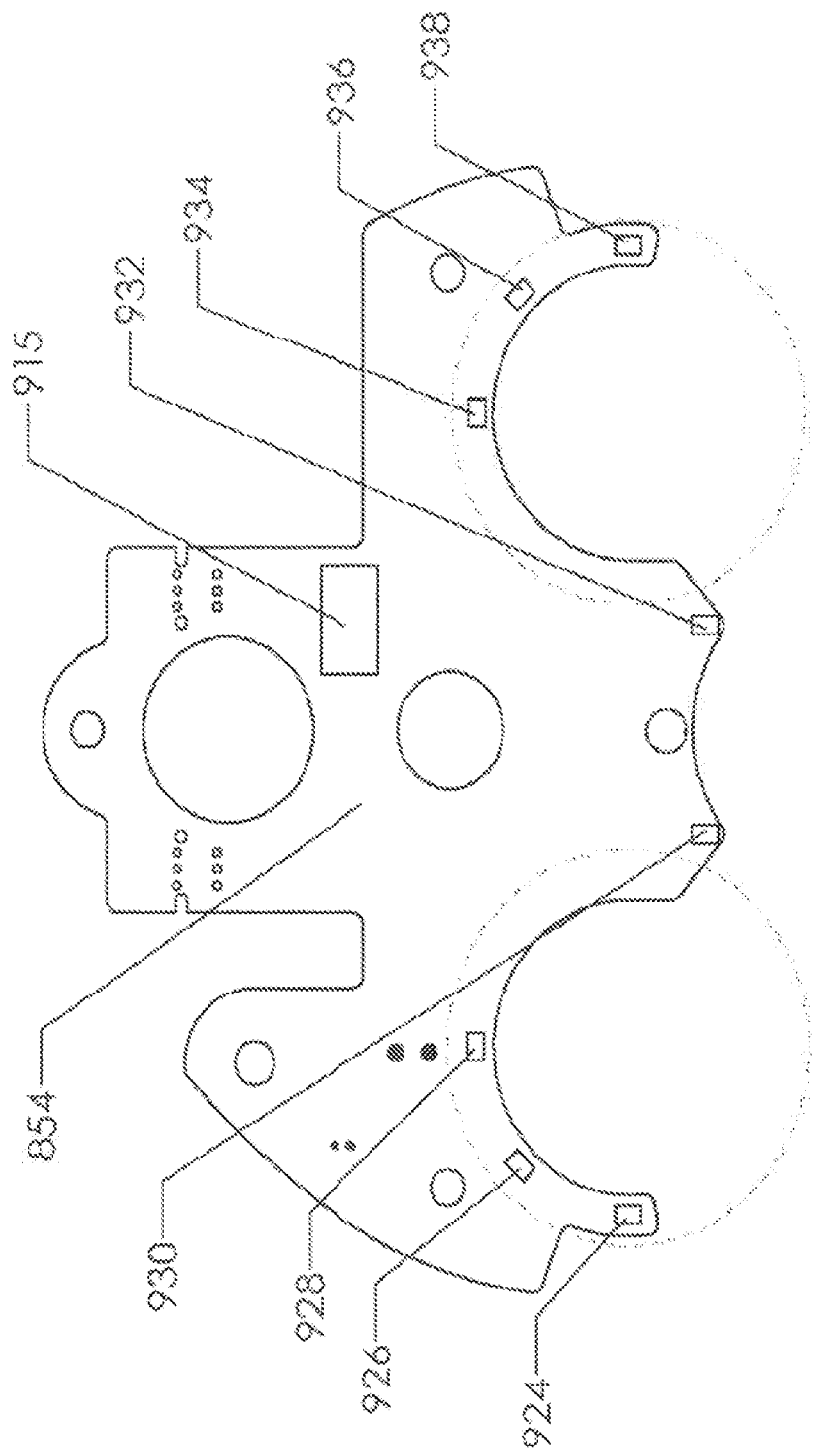

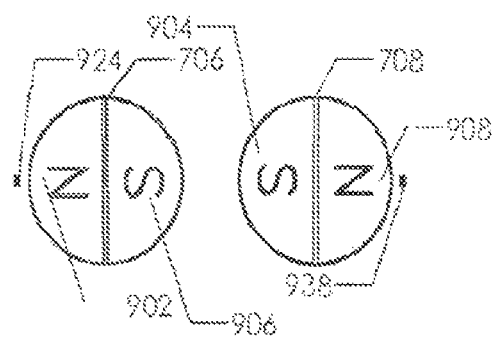 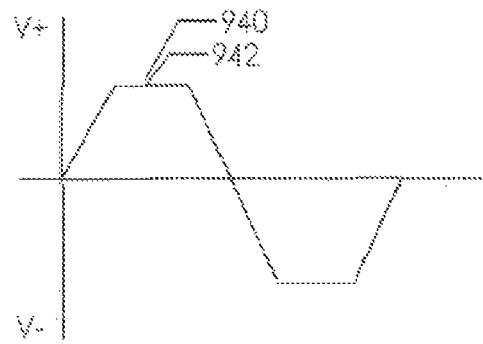
FIG. 9A  FIG. 9B
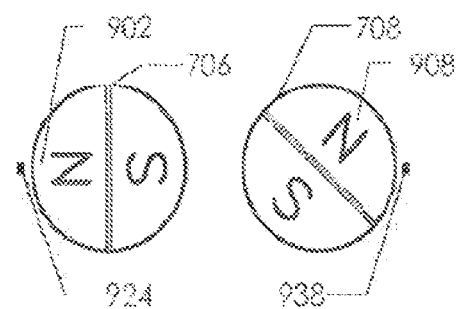 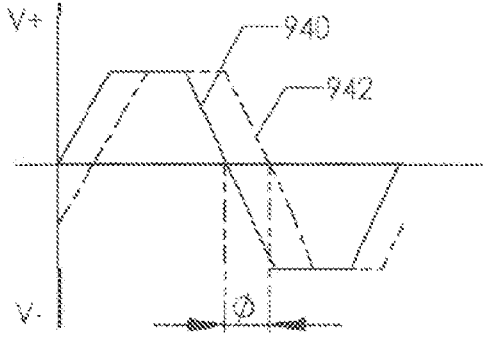
FIG. 9C  FIG. 9D
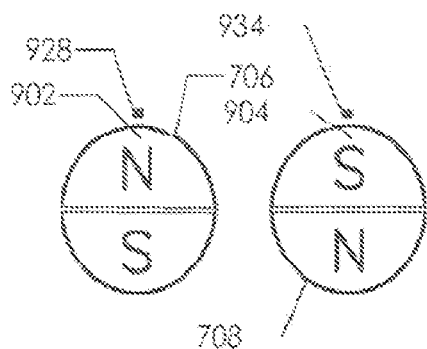 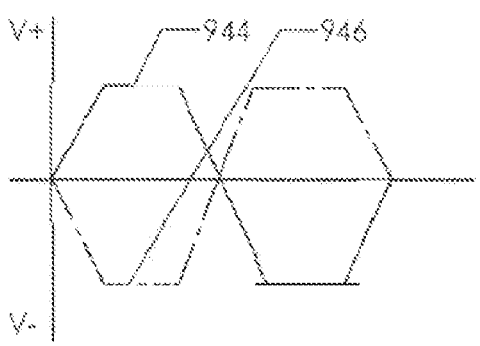
FIG. 10A  FIG. 10B

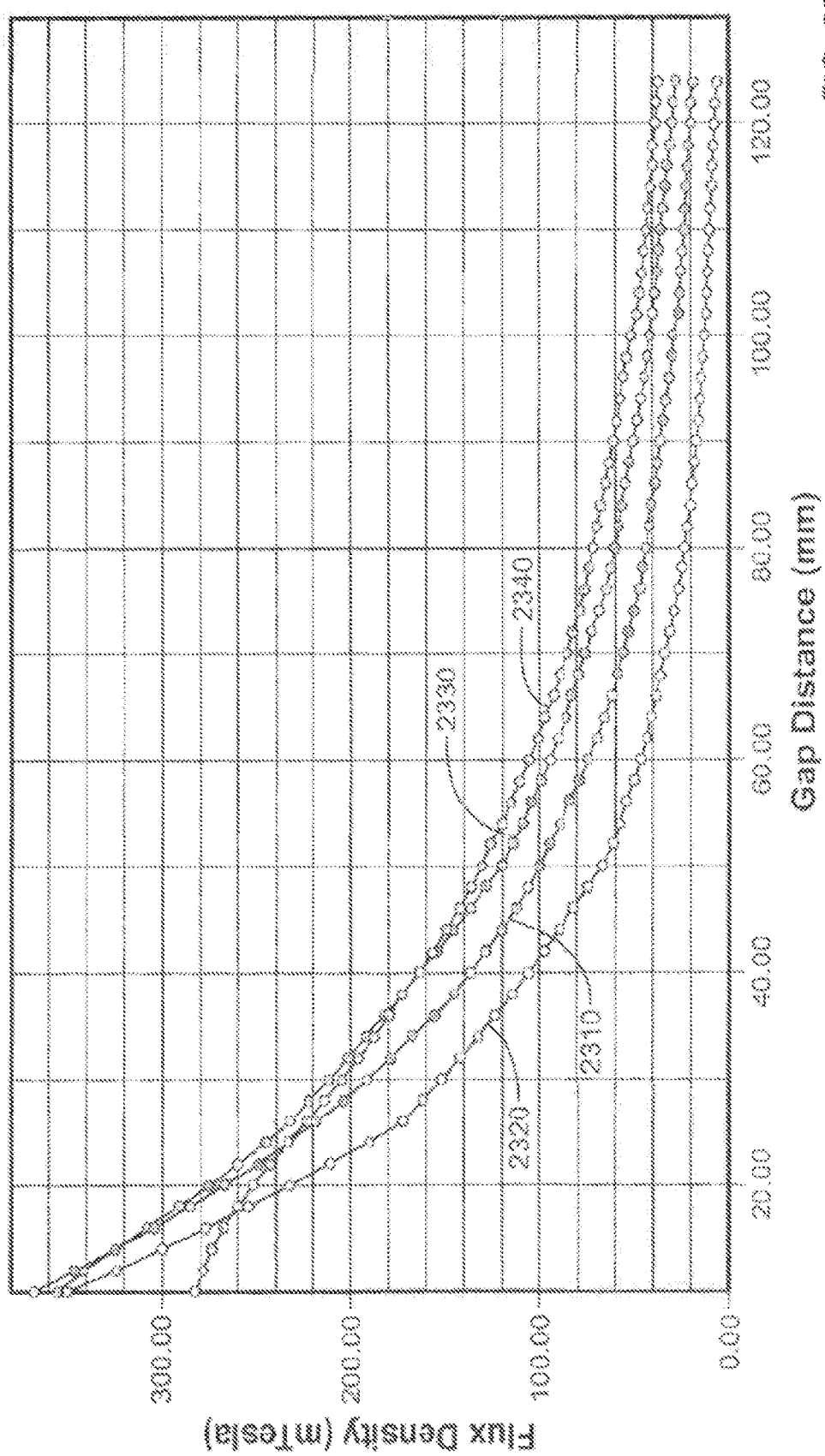

EXTERNAL ADJUSTMENT DEVICE FOR DISTRACTION DEVICE

CROSS-REFERENCE TO RELATED APPLICATION

The present application is a continuation of U.S. patent application Ser. No. 17/066,338 filed on Oct. 8, 2020, which is a continuation of U.S. patent application Ser. No. 16/004,099 filed on Jun. 8, 2018 (now U.S. Pat. No. 10,835,290), which is a continuation of PCT/US16/66179, filed on Dec. 12, 2016, which claims the benefit of priority from U.S. Provisional Patent Application No. 62/276,196, filed on Jan. 7, 2016, and U.S. Provisional Patent Application No. 62/265,430 filed on Dec. 10, 2015, the entire contents of which are hereby expressly incorporated by reference into this disclosure as if set forth in their entirety herein.

FIELD OF THE INVENTION

The field of the invention generally relates to medical devices for treating disorders of the skeletal system.

BACKGROUND

Scoliosis is a general term for the sideways (lateral) curving of the spine, usually in the thoracic or thoracolumbar region. Scoliosis is commonly broken up into different treatment groups, Adolescent Idiopathic Scoliosis, Early Onset Scoliosis and Adult Scoliosis.

Adolescent Idiopathic Scoliosis (AIS) typically affects children between ages 10 and 16, and becomes most severe during growth spurts that occur as the body is developing. One to two percent of children between ages 10 and 16 have some amount of scoliosis. Of every 1000 children, two to five develop curves that are serious enough to require treatment. The degree of scoliosis is typically described by the Cobb angle, which is determined, usually from x-ray images, by taking the most tilted vertebrae above and below the apex of the curved portion and measuring the angle between intersecting lines drawn perpendicular to the top of the top vertebrae and the bottom of the bottom. The term idiopathic refers to the fact that the exact cause of this curvature is unknown. Some have speculated that scoliosis occurs when, during rapid growth phases, the ligamentum flavum of the spine is too tight and hinders symmetric growth of the spine. For example, as the anterior portion of the spine elongates faster than the posterior portion, the thoracic spine begins to straighten, until it curves laterally, often with an accompanying rotation. In more severe cases, this rotation actually creates a noticeable deformity, wherein one shoulder is lower than the other. Currently, many school districts perform external visual assessment of spines, for example in all fifth grade students. For those students in whom an "S" shape or "C" shape is identified, instead of an "I" shape, a recommendation is given to have the spine examined by a physician, and commonly followed-up with periodic spinal x-rays.

Typically, patients with a Cobb angle of 20° or less are not treated, but are continually followed up, often with subsequent x-rays. Patients with a Cobb angle of 40° or greater are usually recommended for fusion surgery. It should be noted that many patients do not receive this spinal assessment, for numerous reasons. Many school districts do not perform this assessment, and many children do not regularly visit a physician, so often, the curve progresses rapidly and severely. There is a large population of grown adults with untreated scoliosis, in extreme cases with a Cobb angle as high as or greater than 90°. Many of these adults, though, do not have pain associated with this deformity, and live relatively normal lives, though oftentimes with restricted mobility and motion. In AIS, the ratio of females to males for curves under 10° is about one to one, however, at angles above 30°, females outnumber males by as much as eight to one. Fusion surgery can be performed on the AIS patients or on adult scoliosis patients. In a typical posterior fusion surgery, an incision is made down the length of the back and Titanium or stainless steel straightening rods are placed along the curved portion. These rods are typically secured to the vertebral bodies, for example with hooks or bone screws, or more specifically pedicle screws, in a manner that allows the spine to be straightened. Usually, at the section desired for fusion, the intervertebral disks are removed and bone graft material is placed to create the fusion. If this is autologous material, the bone is harvested from a hip via a separate incision.

Alternatively, the fusion surgery may be performed anteriorly. A lateral and anterior incision is made for access. Usually, one of the lungs is deflated in order to allow access to the spine from this anterior approach. In a less-invasive version of the anterior procedure, instead of the single long incision, approximately five incisions, each about three to four cm long are made in several of the intercostal spaces (between the ribs) on one side of the patient. In one version of this minimally invasive surgery, tethers and bone screws are placed and are secured to the vertebra on the anterior convex portion of the curve. Currently, clinical trials are being performed which use staples in place of the tether/screw combination. One advantage of this surgery in comparison with the posterior approach is that the scars from the incisions are not as dramatic, though they are still located in a visible area, when a bathing suit, for example, is worn. The staples have had some difficulty in the clinical trials. The staples tend to pull out of the bone when a critical stress level is reached.

In some cases, after surgery, the patient will wear a protective brace for a few months as the fusing process occurs. Once the patient reaches spinal maturity, it is difficult to remove the rods and associated hardware in a subsequent surgery, because the fusion of the vertebra usually incorporates the rods themselves. Standard practice is to leave this implant in for life. With either of these two surgical methods, after fusion, the patient's spine is now straight, but depending on how many vertebra were fused, there are often limitations in the degree of flexibility, both in bending and twisting. As these fused patients mature, the fused section can impart large stresses on the adjacent non-fused vertebra, and often, other problems including pain can occur in these areas, sometimes necessitating further surgery. This tends to be in the lumbar portion of the spine that is prone to problems in aging patients. Many physicians are now interested in fusionless surgery for scoliosis, which may be able to eliminate some of the drawbacks of fusion.

One group of patients in which the spine is especially dynamic is the subset known as Early Onset Scoliosis (EOS), which typically occurs in children before the age of five, and more often in boys than in girls. This is a more rare condition, occurring in only about one or two out of 10,000 children, but can be severe, sometimes affecting the normal development of organs. Because of the fact that the spines of these children will still grow a large amount after treatment, non-fusion distraction devices known as growing rods and a device known as the EPTR Vertical Expandable Prosthetic Titanium Rib ("Titanium Rib") have been developed. These devices are typically adjusted approximately every six months, to match the child's growth, until the child is at least eight years old, sometimes until they are 15 years old. Each adjustment requires a surgical incision to access the adjustable portion of the device. Because the patients may receive the device at an age as early as six months old, this treatment requires a large number of surgeries. Because of the multiple surgeries, these patients have a rather high preponderance of infection.

Returning to the AIS patients, the treatment methodology for those with a Cobb angle between 20° and 40° is quite controversial. Many physicians proscribe a brace (for example, the Boston Brace), that the patient must wear on their body and under their clothes 18 to 23 hours a day until they become skeletally mature, for example to age 16. Because these patients are all passing through their socially demanding adolescent years, it is quite a serious prospect to be forced with the choice of either wearing a somewhat bulky brace that covers most of the upper body, having fusion surgery that may leave large scars and also limit motion, or doing nothing and running the risk of becoming disfigured and possibly disabled. It is commonly known that many patients have at times hidden their braces, for example, in a bush outside of school, in order to escape any related embarrassment. The patient compliance with brace wearing has been so problematic that there have been special braces constructed which sense the body of the patient, and keep track of the amount of time per day that the brace is worn. Patients have even been known to place objects into unworn braces of this type in order to fool the sensor. Coupled with the inconsistent patient compliance with brace usage, is a feeling by many physicians that braces, even if used properly, are not at all effective at curing scoliosis. These physicians may agree that bracing can possibly slow down or even temporarily stop curve (Cobb angle) progression, but they have noted that as soon as the treatment period ends and the brace is no longer worn, often the scoliosis rapidly progresses, to a Cobb angle even more severe than it was at the beginning of treatment. Some say the reason for the supposed ineffectiveness of the brace is that it works only on a portion of the torso, and not on the entire spine. Currently a prospective, randomized 500 patient clinical trial known as BrAIST (Bracing in Adolescent Idiopathic Scoliosis Trial) is enrolling patients, 50% of whom will be treated with the brace and 50% of who will simply be watched. The Cobb angle data will be measured continually up until skeletal maturity, or until a Cobb angle of 50° is reached, at which time the patient will likely undergo surgery. Many physicians feel that the BrAIST trial will show that braces are completely ineffective. If this is the case, the quandary about what to do with AIS patients who have a Cobb angle of between "20° and 40°" will only become more pronounced. It should be noted that the "20° to 40°" patient population is as much as ten times larger than the "40° and greater" patient population.

Distraction osteogenesis, also known as distraction callotasis and osteodistraction has been used successfully to lengthen long bones of the body. Typically, the bone, if not already fractured, is purposely fractured by means of a corticotomy, and the two segments of bone are gradually distracted apart, which allows new bone to form in the gap. If the distraction rate is too high, there is a risk of nonunion, if the rate is too low, there is a risk that the two segments will completely fuse to each other before the distraction period is complete. When the desired length of the bone is achieved using this process, the bone is allowed to consolidate. Distraction osteogenesis applications are mainly focused on the growth of the femur or tibia, but may also include the humerus, the jaw bone (micrognathia), or other bones. The reasons for lengthening or growing bones are multifold, the applications including, but not limited to: post osteosarcoma bone cancer; cosmetic lengthening (both legs-femur and/or tibia) in short stature or dwarfism/achondroplasia; lengthening of one limb to match the other (congenital, posttrauma, post-skeletal disorder, prosthetic knee joint), nonunions.

Distraction osteogenesis using external fixators has been done for many years, but the external fixator can be unwieldy for the patient. It can also be painful, and the patient is subject to the risk of pin track infections, joint stiffness, loss of appetite, depression, cartilage damage and other side effects. Having the external fixator in place also delays the beginning of rehabilitation.

In response to the shortcomings of external fixator distraction, intramedullary distraction nails have been surgically implanted which are contained entirely within the bone. Some are automatically lengthened via repeated rotation of the patient's limb. This can sometimes be painful to the patient, and can often proceed in an uncontrolled fashion. This therefore makes it difficult to follow the strict daily or weekly lengthening regime that avoids nonunion (if too fast) or early consolidation (if too slow). Lower limb distraction rates are on the order of one mm per day. Other intramedullary nails have been developed which have an implanted motor and are remotely controlled by an antenna. These devices are therefore designed to be lengthened in a controlled manner, but due to their complexity, may not be manufacturable as an affordable product. Others have proposed intramedullary distractors containing and implanted magnet, which allows the distraction to be driven electromagnetically by an external stator. Because of the complexity and size of the external stator, this technology has not been reduced to a simple and cost-effective device that can be taken home, to allow patients to do daily lengthening.

SUMMARY

In one embodiment, an external adjustment device includes at least one permanent magnet configured for rotation about an axis. The external adjustment device further includes a first handle extending linearly at a first end of the device and a second handle disposed at a second end of the device, the second handle extending in a direction that is angled relative to the first handle. The external adjustment device includes a motor mounted inside the first handle and a first button located in the proximity to one of the first handle or the second handle, the first button configured to be operated by the thumb of a hand that grips the one of the first handle or second handle. The first button is configured to actuate the motor causing the at least one permanent magnet to rotate about the axis in a first direction.

In another embodiment, an external adjustment device includes at least one permanent magnet configured for rotation about an axis and a motor configured for rotating the at least one permanent magnet about the axis. The external adjustment device includes a first handle extending linearly at a first end of the device and a second handle disposed at a second end of the device, the second handle extending in a direction that is substantially off axis with respect to the first handle, wherein one of the first and second handle comprises a looped shape. A first drive button is located in the proximity to one of the first handle or the second handle, the first drive button configured to be operated by the thumb of a hand that grips the one of the first handle or second handle. The first drive button is configured to actuate the motor causing the at least one permanent magnet to rotate about the axis in a first direction.

BRIEF DESCRIPTION OF THE DRAWINGS

FIG. 8 illustrates a view of the clock positions of Hall effect sensors on the printed circuit board of the external adjustment device.

FIG. 9A illustrates a particular configuration of Hall effect sensors according to one embodiment.

FIG. 9B illustrates output voltage of the Hall effect sensors of the configuration in FIG. 9A.

FIG. 9C illustrates the configuration of FIG. 9A, with the magnets in a nonsynchronous condition.

FIG. 9D illustrates the output voltage of the Hall effect sensors of the configuration in FIG. 9C.

FIG. 10A illustrates a particular configuration of Hall effect sensors according to another embodiment.

FIG. 10B illustrates the output voltage of the Hall effect sensors of the configuration in FIG. 10A.

FIG. 23 illustrates a graph of flux density plotted against gap distance for external magnets having various rotational offsets.

DETAILED DESCRIPTION

Figure 1:
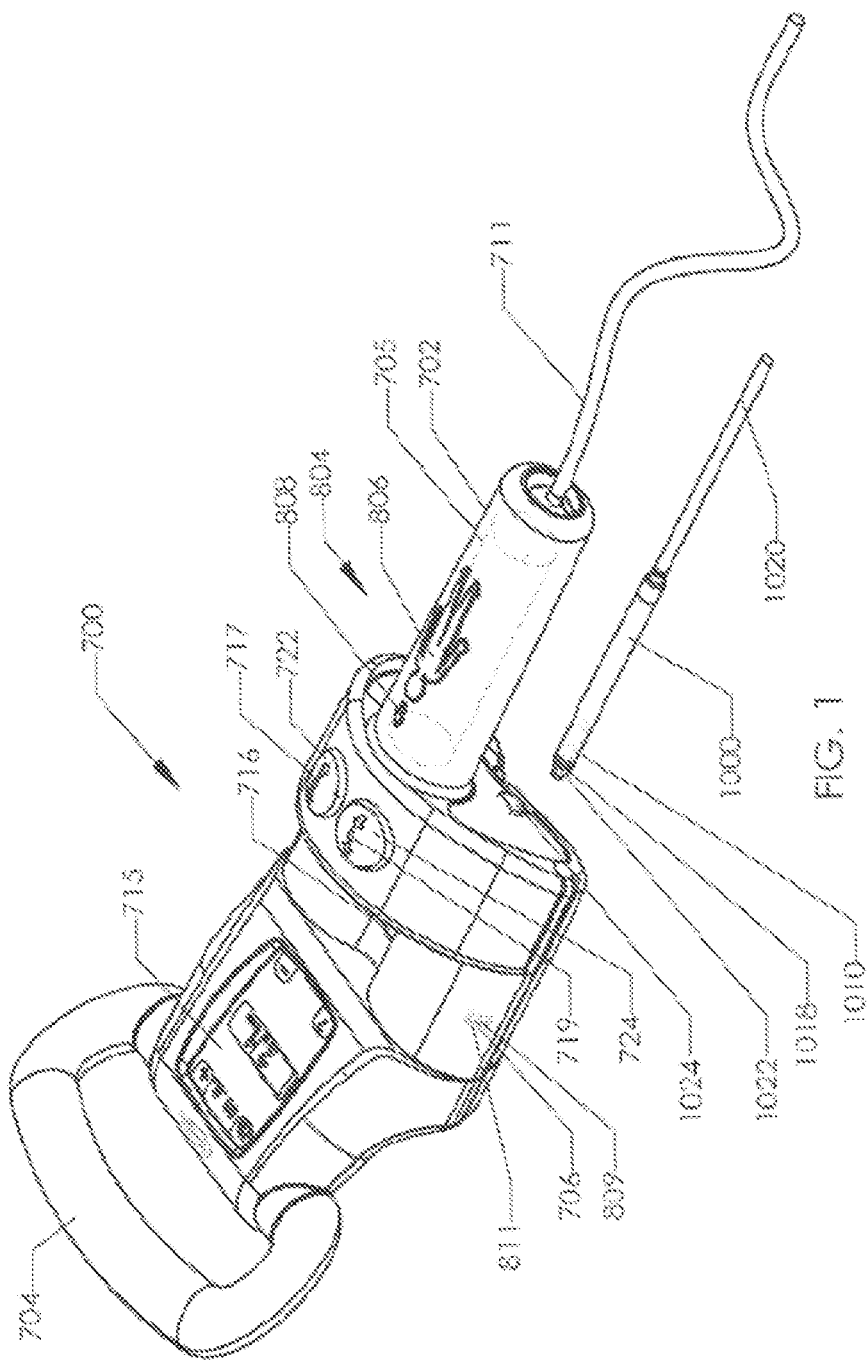
FIG. 1 illustrates an external adjustment device configured to operate a distraction device.
Figure 2:
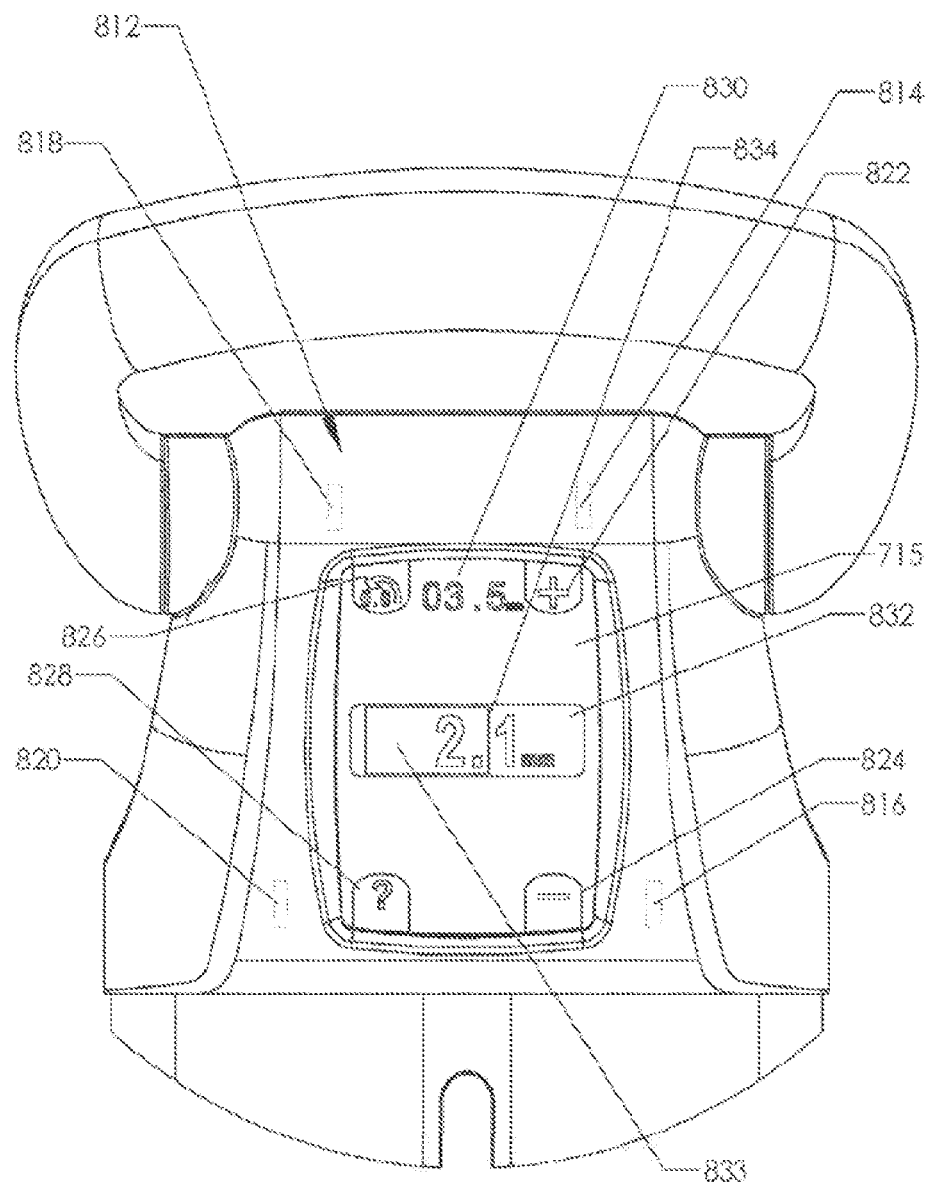
FIG. 2 illustrates a detailed view of the display and control panel of the external adjustment device.
Figure 3:
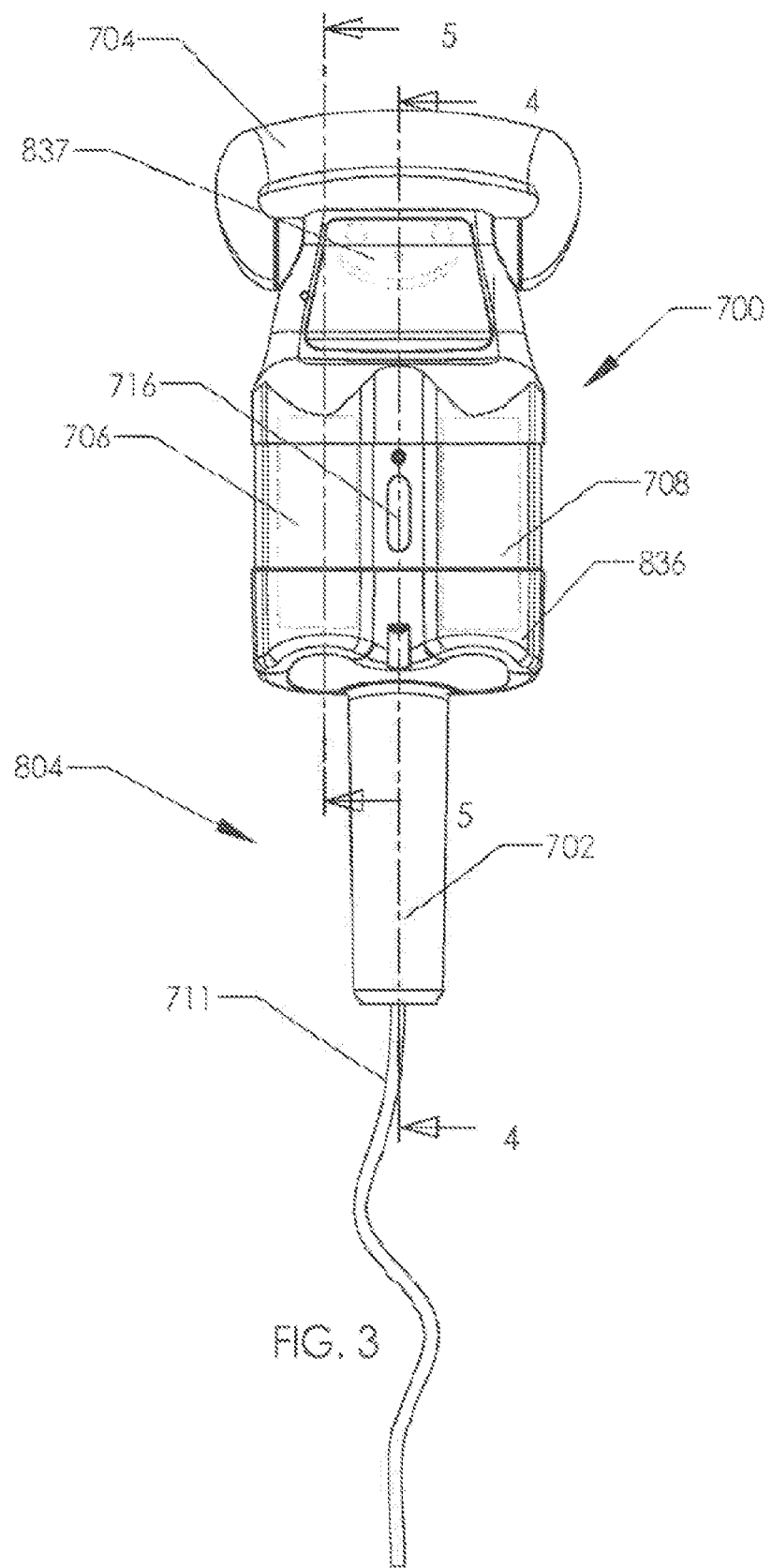
FIG. 3 illustrates the lower or underside surfaces of the external adjustment device.

FIGS. 1-3 illustrate an external adjustment device 700 that is configured for adjusting a distraction device 1000. The distraction device 1000 may include any number of distraction devices such as those disclosed in U.S. patent application Ser. Nos. 12/121,355, 12/250,442, 12/391,109, 11/172,678 which are incorporated by reference herein. The distraction device 1000 generally includes a rotationally mounted, internal permanent magnet 1010 that rotates in response to the magnetic field applied by the external adjustment device 700. Rotation of the magnet 1010 in one direction effectuates distraction while rotation of the magnet 1010 in the opposing direction effectuates retraction. External adjustment device 700 may be powered by a rechargeable battery or by a power cord 711. The external adjustment device 700 includes a first handle 702 and a second handle 704. The second handle 704 is in a looped shape, and can be used to carry the external adjustment device 700. The second handle 704 can also be used to steady the external adjustment device 700 during use. Generally, the first handle 702 extends linearly from a first end of the external adjustment device 700 while the second handle 704 is located at a second end of the external adjustment device 700 and extends substantially off axis or is angled with respect to the first handle 702. In one embodiment, the second handle 704 may be oriented substantially perpendicular relative to the first handle 702 although other The first handle 702 contains the motor 705 that drives a first external magnet 706 and a second external magnet 708 as best seen in FIG. 3, via gearing, belts and the like. On the first handle 702 is an optional orientation image 804 comprising a body outline 806 and an optional orientation arrow 808 that shows the correct direction to place the external adjustment device 700 on the patient's body, so that the distraction device is operated in the correct direction. While holding the first handle 702, the operator presses with his thumb the distraction button 722, which has a distraction symbol 717, and is a first color, for example green. This distracts the distraction device 1000. If the distraction device 1000 is over-distracted and it is desired to retract, or to lessen the distraction of the device 1000, the operator presses with his thumb the retraction button 724 which has a retraction symbol 719.

Distraction turns the magnets 706, 708 one direction and retraction turns the magnets 706, 708 in the opposite direction. Magnets 706, 708 have stripes 809 that can be seen in window 811. This allows easy identification of whether the magnets 706, 708 are stationary or turning, and in which direction they are turning. This allows quick trouble shooting by the operator of the device. The operator can determine the point on the patient where the magnet of the distraction device 1000 is implanted, and can then put the external adjustment device 700 in correct location with respect to the distraction device 1000, by marking the corresponding portion of the skin of the patient, and then viewing this spot through the alignment window 716 of the external adjustment device 700.

A control panel 812 includes several buttons 814, 816, 818, 820 and a display 715. The buttons 814, 816, 818, 820 are soft keys, and able to be programmed for an array of different functions. In one configuration, the buttons 814, 816, 818, 820 have corresponding legends which appear in the display. To set the length of distraction to be performed on the distraction device 1000, the target distraction length 830 is adjusted using an increase button 814 and a decrease button 816, The legend with a green plus sign graphic 822 corresponds to the increase button 814 and the legend with a red negative sign graphic 824 corresponds to the decrease button 816. It should be understood that mention herein to a specific color used for a particular feature should be viewed as illustrative. Other colors besides those specifically recited herein may be used in connection with the inventive concepts described herein. Each time the increase button 814 is depressed, it causes the target distraction length 830 to increase 0.1 mm. Each time the decrease button 816 is depressed it causes the target distraction length 830 to decrease 0.1 mm. Of course, other decrements besides 0.1 mm could also be used. When the desired target distraction length 830 is displayed, and the external adjustment device 700 is correctly placed on the patient, the operator then holds down the distraction button 722 and the External Distraction Device 700 operates, turning the magnets 706, 708, until the target distraction length 830 is achieved. Following this, the external adjustment device 700 stops. During the distraction process, the actual distraction length 832 is displayed, starting at 0.0 mm and increasing until the target distraction length 830 is achieved. As the actual distraction length 832 increases, a distraction progress graphic 834 is displayed. For example a light colored box 833 that fills with a dark color from the left to the right. In FIG. 2, the target distraction length 830 is 3.5 mm, and 2.1 mm of distraction has occurred. 60% of the box 833 of the distraction progress graphic 834 is displayed. A reset button 818 corresponding to a reset graphic 826 can be pressed to reset one or both of the numbers back to zero. An additional button 820 can be assigned for other functions (help, data, etc.). This button can have its own corresponding graphic 828. Alternatively, a touch screen can be used, for example capacitive or resistive touch keys. In this embodiment, the graphics/legends 822, 824, 826, 828 may also be touch keys, replacing or augmenting the buttons 814, 816, 818, 820. In one particular embodiment, touch keys at 822, 824, 826, 828 perform the functions of buttons 814, 816, 818, 820 respectively, and the buttons 814, 816, 818, 820 are eliminated.

The two handles 702, 704 can be held in several ways. For example the first handle 702 can be held with palm facing up while trying to find the location on the patient of the implanted magnet of the distraction device 1000. The fingers are wrapped around the handle 702 and the fingertips or mid-points of the four fingers press up slightly on the handle 702, balancing it somewhat. This allows a very sensitive feel that allows the magnetic field between the magnet in the distraction device 1000 and the magnets 706, 708 of the external adjustment device 700 to be more obvious. During the distraction of the patient, the first handle 702 may be held with the palm facing down, allowing the operator to push the device down firmly onto the patient, to minimize the distance between the magnets 706, 708 of the external adjustment device and the magnet 1010 of the distraction device 1000, thus maximizing the torque coupling. This is especially appropriate if the patient is large or somewhat obese. The second handle 704 may be held with the palm up or the palm down during the magnet sensing operation and the distraction operation, depending on the preference of the operator.

FIG. 3 illustrates the underside or lower surface of the external adjustment device 700. At the bottom of the external adjustment device 700, the contact surface 836 may be made of material of a soft durometer, such as elastomeric material, for example PEBAX® or Polyurethane. This allows for anti-shock to protect the device 700 if it is dropped. Also, if placing the device on patient's bare skin, materials of this nature do not pull heat away from patient as quickly, and so they "don't feel as cold" as hard plastic or metal. The handles 702, 704 may also have similar material covering them, in order to act as non-slip grips.

FIG. 3 also illustrates child friendly graphics 837, including the option of a smiley face. Alternatively this could be an animal face, such as a teddy bear, a horsey or a bunny rabbit. A set of multiple faces can be removable and interchangeable to match the likes of various young patients. In addition, the location of the faces on the underside of the device, allows the operator to show the faces to a younger child, but keep it hidden from an older child, who may not be so amused. Alternatively, sock puppets or decorative covers featuring human, animal or other characters may be produced so that the device may be thinly covered with them, without affecting the operation of the device, but additionally, the puppets or covers may be given to the young patient after a distraction procedure is performed. It is expected that this can help keep a young child more interested in returning to future procedures.

Figures 4, 5:
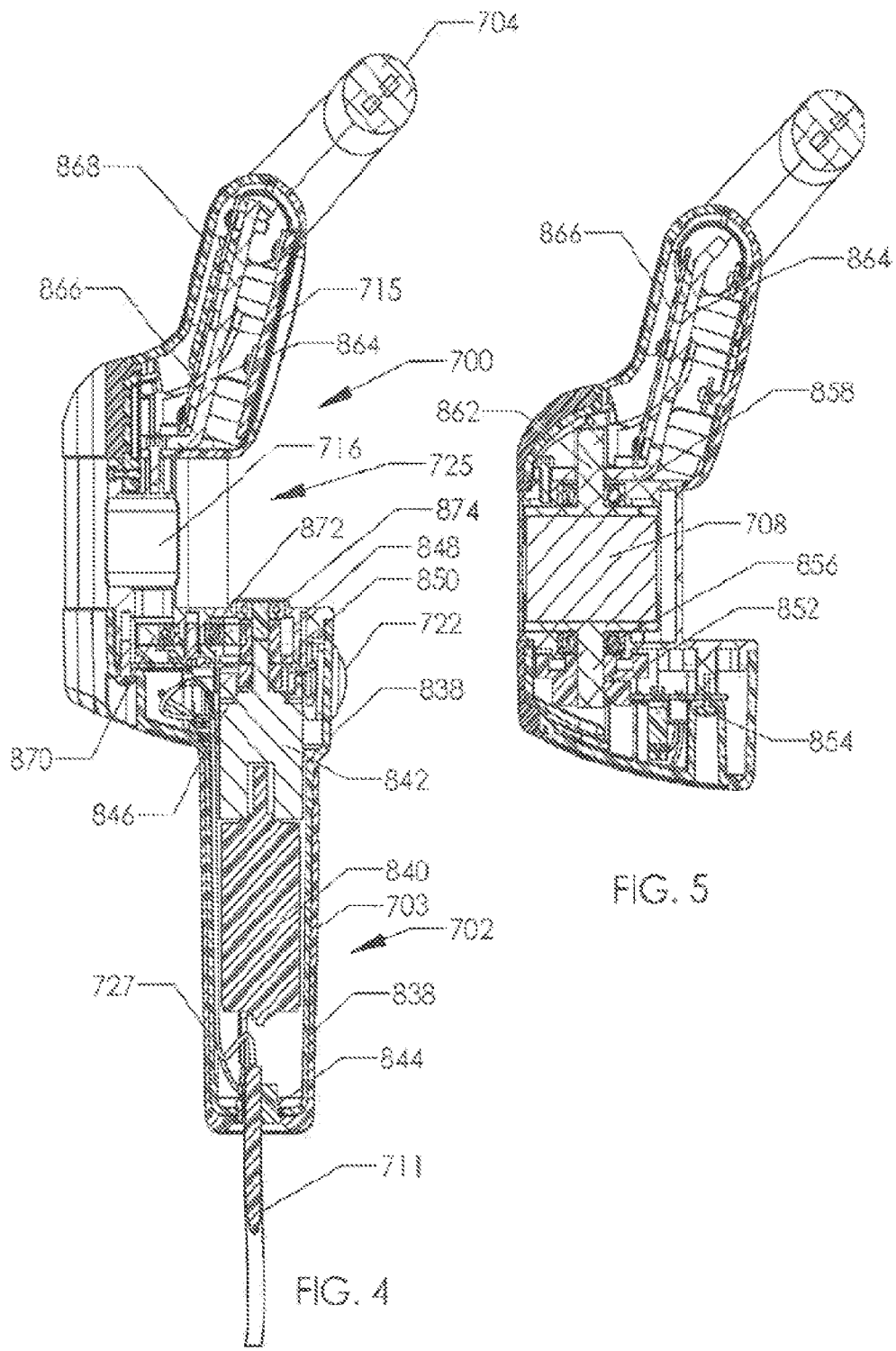
FIG. 4 illustrates a sectional view of the external adjustment device taken along line 4-4 of FIG. 3.
FIG. 5 illustrates a sectional view of the external adjustment device taken along line 5-5 of FIG. 3.

FIGS. 4 and 5 are sectional views that illustrate the internal components of the external adjustment device 700 taken along various centerlines. FIG. 4 is a sectional view of the external adjustment device 700 taken along the line 4-4 of FIG. 3. FIG. 5 is a sectional view of the external adjustment device 700 taken along the line 5-5 of FIG. 3. The external adjustment device 700 comprises a first housing 868, a second housing 838 and a central magnet section 725. First handle 702 and second handle 704 include grip 703 (shown on first handle 702). Grip 703 may be made of an elastomeric material and may have a soft feel when gripped by the hand. The material may also have a tacky feel, in order to aid firm gripping. Power is supplied via power cord 711, which is held to second housing 838 with a strain relief 844. Wires 727 connect various electronic components including motor 840 which rotates magnets 706, 708 via gear box 842, output gear 848, center gear 870 respectively, center gear 870 rotating two magnet gears 852, one on each magnet 706, 708 (one such gear 852 is illustrated in FIG. 5). Output gear 848 is attached to motor output via coupling 850, and both motor 840 and output gear 848 are secured to second housing 838 via mount 846. Magnets 706, 708 are held within magnet cups 862. Magnets and gears are attached to bearings 872, 874, 856, 858, which aid in low friction rotation. Motor 840 is controlled by motor printed circuit board (PCB) 854, while the display is controlled by display printed circuit board (PCB) 866 (FIG. 4). Display PCB 866 is attached to frame 864.

Figure 6:
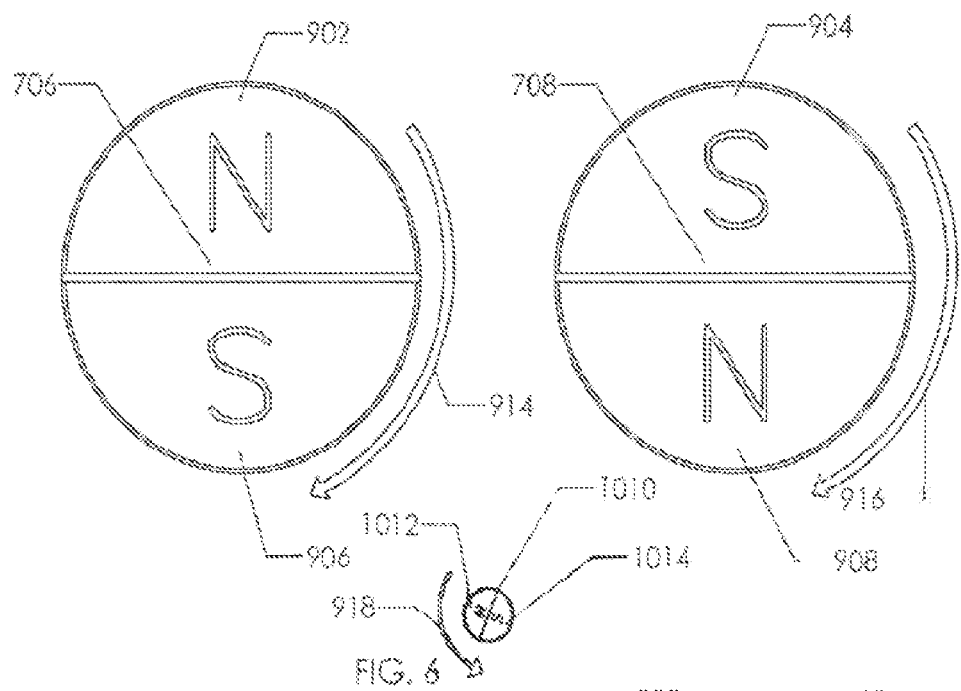
FIG. 6 schematically illustrates the orientation of the magnets of the external adjustment device while driving an implanted magnet of a distraction device.
Figure 7:
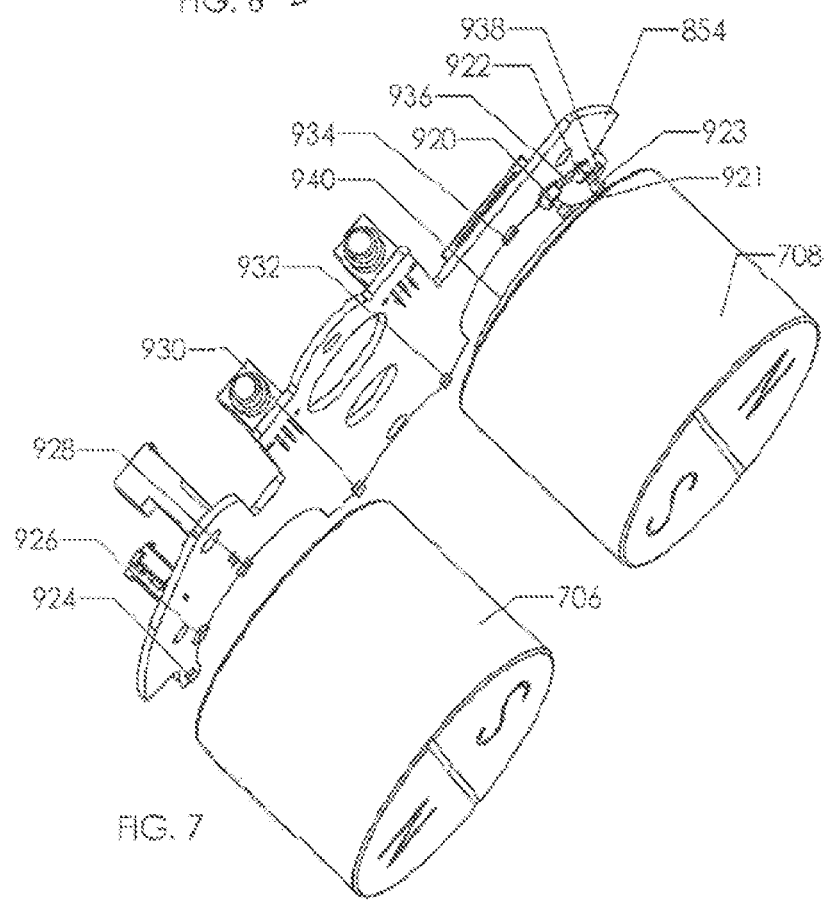
FIG. 7 illustrates various sensors connected to a printed circuit board of the external adjustment device.

FIG. 6 illustrates the orientation of poles of the first and second external magnets 706, 708 and the implanted magnet 1010 of the distraction device 1000 during a distraction procedure. For the sake of description, the orientations will be described in relation to the numbers on a clock. First external magnet 706 is turned (by gearing, belts, etc.) synchronously with second external magnet 708 so that north pole 902 of first external magnet 706 is pointing in the twelve o'clock position when the south pole 904 of the second external magnet 708 is pointing in the twelve o'clock position. At this orientation, therefore, the south pole 906 of the first external magnet 706 is pointing is pointing in the six o'clock position while the north pole 908 of the second external magnet 708 is pointing in the six o'clock position. Both first external magnet 706 and second external magnet 708 are turned in a first direction as illustrated by respective arrows 914, 916. The rotating magnetic fields apply a torque on the implanted magnet 1010, causing it to rotate in a second direction as illustrated by arrow 918. Exemplary orientation of the north pole 1012 and south pole 1014 of the implanted magnet 1010 during torque delivery are shown in FIG. 6. When the first and second external magnets 706, 708 are turned in the opposite direction from that shown, the implanted magnet 1010 will be turned in the opposite direction from that shown. The orientation of the first external magnet 706 and the second external magnet 708 in relation to each other serves to optimize the torque delivery to the implanted magnet 1010. During operation of the external adjustment device 700, it is often difficult to confirm that the two external magnets 706, 708 are being synchronously driven as desired. Turning to FIGS. 7 and 8, in order to ensure that the external adjustment device 700 is working properly, the motor printed circuit board 854 comprises one or more encoder systems, for example photointerrupters 920, 922 and/or Hall effect sensors 924, 926, 928, 930, 932, 934, 936, 938. Photointerrupters 920, 922 each comprise an emitter and a detector. A radially striped ring 940 may be attached to one or both of the external magnets 706, 708 allowing the photointerrupters to optically encode angular motion. Light 921, 923 is schematically illustrated between the radially striped ring 940 and photointerrupters 920, 922.

Independently, Hall effect sensors 924, 926, 928, 930, 932, 934, 936, 938 may be used as non-optical encoders to track rotation of one or both of the external magnets 706, 708. While eight (8) such Hall effect sensors are illustrated in FIG. 7 it should be understood that fewer or more such sensors may be employed. The Hall effect sensors are connected to the motor printed circuit board 854 at locations that allow the Hall effect sensors to sense the magnetic field changes as the external magnets 706, 708 rotate. Each Hall effect sensor 924, 926, 928, 930, 932, 934, 936, 938 outputs a voltage that corresponds to increases or decreases in the magnetic field. FIG. 9A indicates one basic arrangement of Hall effect sensors relative to sensors 924, 938. A first Hall effect sensor 924 is located at nine o'clock in relation to first external magnet 706. A second Hall effect sensor 938 is located at three o'clock in relation to second external magnet 708. As the magnets 706, 708 rotate correctly in synchronous motion, the first voltage output 940 of first Hall effect sensor 924 and second voltage output 942 of second Hall effect sensor have the same pattern, as seen in FIG. 9B, which graphs voltage for a full rotation cycle of the external magnets 706, 708. The graph indicates a sinusoidal variance of the output voltage, but the clipped peaks are due to saturation of the signal. Even if Hall effect sensors used in the design cause this effect, there is still enough signal to compare the first voltage output 940 and the second voltage output 942 over time. If either of the two Hall effect sensors 924, 938 does not output a sinusoidal signal during the operation or the external adjustment device 700, this demonstrates that the corresponding external magnet has stopped rotating, for example due to adhesive failure, gear disengagement, etc. FIG. 9C illustrates a condition in which both the external magnets 706, 708 are rotating at the same approximate angular speed, but the north poles 902, 908 are not correctly synchronized. Because of this, the first voltage output 940 and second voltage output 942 are now out-of-phase, and exhibit a phase shift (θ). These signals are processed by a processor 915 and an error warning is displayed on the display 715 of the external adjustment device 700 so that the device may be resynchronized.

If independent stepper motors are used, the resynchronization process may simply be one of reprogramming, but if the two external magnets 706, 708 are coupled together, by gearing or belt for example, then a mechanical rework may be required. An alternative to the Hall effect sensor configuration of FIG. 9A is illustrated in FIG. 10A. In this embodiment, a third Hall effect sensor 928 is located at twelve o'clock in relation to the first external magnet 706 and a fourth Hall effect sensor 934 is located at twelve o'clock in relation to the second external magnet 708. With this configuration, the north pole 902 of the first external magnet 706 should be pointing towards the third Hall effect sensor 928 when the south pole 904 of the second external magnet 708 is pointing towards the fourth Hall effect sensor 934. With this arrangement, the third Hall effect sensor 928 outputs a third output voltage 944 and the fourth Hall effect sensor 934 outputs a fourth output voltage 946 (FIG. 10B). The third output voltage 944 is by design out of phase with the fourth output voltage 946. An advantage of the Hall effect sensor configuration of FIG. 9A is that the each sensor has a larger distance between it and the opposite magnet, for example first Hall effect sensor 924 in comparison to second external magnet 708, so that there is less possibility of interference. An advantage to the Hall effect sensor configuration of FIG. 10A is that it may be possible to make a more compact external adjustment device 700 (less width). The out-of-phase pattern of FIG. 10B can also be analyzed to confirm magnet synchronicity.

Returning to FIGS. 7 and 8, additional Hall effect sensors 926, 930, 932, 936 are shown. These additional sensors allow additional precision to the rotation angle feedback of the external magnets 706, 708 of the external adjustment device 700. Again, the particular number and orientation of Hall effect sensors may vary. In place of the Hall effect sensors, magnetoresistive encoders may also be used.

In still another embodiment, additional information may be processed by processor 915 and may be displayed on display 715. For example, distractions using the external adjustment device 700 may be performed in a doctor's office by medical personnel, or by patients or members of patient's family in the home. In either case, it may be desirable to store information from each distraction session that can be accessed later. For example, the exact date and time of each distraction, and the amount of distraction attempted and the amount of distraction obtained. This information may be stored in the processor 915 or in one or more memory modules (not shown) associated with the processor 915. In addition, the physician may be able to input distraction length limits, for example the maximum amount that can be distracted at each session, the maximum amount per day, the maximum amount per week, etc. The physician may input these limits by using a secure entry using the keys or buttons of the device, that the patient will not be able to access.

Returning to FIG. 1, in some patients, it may be desired to place a first end 1018 of the distraction device 1000 proximally in the patient, or towards the head, and second end 1020 of the distraction device 1000 distally, or towards the feet. This orientation of the distraction device 1000 may be termed antegrade. In other patients, it may be desired to orient the distraction device 1000 with the second end 1020 proximally in the patient and the first end 1018 distally. In this case, the orientation of the distraction device 1000 may be termed retrograde. In a distraction device 1000 in which the magnet 1010 rotates in order to turn a screw within a nut, the orientation of the distraction device 1000 being either antegrade or retrograde in patient could mean that the external adjustment device 700 would have to be placed in accordance with the orientation image 804 when the distraction device 1000 is placed antegrade, but placed the opposite of the orientation image 804 when the distraction device 1000 is placed retrograde. Alternatively, software may be programmed so that the processor 915 recognizes whether the distraction device 1000 has been implanted antegrade or retrograde, and then turns the magnets 706, 708 in the appropriate direction when the distraction button 722 is placed.

For example, the motor 705 would be commanded to rotate the magnets 706, 708 in a first direction when distracting an antegrade placed distraction device 1000, and in a second, opposite direction when distracting a retrograde placed distraction device 1000. The physician may, for example, be prompted by the display 715 to input using the control panel 812 whether the distraction device 1000 was placed antegrade or retrograde. The patient may then continue to use the same external adjustment device 700 to assure that the motor 705 turns the magnets 706, 708 in the proper directions for both distraction and retraction. Alternatively, the distraction device may incorporate an RFID chip 1022 which can be read and written to by an antenna 1024 on the external adjustment device 700. The position of the distraction device 1000 in the patient (antegrade or retrograde) is written to the RFID chip 1022, and can thus be read by the antenna 1024 of any external adjustment device 700, allowing the patient to get correct distractions or retractions, regardless of which external adjustment device 700 is used.

Figure 11:
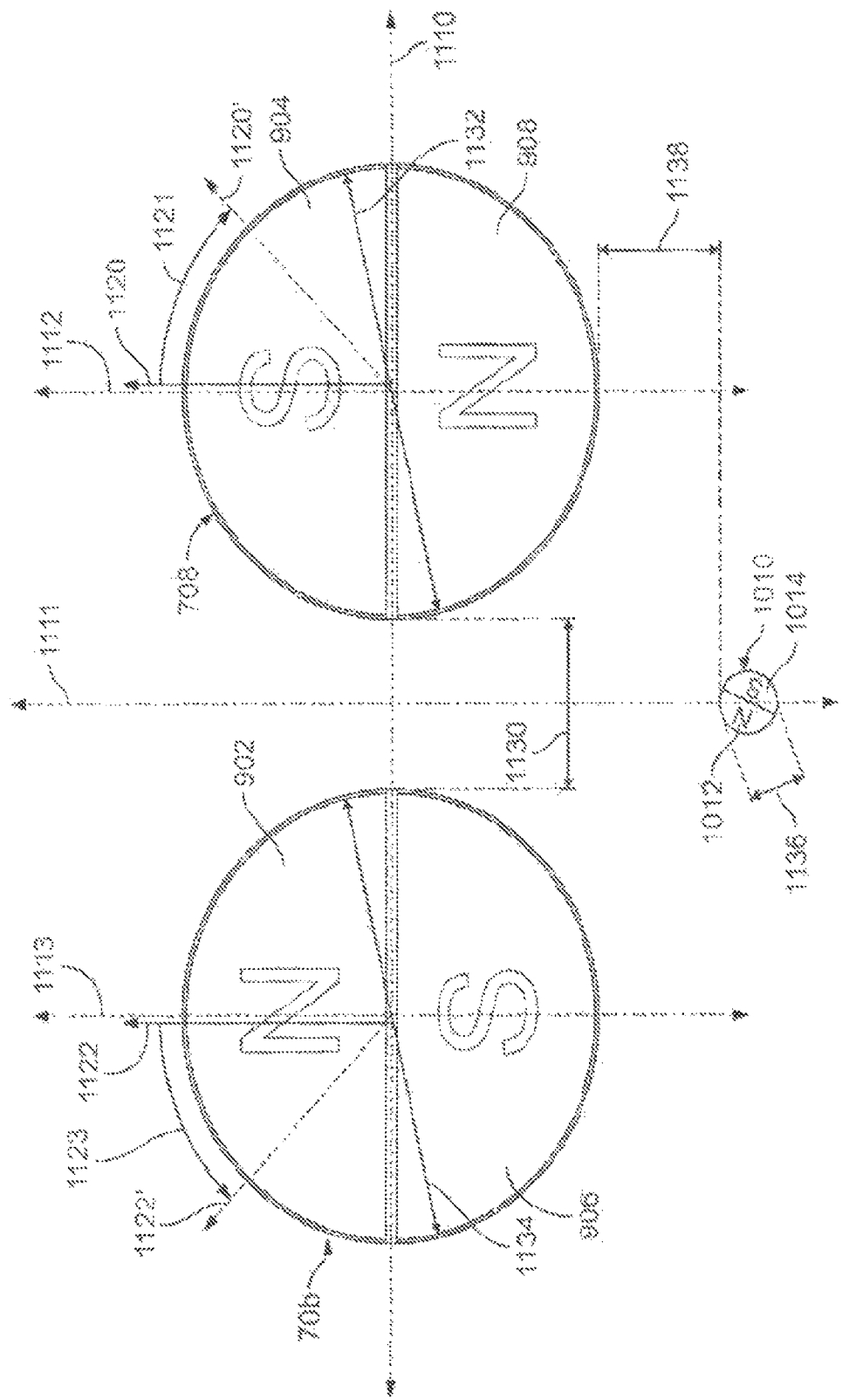
FIG. 11 illustrates the orientation of two external magnets of an external adjustment device in relation to an internal, implanted magnet.

FIG. 11 illustrates the orientation of the poles of two external magnets, the first external magnet 706 and the second external magnet 708 of an external adjustment device in relation to an internal, implanted magnet 1010, for example, in an implanted distraction device. As with FIG. 6, above, the orientations of each magnet may be described in relation to the numbers on a clock. First external magnet 706 has a north pole 902 and a south pole 906. In the same way, second external magnet 708 has a south pole 904 and a north pole 908. Each external magnet is physically defined by a diameter and a length (i.e., to form a substantially right cylinder): the first external magnet 706 has a first magnet diameter 1134 while the second external magnet 708 has a second magnet diameter 1132. In some embodiments, the first magnet diameter 1134 and the second magnet diameter 1132 are equal. However, this need not always be the case. In other embodiments, the first magnet diameter 1134 is larger than the second magnet diameter 1132. And in still other embodiments the second magnet diameter 1132 is larger than the first magnet diameter 1134.

FIG. 11 is included primarily to illustrate the first external magnet 706 and the second external magnet 708—implanted magnet 1010 is included mainly for reference. However, in much the same way as the first external magnet 706 and the second external magnet 708, the implanted magnet 1010 has a north pole 1012 and a south pole 1014. The implanted magnet 1010, too, may be defined by an internal magnet diameter 1136 and a length (i.e., the implanted magnet 1010 may be a substantially right cylinder as well). It should be understood that any of the first external magnet 706, second external magnet 708, and implanted magnet 1010 may be magnets other than substantially right cylinders.

As explained above, with respect to FIG. 6, external magnet 706 is configured to rotate about a first elongate rotational axis. In FIGS. 6 and 11, the first elongate rotational axis is a line through the center of the first external magnet 706 extending into the page through the center of the first external magnet 706. Likewise, the second external magnet 708 is configured to rotate about a second elongate rotational axis. Again, in FIGS. 6 and 11, the second elongate rotational axis is a line through the center of the second external magnet 708 extending into the page through the center of the second external magnet 708. As the first elongate rotational axis and the second elongate rotational axis are essentially points, the two define a line between the first external magnet 706 and the second external magnet 708. The line on which they lie is shown in FIG. 11 as horizontal axis 1110.

Each of the first external magnet 706 and second external magnet 708 defines its own vertical axis, perpendicular to the horizontal axis 1110 and through the magnet's elongate rotational axis. First external magnet 706 has a first magnet vertical axis 1113 that is perpendicular to the horizontal axis 1110 and intersects the first elongate rotational axis (i.e., the horizontal axis 1110 and the first magnet vertical axis 1113 intersect at the center of the circle defined by any plane perpendicular to the longitudinal axis of the first external magnet 706). In the same way, second external magnet 708 has a second magnet vertical axis 1112 that is perpendicular to the horizontal axis 1110 and intersects the second elongate rotational axis (i.e., the horizontal axis 1110 and the second magnet vertical axis 1112 intersect at the center of the circle defined by any plane perpendicular to the longitudinal axis of the second external magnet 708).

The first external magnet 706 and the second external magnet 708 are separated by an intermagnet gap 1130, which is defined as the distance along the horizontal axis 1110 between the rightmost edge of the first external magnet 706 and the leftmost edge of the second external magnet 708. A central vertical axis 1111 bisects the horizontal axis 1110 in the center of the intermagnet gap 1130, perpendicular to the horizontal axis 1110. Therefore, the distance from the center of the first external magnet 706 (i.e., the first elongate rotational axis) to the center of the second external magnet 708 (i.e., the second elongate rotational axis) is equal to one half the first magnet diameter 1134 plus one half the second magnet diameter 1132 plus the intermagnet gap 1130. When the first magnet diameter 1134 of the first external magnet 706 and second magnet diameter 1132 of the second external magnet 708 are equal, as shown in FIG. 11, the first elongate rotational axis and the second elongate rotational axis are equidistant from the central vertical axis 1111. However, while some embodiments include equally sized first external magnet 706 and second external magnet 708, not all do. Therefore, not all possible pairs of first elongate rotational axis and second elongate rotational axis are equidistant from the central vertical axis 1111.

An ideal reference location for the implanted magnet 1010 is on the central vertical axis 1111. In the case where first magnet diameter 1134 and second magnet diameter 1132 are equal, the first external magnet 706 and second external magnet 708 create equal magnetic fields. Therefore, any point along central vertical axis 1111 will experience equal effects by first external magnet 706 and second external magnet 708. The distance between the lowermost edge of the external magnets (i.e., first external magnet 706 and second external magnet 708) and the uppermost edge of the implanted magnet 1010 is defined as the gap distance 1138. It should be understood that, while a reference location for the implanted magnet 1010 on the central vertical axis 1111 is conceptually helpful, the implanted magnet 1010 may also lie off the central vertical axis 1111.

Figure 12A:
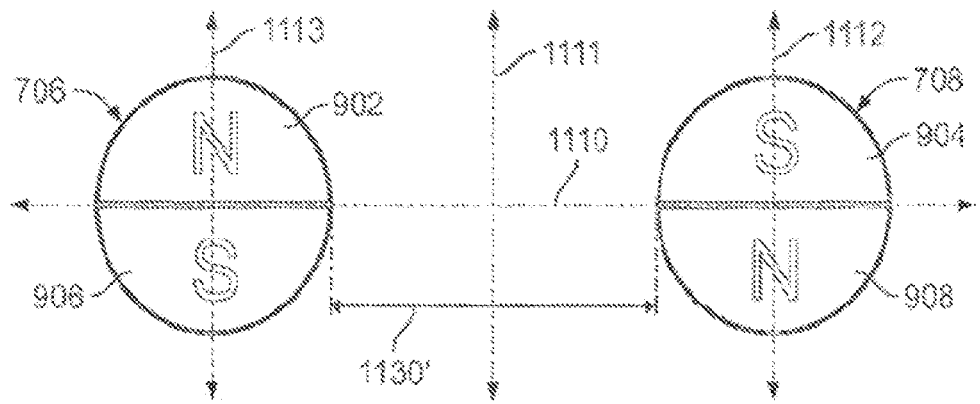
FIGS. 12A-12C illustrate pairs of external magnets of an external adjustment device having different intermagnet gaps.
Figure 12B:
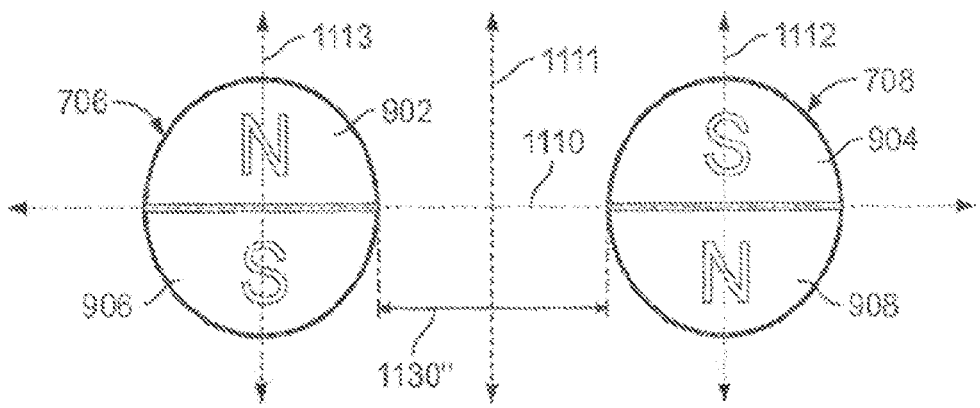
Figure 12C:
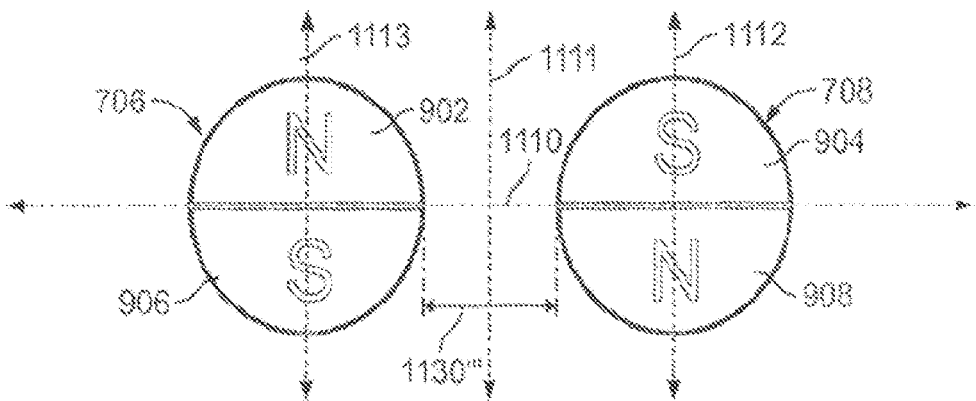

Turning to FIGS. 12A-12C, a series of external magnet pairs is shown with varying intermagnet gaps 1130. FIG. 12A shows a first external magnet 706 and second external magnet 708 that both lie on a horizontal axis 1110 separated by a first example intermagnet gap 1130'. FIG. 12B shows a first external magnet 706 and a second external magnet 708 that both lie on a horizontal axis 1110 separated by a second example intermagnet gap 1130". The second example intermagnet gap 1130" of FIG. 12B is generally smaller than the first example intermagnet gap 1130' of FIG. 12A. FIG. 12C shows a first external magnet 706 and a second external magnet 708 that both lie on a horizontal axis 1110 separated by a third example intermagnet gap 1130'. The third example intermagnet gap 1130''' is generally smaller than both the second example intermagnet gap 1130" and the first example intermagnet gap 1130'. It should be understood that any intermagnet gap 1130 may be used between the first external magnet 706 and second external magnet 708.

Figure 13A:
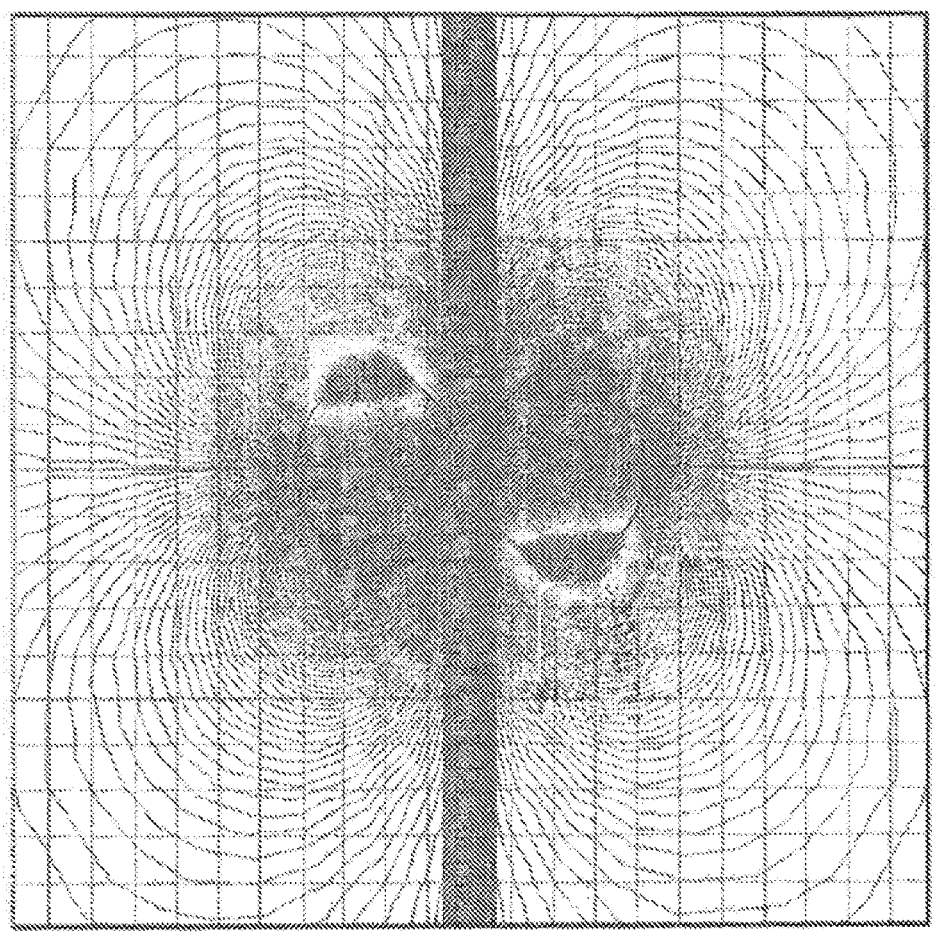
FIGS. 13A-13B illustrate schematics of magnetic field lines surrounding external magnets of an external adjustment device.
Figure 13B:
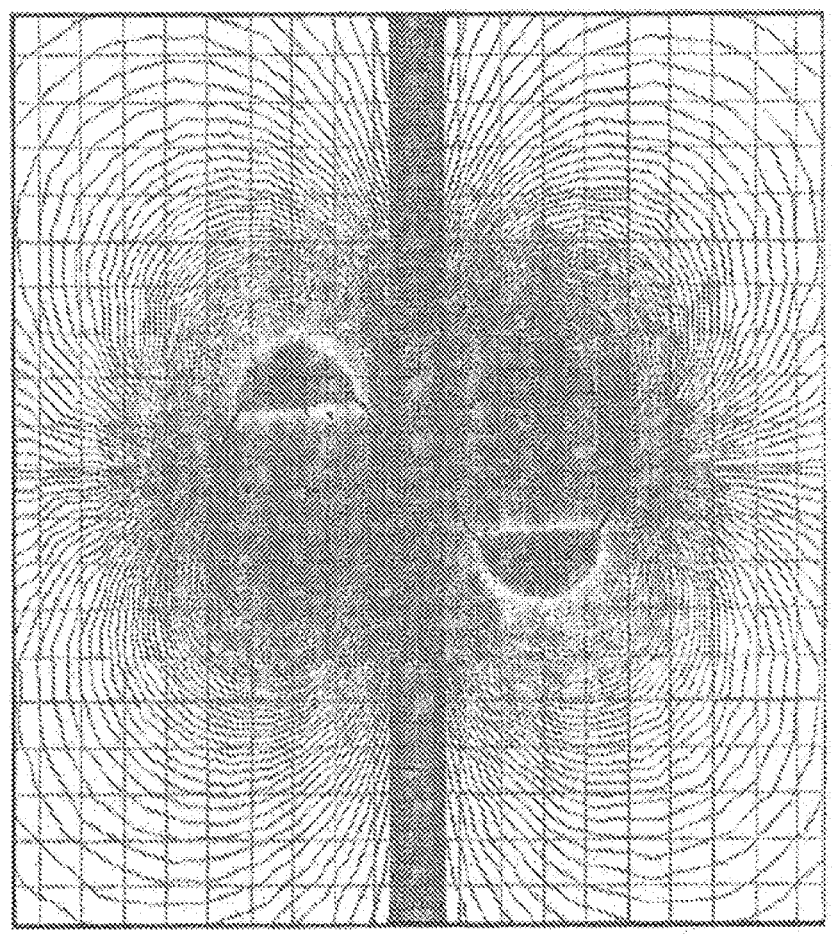

The intermagnet gap 1130 can have an effect on the magnetic flux density observed along the central vertical axis 1111. Magnetic flux density drops off at approximately 1/r3 (an inverse cube). Therefore, a very small gap distance may observe relatively high flux densities along the central vertical axis 1111. By contrast, because of how quickly the flux density drops off, a lower limit of flux density is reached relatively quickly with medium and large intermagnet gaps 1130. FIG. 13A illustrates a schematic of the magnetic field lines surrounding a first external magnet 706 and second external magnet 708. The intermagnet gap 1130 between the first external magnet 706 and second external magnet 708 is comparatively small. It can be seen that the flux lines along the central vertical axis 1111 are relatively dense, particularly along the central vertical axis 1111 near, and/or between, the first external magnet 706 and second external magnet 708. By contrast, FIG. 13B illustrates a schematic of the magnetic field lines surrounding a first external magnet 706 and second external magnet 708 separated by a intermagnet gap 1130 significantly larger than that shown in FIG. 13A. The flux lines along the central vertical axis 1111 of FIG. 13B are noticeably less dense than the flux lines along the central vertical axis 1111 of FIG. 13A. That is due, solely, to an increase in the intermagnet gap 1130.

Figure 14:
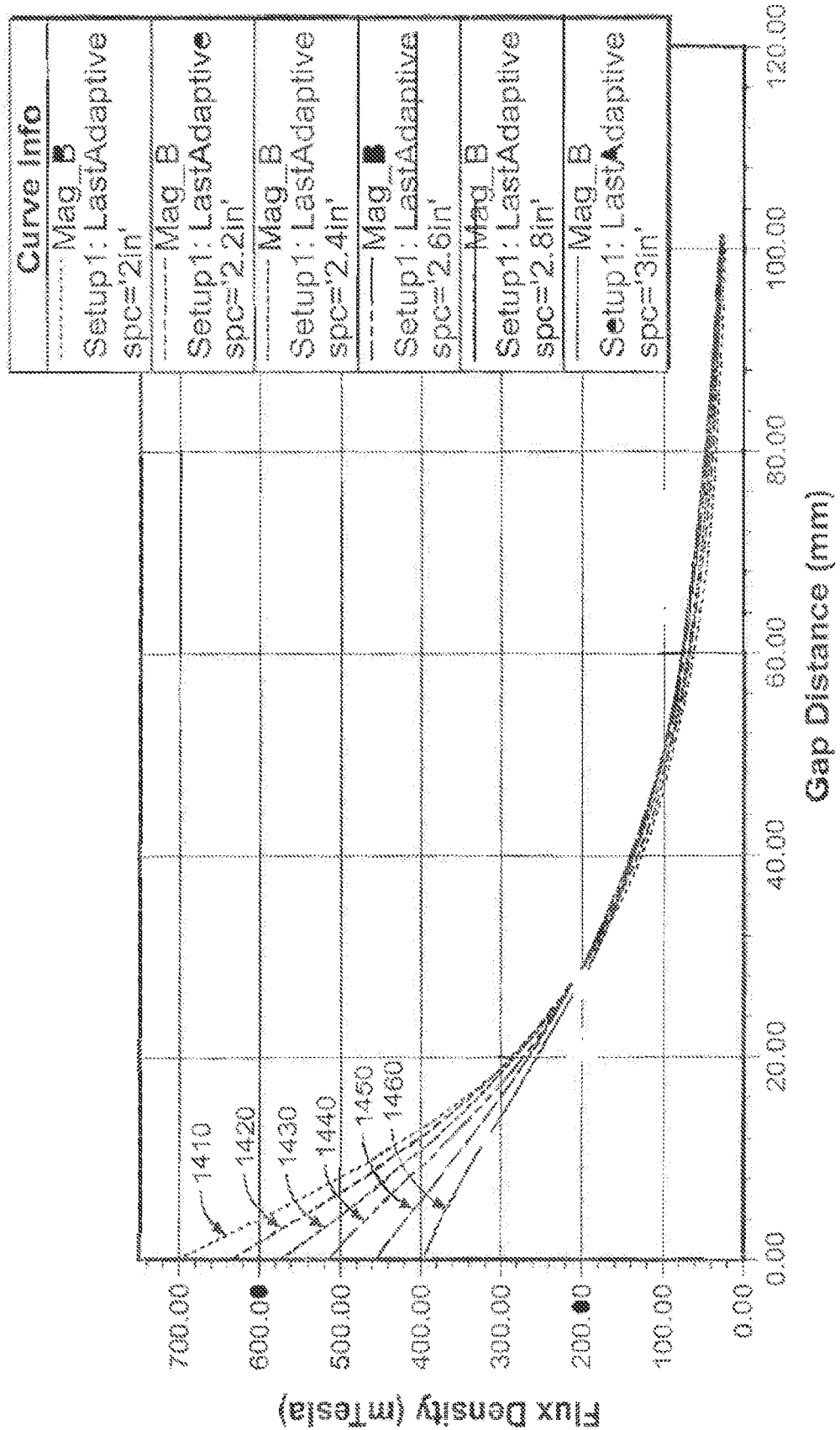
FIG. 14 illustrates a graph of magnetic flux density plotted against gap distance for two external magnets having various intermagnet gaps.

FIG. 14 illustrates a graph of magnetic flux density generated by a first external magnet 706 and a second external magnet 708 versus gap distance 1138. The modeled flux density is measured at a reference point along the central vertical axis 1111 as the reference point moves further away from the bottom of the first external magnet 706 and second external magnet 708 (i.e., as the gap distance 1138 increases from a zero reference point). FIG. 14's first line 1410 illustrates a graph of magnetic flux density versus gap distance 1138 for a first external magnet 706 and second external magnet 708 having a intermagnet gap 1130 of 50.8 mm (i.e., 2 inches). Second line 1420 illustrates a graph of magnetic flux density versus gap distance 1138 for a first external magnet 706 and second external magnet 708 having an intermagnet gap 1130 of 55.88 mm (i.e., 2.2 inches). Third line 1430 illustrates a graph of magnetic flux density versus gap distance 1138 for a first external magnet 706 and second external magnet 708 having an intermagnet gap 1130 of 60.96 mm (i.e., 2.4 inches). Fourth line 1440 illustrates a graph of magnetic flux density versus gap distance 1138 for a first external magnet 706 and second external magnet 708 having an intermagnet gap 1130 of 66.04 mm (i.e., 2.6 inches). Fifth line 1450 illustrates a graph of magnetic flux density versus gap distance 1138 for a first external magnet 706 and second external magnet 708 having an intermagnet gap 1130 of 71.12 mm (i.e., 2.8 inches). And, finally, sixth line 1460 illustrates a graph of magnetic flux density versus gap distance 1138 for a first external magnet 706 and second external magnet 708 having an intermagnet gap 1130 of 76.2 mm (i.e., 3.0 inches). FIG. 14's lines illustrate that at small gap distances 1138 (e.g., zero gap distances 1138), decreasing the intermagnet gap 1130 increases the observed flux density. In fact, at a gap distance 1138 of zero, an intermagnet gap 1130 of 50.8 mm has a flux density about 135% higher than an intermagnet gap 1130 of 76.2 mm at the same gap distance. However, the gains realized by decreasing the intermagnet gap 1130 exist only at fairly small gap distances 1138. FIG. 14's lines illustrate near convergence of the first line 1410, second line 1420, third line 1430, fourth line 1440, fifth line 1450, and sixth line 1460 at approximately 25 mm. After about 25 mm, there is little difference between the flux densities along central vertical axis 1111 for varying intermagnet gaps 1130.

Turning again to FIG. 12A-12C, in view of FIG. 14's lines, it can be seen that for small gap distances, the system illustrated in FIG. 12A having a larger first example intermagnet gap 1130' will have a smaller flux density than the system illustrated in FIG. 12B having a smaller second example intermagnet gap 1130" which will, in turn, have a smaller flux density than the system illustrated in FIG. 12C having the smallest third example intermagnet gap 1130'''. In some circumstances, a large magnetic flux density is desirable. However, in other circumstances, diminished magnetic flux densities are desirable. The desirability of varying magnetic flux densities will be discussed in additional detail, below.

As can be seen, in applications for which a small gap distance is possible or required, intermagnet gap may be varied to increase or decrease the flux density. If higher flux densities are useful or required (such as when higher torques are useful or required), the intermagnet gap may be decreased while holding the gap distance constant—i.e., first external magnet 706 and the second external magnet 708 may be brought closer together on horizontal axis 1110. By contrast, if lower flux densities are useful or required (such as when high torques are not needed or could be detrimental), the intermagnet gap may be increased while holding the gap distance constant—i.e., the first external magnet 706 and the second external magnet 708 may be moved apart on the horizontal axis 1110. Of course, both intermagnet gap and gap distance may be varied.

In some embodiments, the external adjustment device 700 may be "smart" and able to vary the intermagnet gap based one or more factors, such as, but not limited to, user input and a sensed parameter. Therefore, such a "smart" external adjustment device 700 may manipulate intermagnet gap to increase or decrease the flux density as needed. For example, a user may input several parameters that allow the external adjustment device to select the appropriate intermagnet gap distance for the given application. Such variable may include implant location, patient age, patient weight, patient body mass index (BMI), gap distance, etc. By contrast to input parameters, a "smart" external adjustment device 700 may be able to use sensed parameters such as gap distance magnetic coupling slippage, torque generated, force generated, etc.

In response to one or more of these user inputs and sensed parameters, the intermagnet gap may be adjusted. In some embodiments, the external adjustment device 700 may inform a user that a given adjustment could improve treatment efficacy. In such a case, the user could use any of a number of tools, systems, and methods to increase the intermagnet gap. Alternatively, a "smart" external adjustment device 700 may process the user inputs and/or sensed parameters, determine that a change (increase or decrease) in flux density or torque generation would be advantageous, and automatically adjust the intermagnet gap to the optimum intermagnet gap that remains within system capabilities (i.e., due to physical constraints, there are both lower and upper limits on the intermagnet gap).

As explained with reference to FIG. 6, first external magnet 706 is turned (by gearing, belts, etc.) synchronously with second external magnet 708 so that the north pole 902 of first external magnet 706 is pointing in the twelve o'clock position when the south pole 904 of the second external magnet 708 is pointing in the twelve o'clock position. At this orientation, therefore, the south pole 906 of the first external magnet 706 is pointing in the six o'clock position while the north pole 908 of the second external magnet 708 is pointing in the six o'clock position. Both first external magnet 706 and second external magnet 708 may be turned in a first direction, such as in a clockwise direction. The rotating magnetic fields apply a torque on the implanted magnet 1010, causing it to rotate in a second direction, such as in a counterclockwise direction. When the first and second external magnets 706, 708 are turned in the opposite direction, i.e., a counterclockwise direction, the implanted magnet 1010 will also be turned in the opposite direction, i.e., a clockwise direction.

FIG. 6 illustrates the reference configuration of the first external magnet 706 and the second external magnet 708. The first external magnet 706 is positioned such that the center of the north pole 902 points up and the center of the south pole 906 points down. In the same way, the second external magnet 708 is positioned such that the center of the south pole 904 points up and the center of the north pole 908 points down. Thereafter, in FIG. 6, the two magnets rotate at fixed angular positioned with respect to each other. Therefore, the north pole 902 of the first external magnet 706 and the south pole 904 of the second external magnet 708 are always at the same angular position. And, the south pole 906 of the first external magnet 706 and the north pole 908 of the second external magnet 708 are also always at the same angular position.

Turning again to FIG. 11, the first external magnet 706 has a first central magnetic axis 1122 that extends through the center of the first external magnet's 706 north pole 902, through the center of the first external magnet 706 to intersect the first elongate rotational axis, and through the center of the first external magnet's 706 south pole 906. The first central magnetic axis 1122 is discussed with respect to the orientation of the first external magnet's 706 north pole 902. In the same way, the second external magnet 708 has a second central magnetic axis 1120 that extends through the center of the second external magnet's 708 south pole 904 of the second external magnet 708, through the center of the second external magnet 708 to intersect the second elongate rotational axis, and through the center of the second external magnet's 708 north pole 908. The second central magnetic axis 1120 is discussed with respect to the orientation of the second external magnet's 708 south pole 904.

In its reference orientation, shown in both FIG. 6 and FIG. 11, the first central magnetic axis 1122 is directly aligned with the first magnet vertical axis 1113. This aligned orientation has no angular offset (i.e., the angular offset of the first external magnet 706 is 0°). Rotations of the first external magnet 706 and second external magnet 708 are referred to by reference to the location of the implanted magnet 1010. As shown in FIG. 11, in which the implanted magnet 1010 is "above" the first external magnet 706 and second external magnet 708, rotations of the first external magnet 706 about the first elongate rotational axis in a counterclockwise direction are denoted as being positive, while rotations of the first external magnet 706 about the first elongate rotational axis in a clockwise direction are denoted as being negative. By contrast, in FIG. 11, in which the implanted magnet 1010 is "above" the second external magnet 708, rotations of the second external magnet 708 about the second elongate rotational axis in a clockwise direction are denoted as being positive, while rotations of the second external magnet 708 about the second elongate rotational axis in a counterclockwise direction are denoted as being negative.

FIG. 6 illustrates two magnets that may be turned in unison. For example, first external magnet 706 may be turned (by gearing, belts, etc.) synchronously with second external magnet 708 so that the north pole 902 of first external magnet 706 is pointing in the twelve o'clock position when the south pole 904 of the second external magnet 708 is pointing in the twelve o'clock position. By extension, both the south pole 906 of the first external magnet 706 and the north pole 908 of the second external magnet 708 are pointing in the six o'clock position. As illustrated in FIG. 6, both external magnets may be turned in a first direction illustrated by respective arrows 914, 916. The rotating magnetic fields apply a torque on the implanted magnet 1010, causing it to rotate in a second direction as illustrated by arrow 918. When the first and second external magnets 706, 708 are turned in the opposite direction from that shown, the implanted magnet 1010 will be turned in the opposite direction from that shown. While the magnets may be rotated with a zero angular offset, as just described, the magnets may also be rotated with a positive angular offset.

The first external magnet 706 may be rotated to an example first central magnetic axis 1122' by a first angle of rotation 1123. In some embodiments, as just mentioned, the first angle of rotation 1123 is positive, and in some embodiments the first angle of rotation 1123 is negative. The first angle of rotation 1123 may rotate the first central magnetic axis 1122 in a positive direction from 0° to 360°. Additionally, the first angle of rotation 1123 may rotate the first central magnetic axis 1122 in a negative direction from 0° to −360°. Rotations of the first external magnet 706 such that the first central magnetic axis 1122 is rotationally offset by a first angle of rotation 1123 of >0° to <180° are uniquely positive rotational offsets. In the same way, rotations of the first external magnet 706 such that the first central magnetic axis 1122 is rotationally offset by first angle of rotation 1123 of <0° to >−180° are uniquely negative rotational offsets. As will be readily understood, rotations of the first external magnet 706 by a first angle of rotation 1123 of >180° to <3600 are equivalent to rotations of the first external magnet 706 by a first angle of rotation 1123 of <0° to >−180°, and rotations of the first external magnet 706 by a first angle of rotation 1123 of <−180° to <−360° are equivalent to rotations of the first external magnet 706 by a first angle of rotation 1123 of >0° to <180°. Rotations of the first external magnet 706 by a first angle of rotation 1123 of >0° to <180° are uniquely positive rotational offsets that are known as "upward rotations" or "upward offsets." By contrast, rotations of the first external magnet 706 by a first angle of rotation 1123 of <0° to >−180° are uniquely negative rotational offsets that are known as "downward rotations" or "downward offsets."

The second external magnet 708 may also have a rotational offset. The second external magnet 708 may be rotated to an example second central magnetic axis 1120' by a second angle of rotation 1121. In some embodiments, the second angle of rotation 1121 is positive, and in some embodiments the second angle of rotation 1121 is negative. The second external magnet 708, including the second central magnetic axis 1120, may be rotated by a second angle of rotation 1121 in a positive direction from 0° to 360°. Additionally, the second external magnet 708, including the second central magnetic axis 1120, may be rotated by a second angle of rotation 1121 in a negative direction from 0° to −360°. Rotations of the second external magnet 708 such that the second central magnetic axis 1120 is rotationally offset by a second angle of rotation 1121 of >0° to <180° are uniquely positive rotational offsets. In the same way, rotations of the second external magnet 708 such that the second central magnetic axis 1120 is rotationally offset by second angle of rotation 1121 of <0° to >−180° are uniquely negative rotational offsets. As discussed with respect to the first external magnet 706, rotations of the second external magnet 708 by a second angle of rotation 1121 of >180° to <360° are equivalent to rotations of the second external magnet 708 by a second angle of rotation 1121 of <0° to >−180°, and rotations of the second external magnet 708 by a second angle of rotation 1121 of <−180° to <−360° are equivalent to rotations of the second external magnet 708 by a second angle of rotation 1121 of >0° to <180°. Rotations of the second external magnet 708 by a second angle of rotation 1121 of >0° to <180° are uniquely positive rotational offsets that are known as "upward rotations" or "upward offsets." By contrast, rotations of the second external magnet 708 by a second angle of rotation 1121 of <0° to >−180° are uniquely negative rotational offsets that are known as "downward rotations" or "downward offsets."

Either one or both magnets may be rotationally offset. In some embodiments, only the first external magnet 706 is rotated in one of a positive and a negative direction (i.e., upward rotation or downward rotation). In other embodiments, only the second external magnet 708 is rotated in one of a positive and a negative direction (i.e., upward rotation or downward rotation). In yet other embodiments, both magnets are rotated. Any permutation of dual magnet rotation is possible: both first external magnet 706 and second external magnet 708 being rotated upward (by equal or different amounts); both first external magnet 706 and second external magnet 708 being rotated downward (by equal or different amounts); first external magnet 706 being rotated upward while second external magnet 708 being rotated downward (by equal or different amounts); and first external magnet 706 being rotated downward while second external magnet 708 being rotated upward (by equal or different amounts). When both the first external magnet 706 and the second external magnet 708 are rotated equally upward, the rotational systemic offset is the sum of the magnitude of the two offsets. For example, when the first external magnet 706 has an upward rotation of 40° and the second external magnet 708 has a rotation of 40°, the system's rotation is termed, for example, an "upward 80 0" or "80° upward." In the same fashion, if the first external magnet 706 has a downward rotation of −15° and the second external magnet 708 has a downward rotation of −15°, the system's rotation is termed, for example, a "downward 30°" or "30° downward."

Depending on the point on the central vertical axis 1111, changing the rotational offset of one or both the first external magnet 706 and the second external magnet 708 may either increase or decrease the observed flux density for a given gap distance 1138. For example, as will be discussed in greater detail, below, an upward rotational offset (i.e., >0° to <180°) generally increases flux density on the central vertical axis 1111 at a given gap distance 1138. By contrast, a downward offset (i.e., <0° to >−180°) generally decreases flux density on the central vertical axis 1111 at a given gap distance 1138 (however, downward offsets may increase flux density on the central vertical axis 1111 at small gap distances 1138). Once the first external magnet 706 and second external magnet 708 are unilaterally or bilaterally rotated out of phase in either an upward or a downward direction, they may be rotationally locked with respect to each other and rotated as described above (e.g., at the same angular velocity).

Figure 16A:
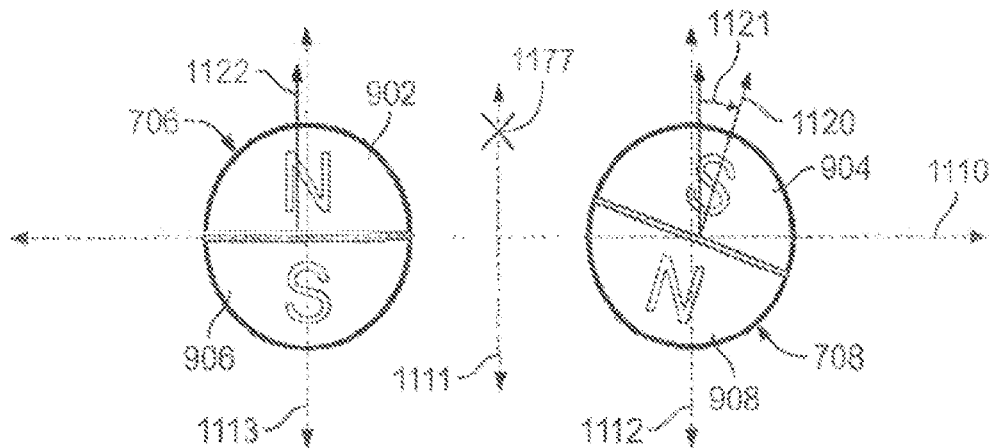
FIGS. 16A-16D illustrate the orientation of two external magnets of the external adjustment device having various positive unilateral rotational offsets.
Figure 16B:
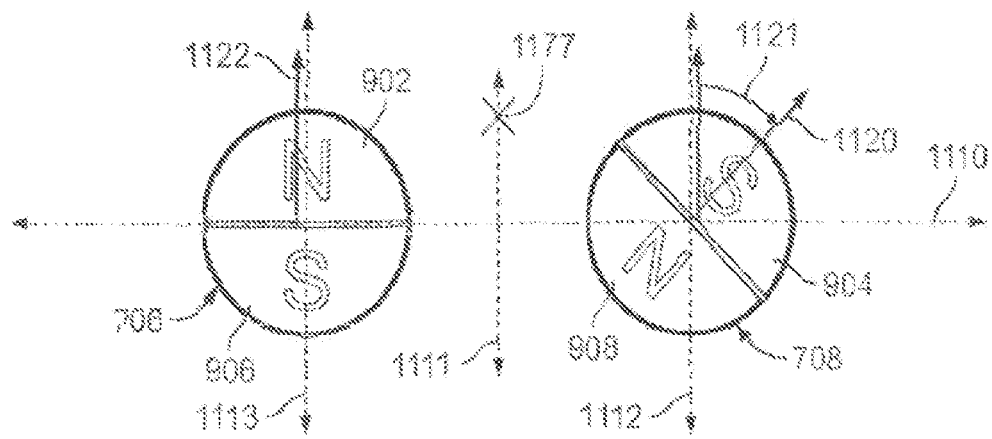
Figure 16C:
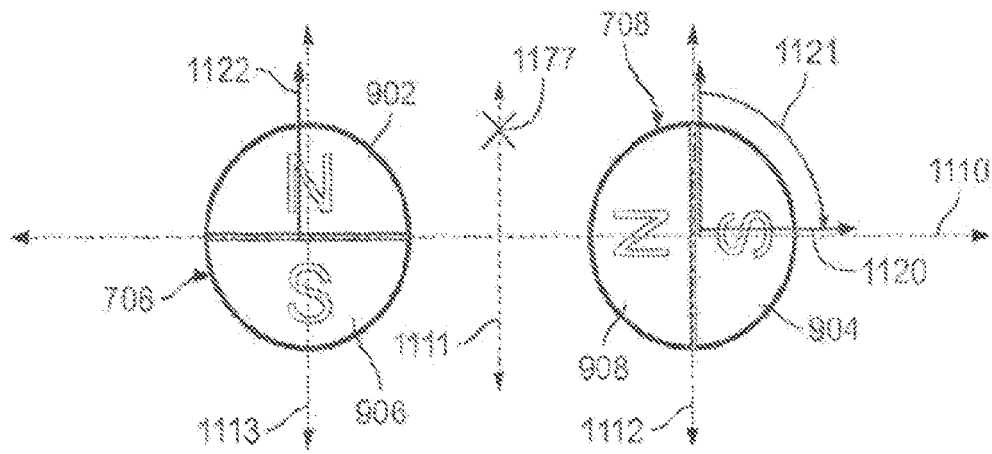
Figure 16D:
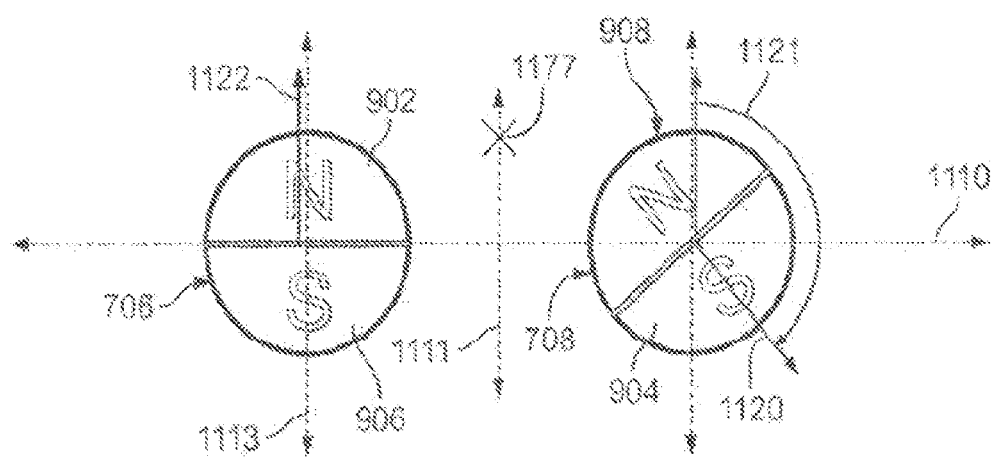

FIGS. 16A-16D illustrate unilateral rotational offset of a single magnet while holding the other at the zero reference. Note that each of FIGS. 16A-16D shows flux reference/measurement point 1177 being "above" the magnets. FIG. 16A shows the second central magnetic axis 1120 of the second external magnet 708 with an upward rotation of about 20° with respect to flux reference/measurement point 1177. It also shows the first central magnetic axis 1122 of the first external magnet 706 being held constant at the zero reference point. FIG. 16B shows the second central magnetic axis 1120 of the second external magnet 708 with an upward rotation of about 45° with respect to flux reference/measurement point 1177. It also shows the first central magnetic axis 1122 of the first external magnet 706 being held constant at the zero reference point. FIG. 16C shows the second central magnetic axis 1120 of the second external magnet 708 with an upward rotation of about 90° with respect to flux reference/measurement point 1177. It also shows the first central magnetic axis 1122 of the first external magnet 706 being held constant at the zero reference point. FIG. 16D shows the second central magnetic axis 1120 of the second external magnet 708 with an upward rotation of about 135° with respect to flux reference/measurement point 1177. It also shows the first central magnetic axis 1122 of the first external magnet 706 being held constant at the zero reference point.

Figure 17A:
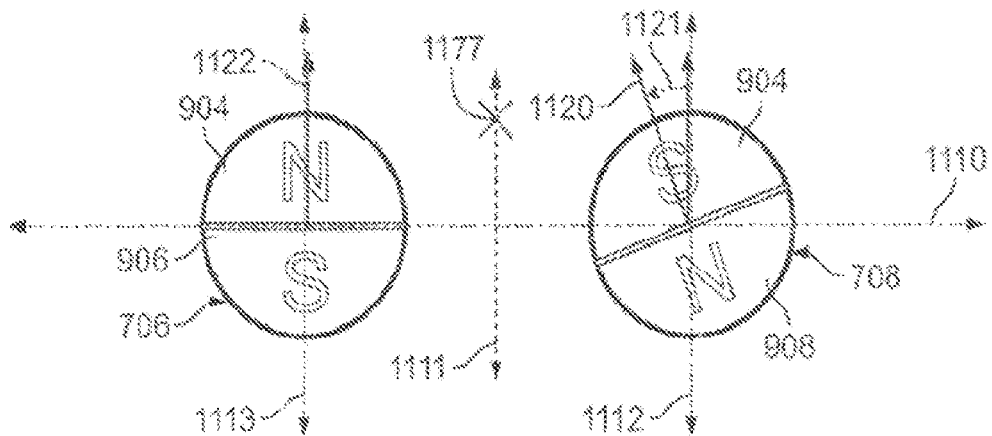
FIGS. 17A-17D illustrate the orientation of two external magnets of the external adjustment device having various negative unilateral rotational offsets.
Figure 17B:
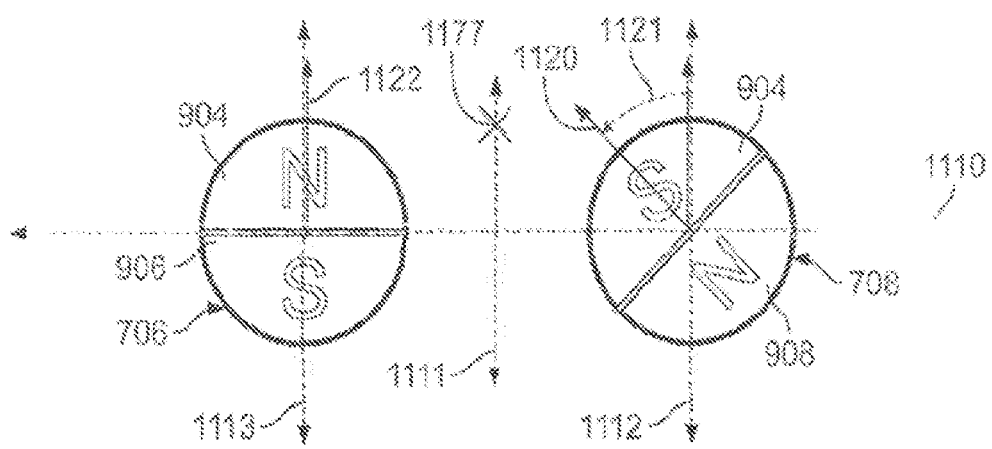

FIGS. 17A-17D illustrate unilateral rotational offset of a single magnet while holding the other at the zero reference. Each of FIGS. 17A-17D shows flux reference/measurement point 1177 being "above" the magnets. FIG. 17A shows the second central magnetic axis 1120 of the second external magnet 708 with a downward rotation of about −20° with respect to flux reference/measurement point 1177. It also shows the first central magnetic axis 1122 of the first external magnet 706 being held constant at the zero reference point. FIG. 17B shows the second central magnetic axis 1120 of the second external magnet 708 with a downward rotation of about −45° with respect to flux reference/measurement point 1177. It also shows the first central magnetic axis 1122 of the first external magnet 706 being held constant at the zero reference point.

Figure 17C:
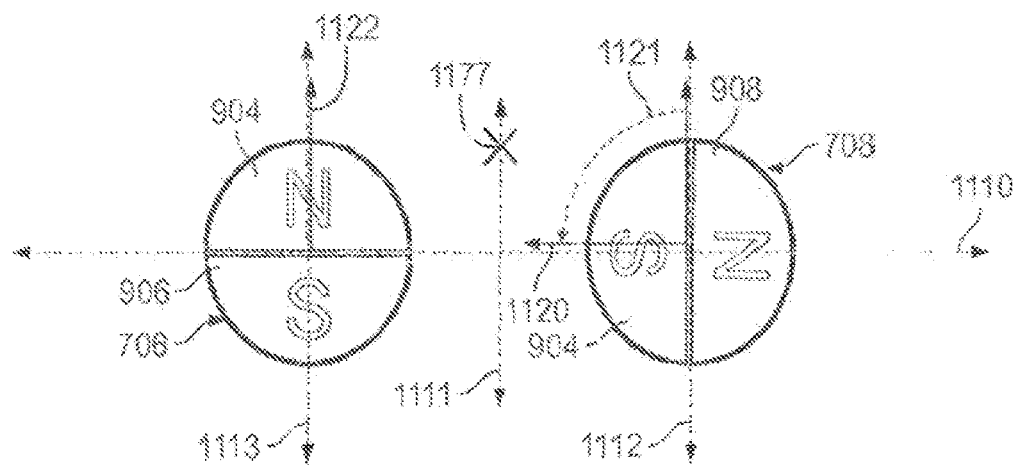
Figure 17D:
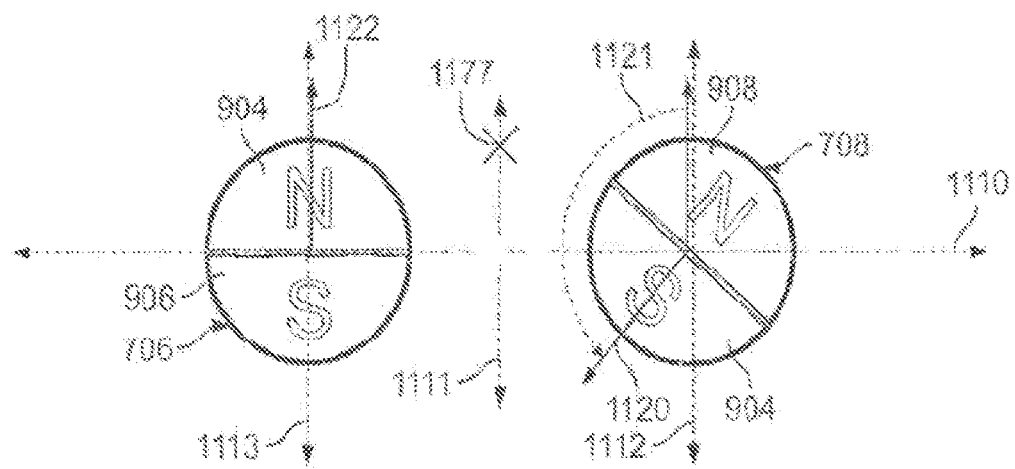

FIG. 17C shows the second central magnetic axis 1120 of the second external magnet 708 with a downward rotation of about −90° with respect to flux reference/measurement point 1177. It also shows the first central magnetic axis 1122 of the first external magnet 706 being held constant at the zero reference point. FIG. 17D shows the second central magnetic axis 1120 of the second external magnet 708 with a downward rotation of about −135° with respect to flux reference/measurement point 1177. It also shows the first central magnetic axis 1122 of the first external magnet 706 being held constant at the zero reference point.

Figure 18:
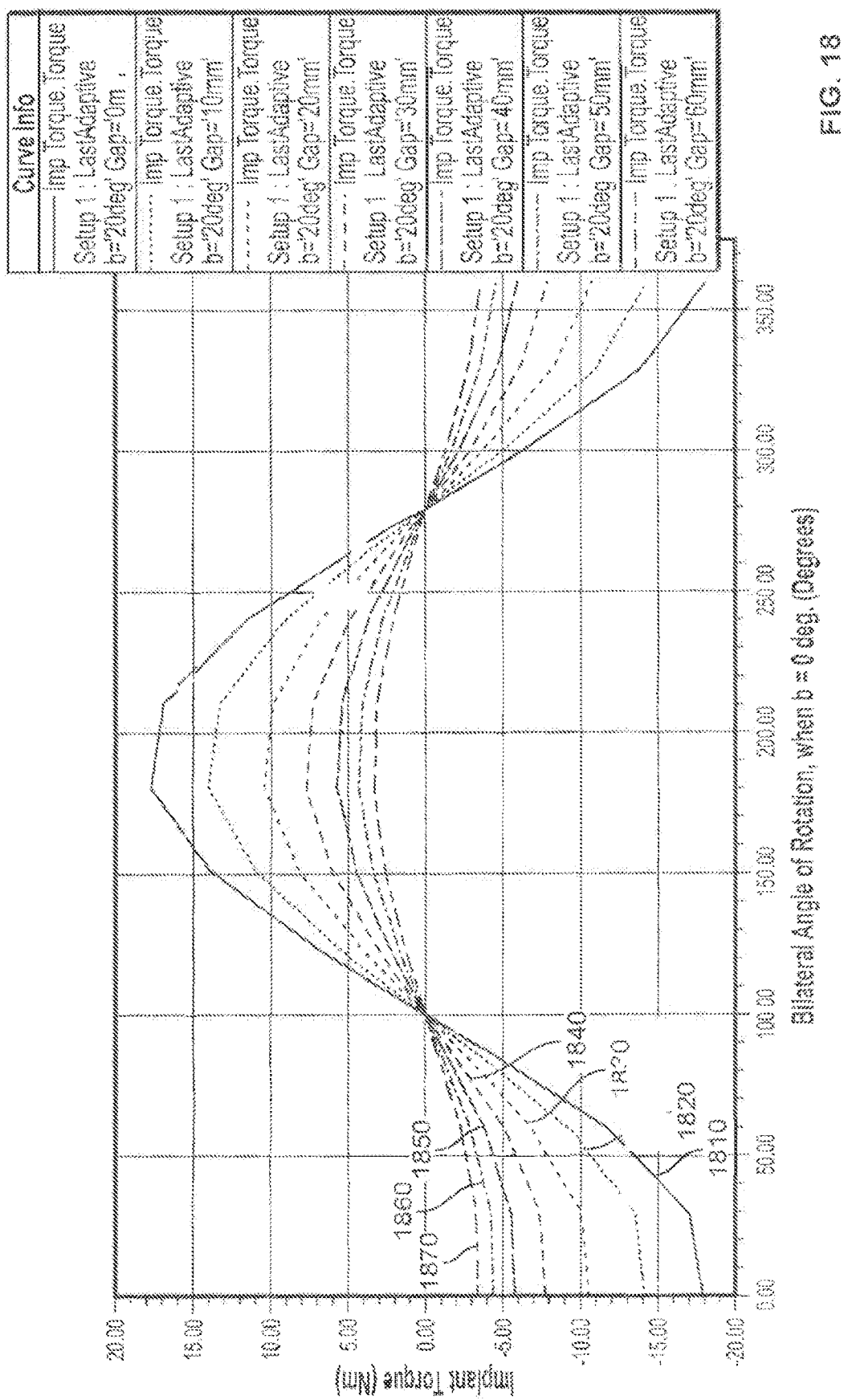
FIG. 18 illustrates a graph of implant torque plotted against unilateral angle of rotation.

FIG. 18A illustrates a graph of implant torque (which is directly proportional to flux density) generated by a first external magnet 706 and a second external magnet 708 versus unilateral angle of rotation (i.e., where only one of the first external magnet 706 and the second external magnet 708 is given a rotational offset while the other is given no rotational offset, as shown in FIGS. 16A-16D and FIGS. 17A-17D).

Figure 19A:
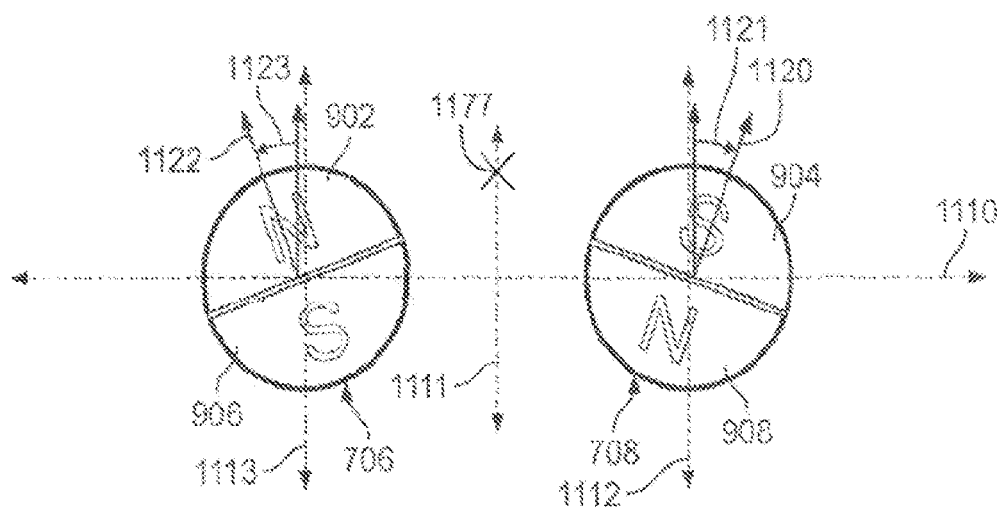
FIGS. 19A-19D illustrate the orientation of two external magnets of the external adjustment device having various positive bilateral rotational offsets.
Figure 19B:
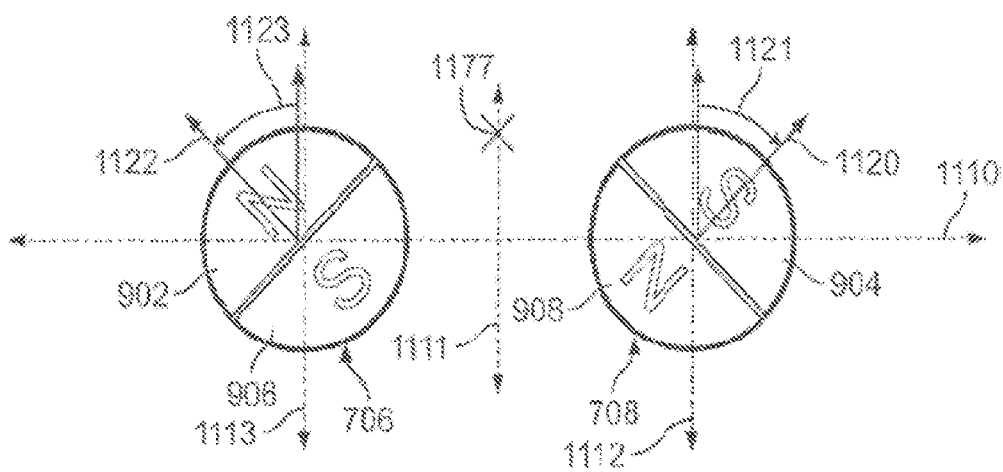
Figure 19C:
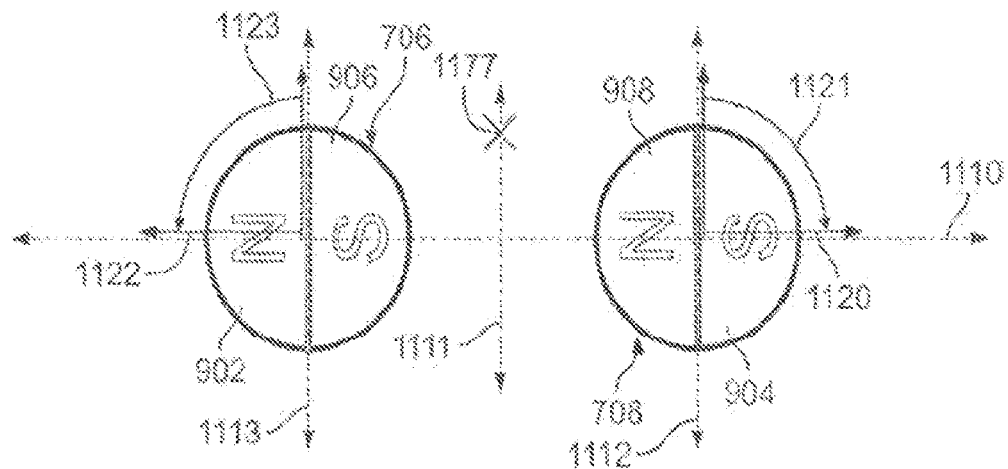
Figure 19D:
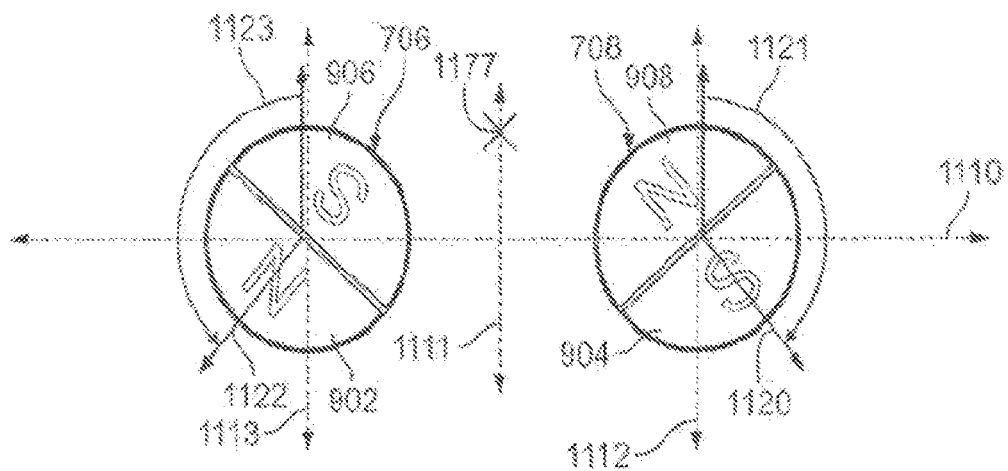

FIGS. 19A-19D illustrate equal, bilateral rotational offset of two magnets, a first external magnet 706 and a second external magnet 708. Again, each of FIGS. 19A-19D shows flux reference/measurement point 1177 being "above" the magnets. FIG. 19A shows the first central magnetic axis 1122 of the first external magnet 706 and the second central magnetic axis 1120 of the second external magnet 708 each having an upward rotation of about 20° with respect to flux reference/measurement point 1177. The system shown in FIG. 19A has a rotational offset of an upward 40°. FIG. 19B shows the first central magnetic axis 1122 of the first external magnet 706 and the second central magnetic axis 1120 of the second external magnet 708 each having an upward rotation of about 45° with respect to flux reference/measurement point 1177. The system shown in FIG. 19B has a rotational offset of an upward 80°. FIG. 19C shows the first central magnetic axis 1122 of the first external magnet 706 and the second central magnetic axis 1120 of the second external magnet 708 each having an upward rotation of about 90° with respect to flux reference/measurement point 1177. The system shown in FIG. 19C has a rotational offset of an upward 180°. And, finally, FIG. 19D shows the first central magnetic axis 1122 of the first external magnet 706 and the second central magnetic axis 1120 of the second external magnet 708 each having an upward rotation of about 135° with respect to flux reference/measurement point 1177. The system shown in FIG. 19D has a rotational offset of an upward 270°.

Figure 20A:
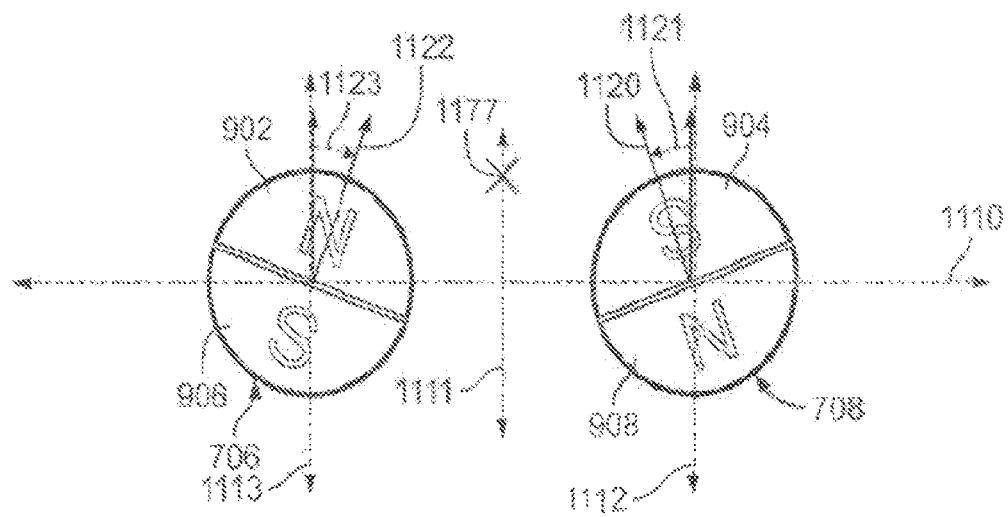
FIGS. 20A-20D illustrate the orientation of two external magnets of the external adjustment device having various negative bilateral rotational offsets.
Figure 20B:
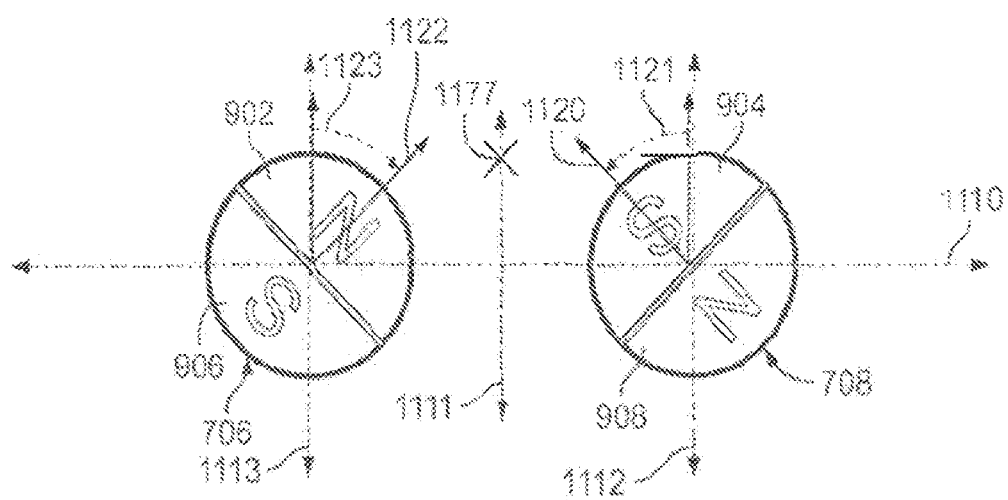
Figure 20C:
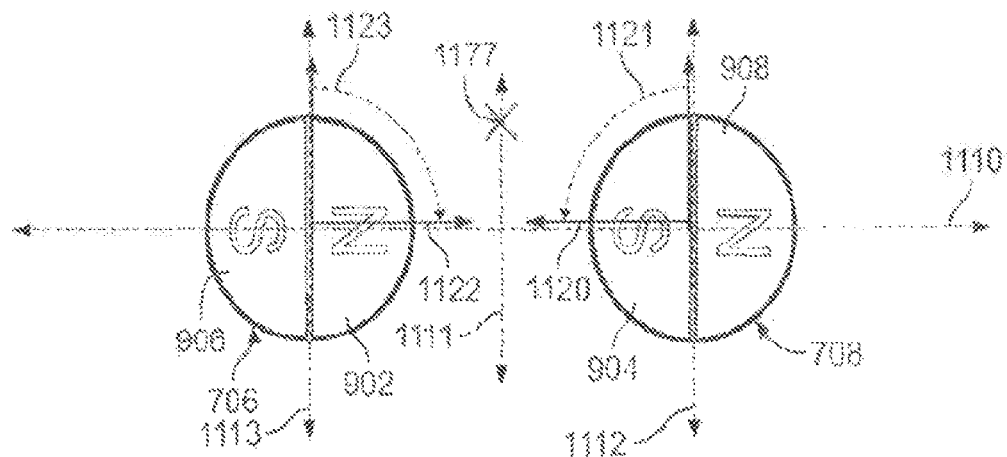
Figure 20D:
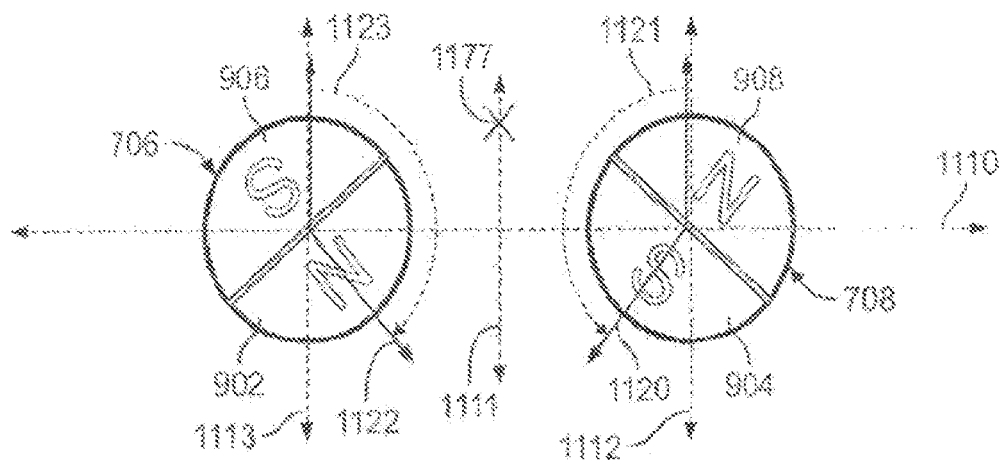

FIGS. 20A-20D illustrate equal, bilateral rotational offset of two magnets, a first external magnet 706 and a second external magnet 708. Each of FIGS. 20A-20D shows flux reference/measurement point 1177 being "above" the magnets. FIG. 20A shows the first central magnetic axis 1122 of the first external magnet 706 and the second central magnetic axis 1120 of the second external magnet 708 each having a downward rotation of about −20° with respect to flux reference/measurement point 1177. The system shown in FIG. 20A has a rotational offset of a downward 40°. FIG. 20B shows the first central magnetic axis 1122 of the first external magnet 706 and the second central magnetic axis 1120 of the second external magnet 708 each having a downward rotation of about −45° with respect to flux reference/measurement point 1177. The system shown in FIG. 20B has a rotational offset of a downward 90°. FIG. 20C shows the first central magnetic axis 1122 of the first external magnet 706 and the second central magnetic axis 1120 of the second external magnet 708 each having a downward rotation of about −90° with respect to flux reference/measurement point 1177. The system shown in FIG. 20C has a rotational offset of a downward 180°. And, finally, FIG. 20D shows the first central magnetic axis 1122 of the first external magnet 706 and the second central magnetic axis 1120 of the second external magnet 708 each having a downward rotation of about −135° with respect to flux reference/measurement point 1177. The system shown in FIG. 20D has a rotational offset of a downward 270°.

Figure 21A:
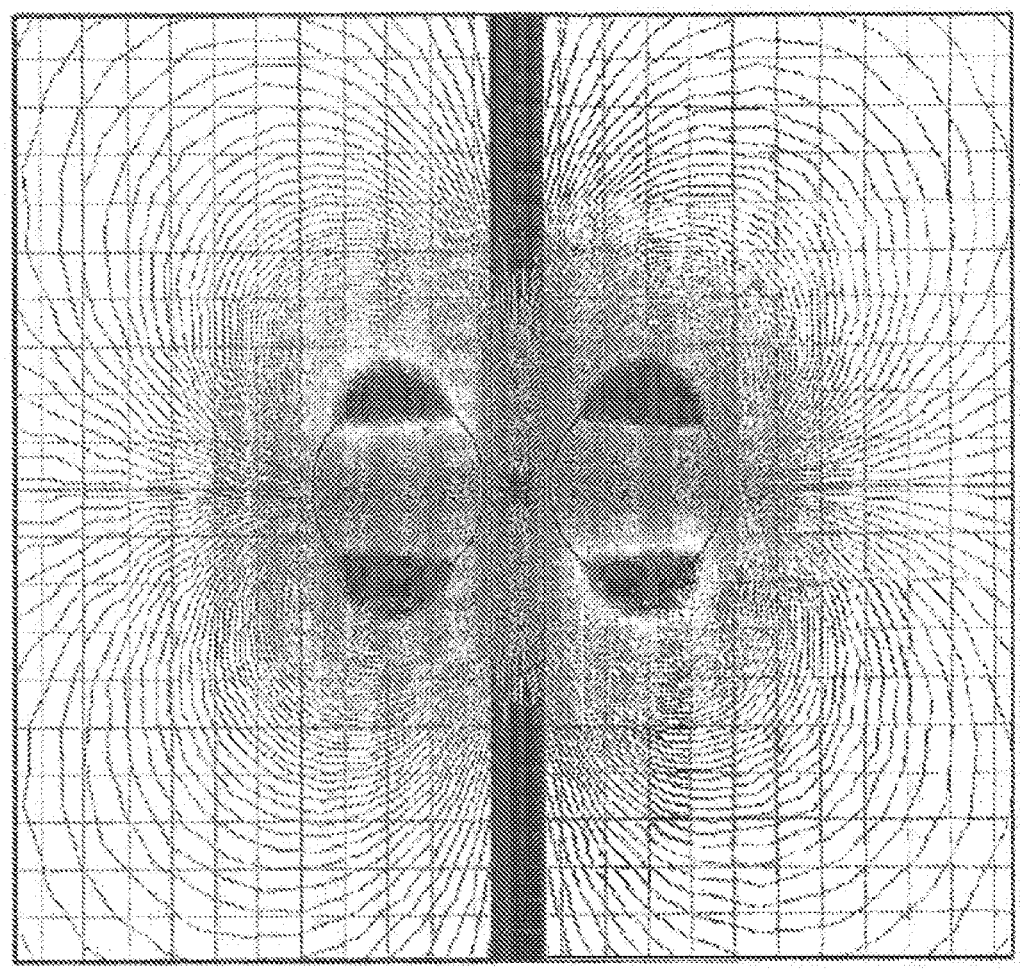
FIGS. 21A-21E illustrate schematics of magnetic field lines surrounding external magnets of an external adjustment device in a reference orientation and various bilateral rotational offsets.
Figure 21B:
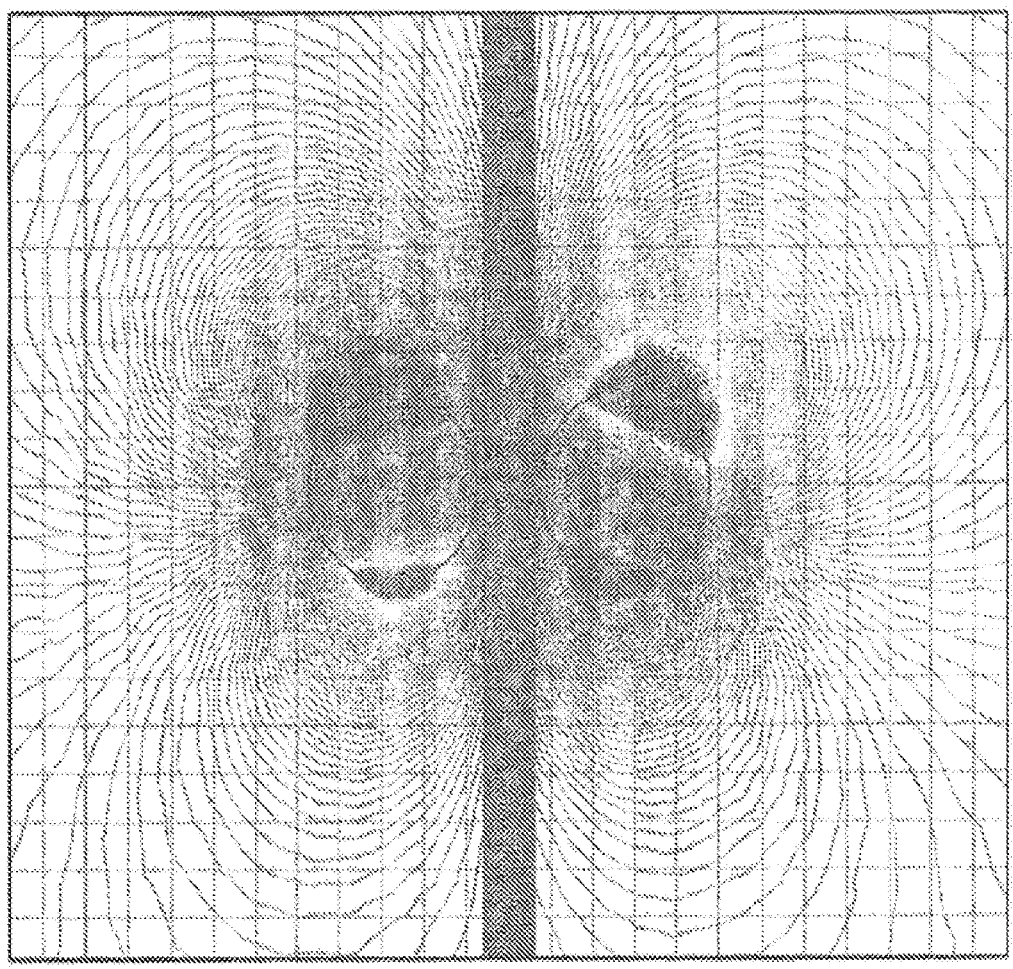
Figure 21C:
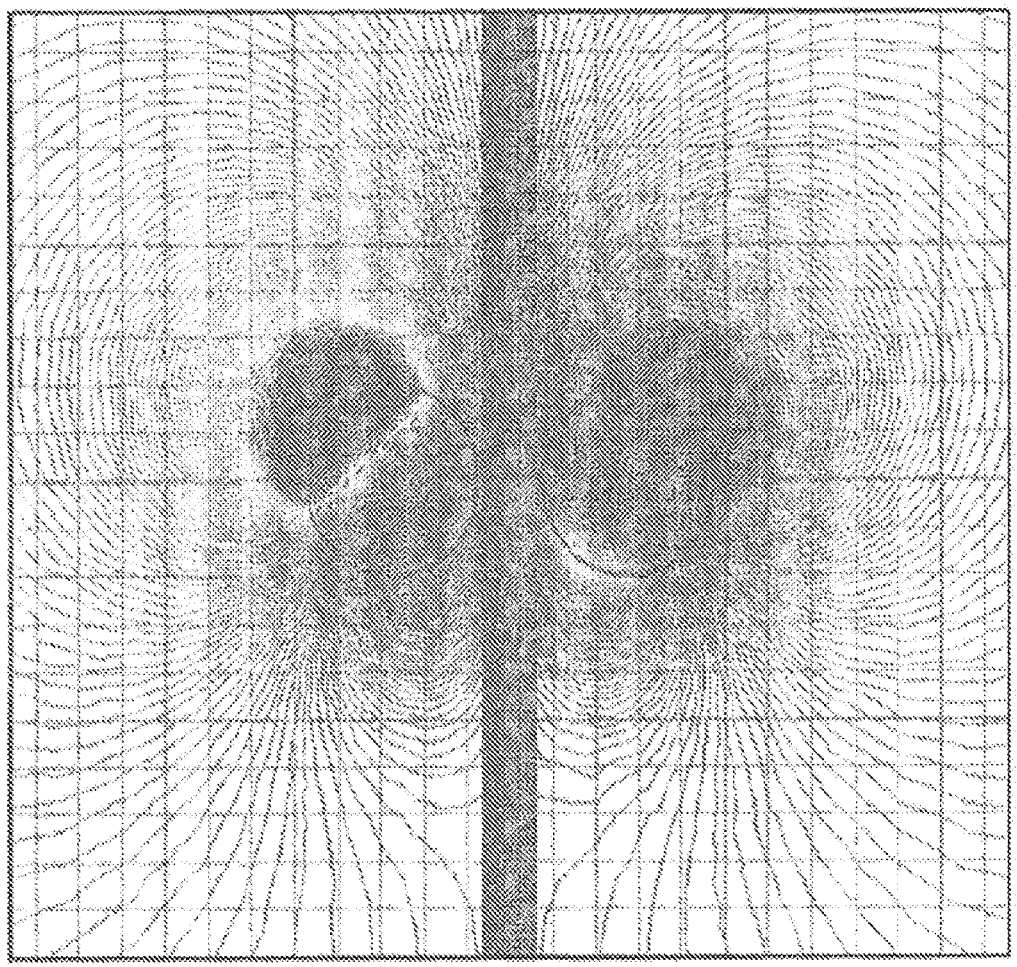
Figure 21D:
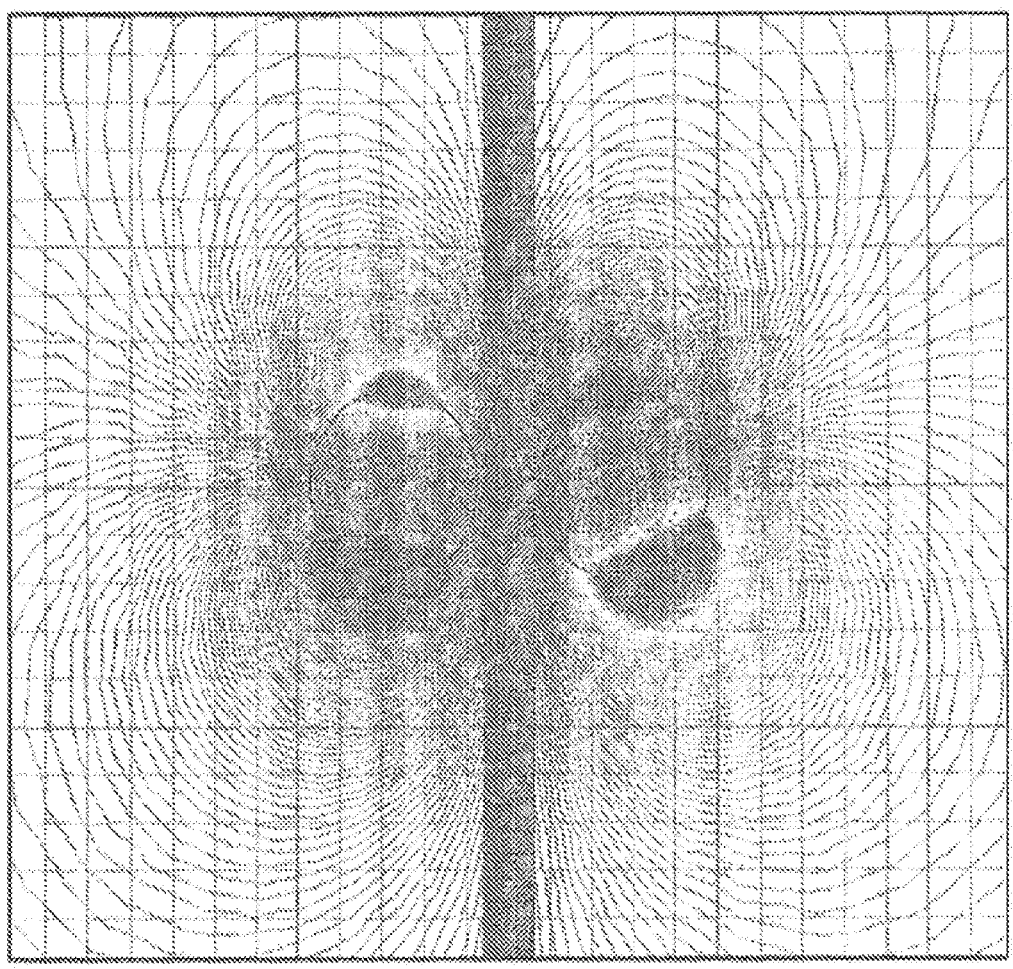
Figure 21E:
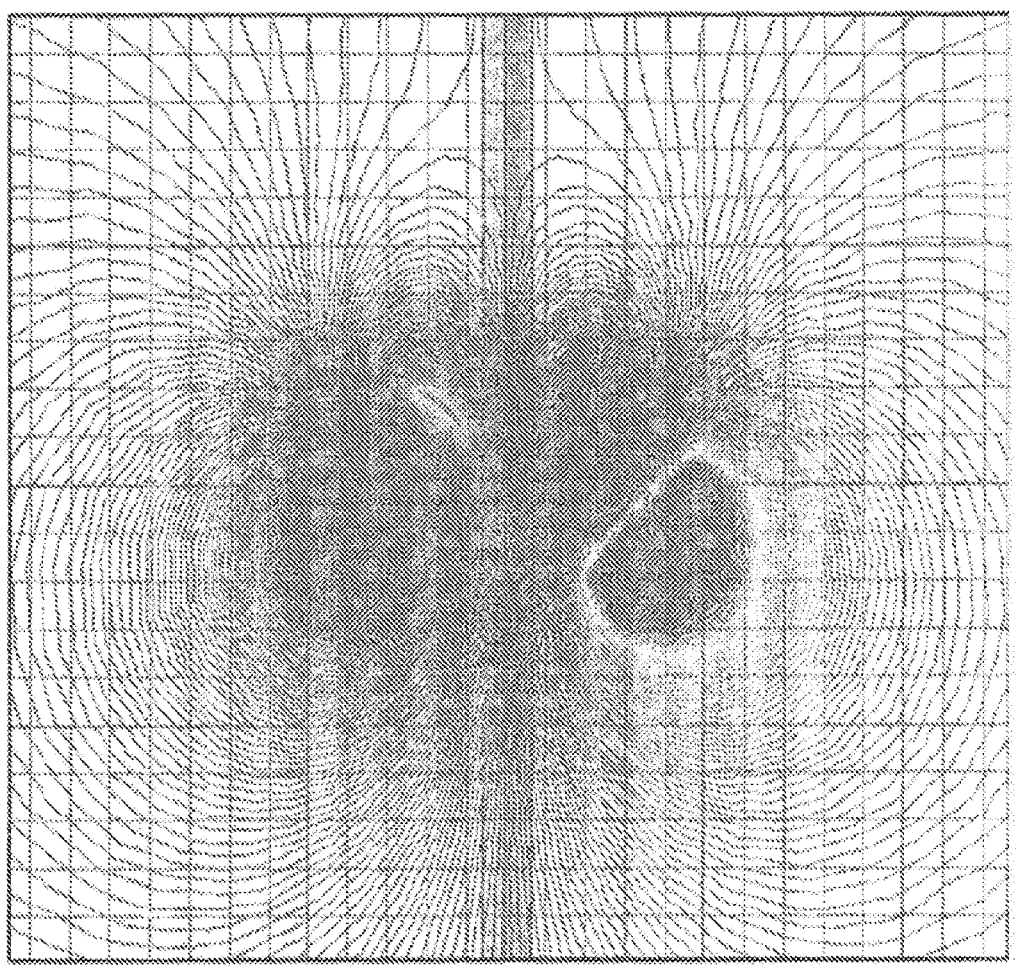

FIG. 21A illustrates a schematic of the magnetic field lines surrounding a first external magnet 706 and a second external magnet 708 in a reference configuration. North pole 902 of the first external magnet 706 is oriented at the zero reference direction and south pole 904 of the second external magnet 708 is also oriented at the zero reference direction. The flux reference/measurement point 1177 is taken to be "above" the magnets, again. By contrast to FIG. 21A, FIG. 21B illustrates a schematic of the magnetic field lines surrounding a first external magnet 706 and a second external magnet 708 that have a systemic rotational offset of an upward 40°. That is to say that the north pole 902 of the first external magnet 706 and the south pole 904 of the second external magnet 708 have each been rotated by 20° (an upward 20 degrees). The flux reference/measurement point 1177 is taken to be "above" the magnets, again. The flux lines above the magnets and along the central vertical axis 1111 in FIG. 21B are denser than the flux lines above the magnets and along the central vertical axis 1111 in FIG. 21A. As mentioned previously, for a given gap distance 1138, upward rotations tend to increase flux density. FIG. 21C illustrates a schematic of the magnetic field lines surrounding a first external magnet 706 and a second external magnet 708 that have a systemic rotational offset of an upward 80°. That is to say that the north pole 902 of the first external magnet 706 and the south pole 904 of the second external magnet 708 have each been rotated by 40° (an upward 40 degrees). The flux reference/measurement point 1177 is taken to be "above" the magnets, again. The flux lines above the magnets and along the central vertical axis 1111 in FIG. 21C are notably denser than the flux lines above the magnets and along the central vertical axis 1111 in FIG. 21A. As mentioned previously, for a given gap distance 1138, upward rotations tend to increase flux density. FIG. 21D illustrates a schematic of the magnetic field lines surrounding a first external magnet 706 and a second external magnet 708 that have a systemic rotational offset of a downward 40°. That is to say that the north pole 902 of the first external magnet 706 and the south pole 904 of the second external magnet 708 have each been rotated by −20° (a downward 20 degrees). The flux reference/measurement point 1177 is taken to be "above" the magnets, again. The flux lines above the magnets and along the central vertical axis 1111 in FIG. 21D are sparser than the flux lines above the magnets and along the central vertical axis 1111 in FIG. 21A (in which the first external magnet 706 and the second external magnet 708 are in their reference configurations). However, it should be noted that these flux lines are even less dense than the flux lines shown above the magnets and along the central vertical axis 1111 in FIG. 21C (in which the first external magnet 706 and the second external magnet 708 have a rotational offset of an upward 80°). For a given gap distance 1138, downward rotations tend to decrease flux density (except at small gap distances 1138 where they may increase, even dramatically, the flux density). Therefore, a downward rotation will produce a lower flux density than the reference system and an even lower flux density than a system having an upward offset/rotation. Finally, FIG. 21E illustrates a schematic of the magnetic field lines surrounding a first external magnet 706 and a second external magnet 708 that have a systemic rotational offset of a downward 80°. That is to say that the north pole 902 of the first external magnet 706 and the south pole 904 of the second external magnet 708 have each been rotated by −10° (a downward 40 degrees). The flux reference/measurement point 1177 is taken to be "above" the magnets. As can be seen, the flux lines above the magnets and along the central vertical axis 1111 in FIG. 21E are very dense at very small gap distances 1138, perhaps even denser than the density observed from an upward 80° offset. However, as the gap distance 1138 increases, the flux density rapidly decreases.

Figure 22A:
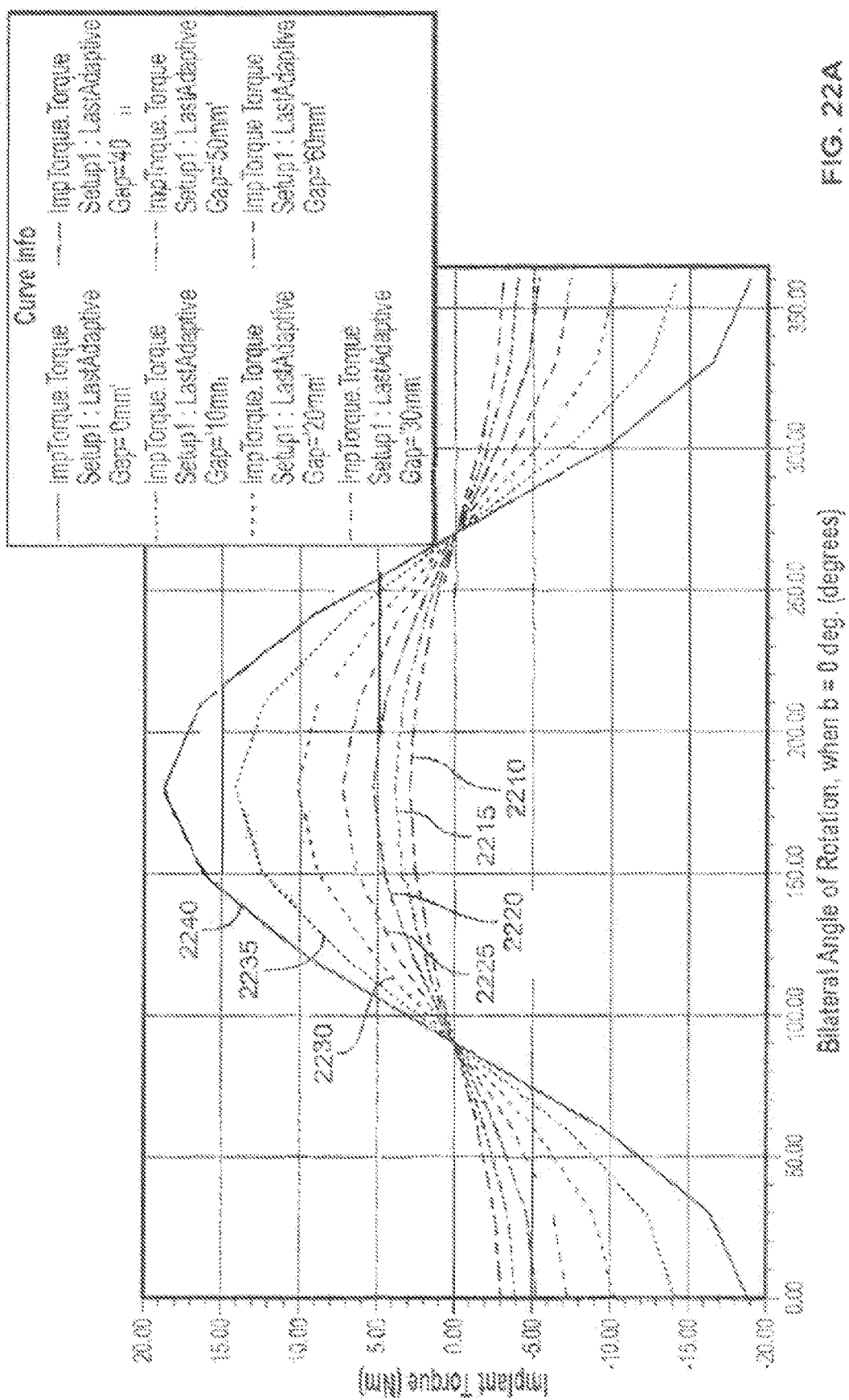
FIGS. 22A-22B illustrate graphs of implant torque plotted against bilateral angle of rotation.
Figure 22B:
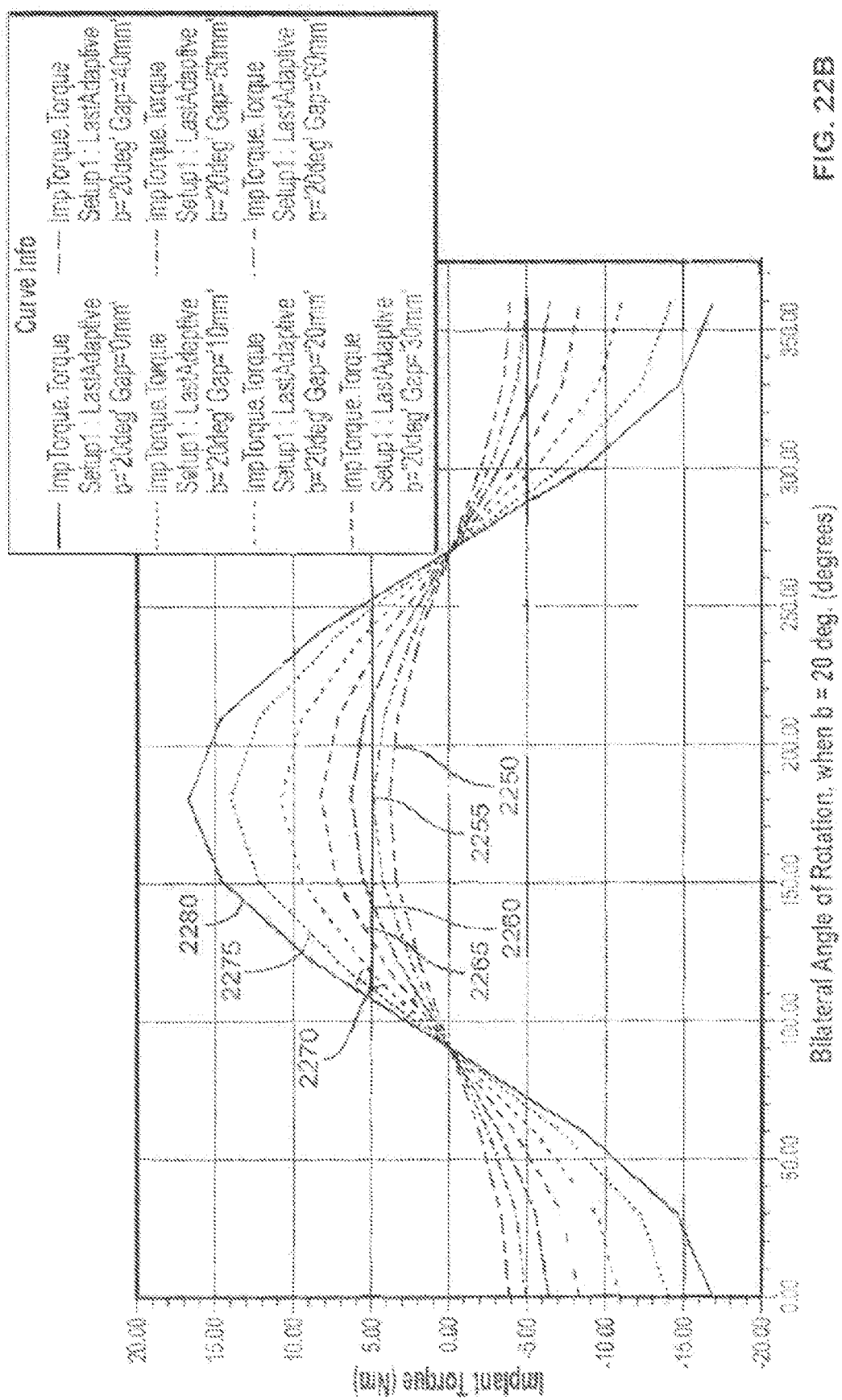

FIGS. 22A-22B illustrate graphs of implant torque (which is directly proportional to flux density) generated by a first external magnet 706 and a second external magnet 708 versus bilateral angle of rotation (i.e., where both the first external magnet 706 and the second external magnet 708 are given an equal rotational offset, as shown in FIGS. 19A-19D and FIGS. 20A-20D).

By contrast to FIGS. 22A-22B, FIG. 23 illustrates a graph of flux density (measured in units of mTesla) versus gap distance in several scenarios, in which no rotation is present. With reference to FIG. 11, the various plots included in FIG. 23 are plots of the static magnetic field strength experienced along the central vertical axis 1111 extending from the edge of the magnet(s), i.e., where the gap distance 1138 is zero, outwards (still on the central vertical axis 1111), to a gap distance 1138 of approximately 5 inches.

First line 2310 is a plot of magnetic flux density versus gap distance for a two magnet system (e.g., a system having a first external magnet 706 and a second external magnet 708) in which the magnets have a intermagnet gap of 0.75 inches and no angular offset (i.e., neither the first external magnet 706 nor the second external magnet 708 is rotated out of phase). An example flux map of such a system is shown in FIG. 21A. Therefore, the first line 2310 may be conceptualized as the flux density along the vertical line immediately between the two magnets (e.g., central vertical axis 1111). The first point on first line 2310 is at the intersection of a line connecting the outermost horizontal edges of the first external magnet 706 and the second external magnet 708. The decreasing values of flux density are illustrated by FIG. 21A in which the flux lines become less as the distance away from the magnets increases. First line 2310 may be considered a reference line against which "increased" and/or "decreased" flux densities are evaluated.

Second line 2320 is a plot of magnetic flux density versus gap distance for a two magnet system (e.g., a system having a first external magnet 706 and a second external magnet 708) in which the magnets have an intermagnet gap of 0.75 inches and a systemic angular offset of an upward 40 degrees (i.e., each of first external magnet 706 and second external magnet 708 has an upward rotation of 20 degrees). An example flux map of such a system is shown in FIG. 21B. Here, the second line 2320 may be conceptualized as the flux density along the vertical line immediately between the two magnets shown in FIG. 21B (e.g., the central vertical axis 1111). The first point on the second line 2320 is at the intersection of a line connecting the outermost horizontal edges of the first external magnet 706 and the second external magnet 708. The value of flux density drops off quicker for second line 2320 than it does for the reference line, first line 2310.

Third line 2330 is a plot of magnetic flux density versus gap distance for a two magnet system (e.g., a system having a first external magnet 706 and a second external magnet 708) in which the magnets have an intermagnet gap of 0.75 inches and a systemic angular offset of a downward 40 degrees (i.e., each of the first external magnet 706 and the second external magnet 708 has a downward rotation of 20 degrees). An example flux map of such a system is shown in FIG. 21D. The third line 2330 may be understood as the flux density along the central vertical axis 1111, just as described with respect to first line 2310 and second line 2320. The flux density starts slightly lower than the reference flux density (i.e., of first line 2310), however, the flux density stays higher than the reference flux density for gap distances of larger than about 15 mm. In a system in which higher torques or flux densities are desired, such a configuration may be useful.

Finally, fourth line 2340 is a plot of magnetic flux density versus gap distance for a two magnet system (e.g., a system having a first external magnet 706 and a second external magnet 708) in which the magnets have an intermagnet gap of 0.75 inches and a systemic angular offset of a downward 80 degrees (i.e., each of the first external magnet 706 and the second external magnet 708 has a downward rotation of 40 degrees). An example flux map of such a system is shown in FIG. 21E. The fourth line 2340 may be understood as the flux density along the central vertical axis 1111, as was described with respect to first line 2310, second line 2320, and third line 2330. Here, by contrast to those lines, the flux density starts lower, but drops off slower than the other lines. Such a configuration may be useful in applications in which gap distances are necessarily larger (e.g., in the 50-100 mm range), but still require relatively high torques.

Figure 15:
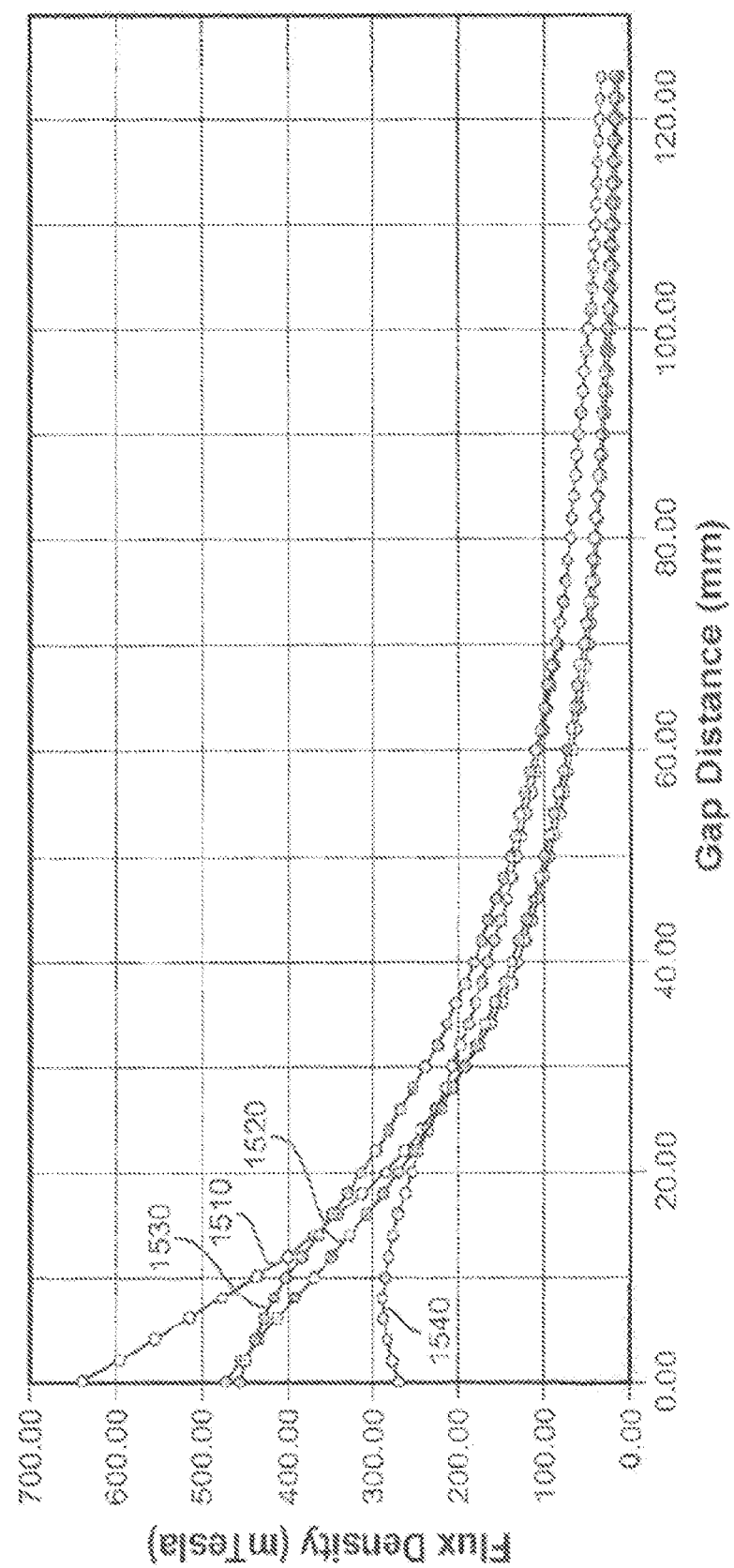
FIG. 15 illustrates a graph of magnetic flux density plotted against gap distance for two different pairs of two external magnets systems in which intermagnet gap and rotational offset are varied.

FIG. 15 illustrates flux density (measured in mTesla) plotted against gap distance for two different two magnet systems in which two variables are changed: intermagnet gap and rotational offset. First line 1510 and second line 1520 illustrate flux density plots generated by a two magnet system having a zero rotational offset. That is to say, both magnets are in the reference position. By contrast, third line 1530 and fourth line 1540 illustrate flux density plots generated by a two magnet system having a systemic downward 80 degree rotational offset. That is to say that the first external magnet 706 and the second external magnet 708 each have a downward rotation of 40 degrees. First, the first line 1510 and the second line 1520 are compared.

As just mentioned, the two magnet system that produced first line 1510 and second line 1520 have a zero degree rotational offset. However, the first two magnet system that produced first line 1510 had an intermagnet gap of about 0.2 inches whereas the second two magnet system that produced second line 1520 had an intermagnet gap of about 0.75 inches. The system in which the magnets were closer together initially has a significantly higher flux density than the system in which the magnets were farther apart—in fact, it is approximately 30% higher at a gap distance of zero. The graph illustrates that the gains achieved through small intermagnet gaps are realized at only relatively short gap distance. The first line 1510 and the second line 1520 substantially converge at about 30 mm, after which they remain approximately equal. This is entirely consistent with FIG. 14 which shows varying intermagnet gaps. Again, FIG. 14 illustrates that magnetic flux density approaches a limit (for any given two magnets) when gap distance is zero and when intermagnet gap is zero. As intermagnet gap increases, flux density decreases (even when gap distance is maintained at a constant zero). Additionally, at least for relatively small increases in intermagnet gap, the effect of intermagnet gap is no longer felt at about 25 mm (regardless of intermagnet gap). That is to say that the flux density plots generated by the systems in which only intermagnet gap varies all converge at about 25 mm at which point in time they continue to track each other (dropping to a limit of zero at approximately an inverse cube).

As discussed above, and by contrast to the zero rotational offset system just discussed, the two magnet system that produced third line 1530 and fourth line 1540 have a systemic downward 80 degree rotational offset. However, the first two magnet system that produced third line 1530 had an intermagnet gap of about 0.2 inches whereas the second two magnet system that produced fourth line 1540 had an intermagnet gap of about 0.75 inches. The system in which the magnets were closer together initially had a significantly higher flux density than the system in which the magnets were farther apart—in fact, it is approximately 70% higher at a gap distance of zero. The graph illustrates that the gains achieved through small intermagnet gaps in systems having a downward rotational offset are realized across a much broader range of gap distances than for systems having no rotational offset. As mentioned above, systems having no rotational offset maintain an increased flux density only for gap distances lower than about 25 mm. By marked contrast, the system having a downward 80 degree rotational offset still experienced an increased flux density at about 50 mm-twice the gap distance. The rotationally offset systems converged at about 50 mm at which point in time they continued to track each other. However, they remain above the systems having no rotational offset.

FIG. 15 illustrates that examples of systems in which both intermagnet gap and gap distance have been manipulated to achieve different results. It will be understood that there are some applications in which small gap distances are possible. One example of such an application is in magnetically adjustable scoliosis rods implanted in children. These rods frequently lie close beneath the skin just above the posterior of the spine—some examples of these devices are disclosed in U.S. Pat. Nos. 8,197,490, 8,057,472, 8,343,192, and 9,179,938, which are incorporated by reference in their entirety herein. In applications such as these (where gap distances are small), the magnitude of torque required must be assessed. When high levels of torque are required, as is illustrated by FIG. 15, a small intermagnet gap may be desirable (decreasing intermagnet gap generally increases magnetic flux) and a downward rotational offset may be undesirable (at small to medium gap distances, downward rotational offsets tend to decrease the flux density). However, high levels of torque may be unnecessary or even detrimental. In these cases, a large intermagnet gap may be desirable (increasing intermagnet gap generally decreases magnetic flux). If even further/greater decrease in torque is desirable, a downward rotational offset may be used.

It will also be understood that there are some applications in which small gap distances are uncommon if not impossible, and where medium to large gap distances must be addressed. An instance of such an application is in magnetically adjustable intramedullary femoral nails. Such nails are placed in the intramedullary canal of the femur; consequently, while adipose, fascia, and muscle may be compressed to some degree, the gap distance is substantially increased by the tissues overlying the femur. Some examples of such devices are disclosed in U.S. Pat. Nos. 8,449,543 and 8,852,187, which are incorporated by reference in their entirety herein. As noted above, a downward rotational offset generally causes an increase in flux density as gap distance increases. Therefore, in these applications, downward rotational offset systems will likely be more effective than their aligned counterparts. For systems having a downward rotational offset of 80 degrees, any increase in flux density due to decreased intermagnet gap is generally lost by about 50 mm. Therefore, if an application for which increased torque (and therefore flux density) is desirable, has a gap distance of greater than about 50 mm, decreasing the intermagnet gap will play very little role in increasing torque. However, if the gap distance is less than about 50 mm, decreasing the gap distance could dramatically increase the possible torque. While it is unlikely that any femoral intramedullary nail would ever experience a small gap distance, if the gap distance is smaller than about 25 mm, having a downward rotational offset would degrade the system's ability to generate higher torques. In that case, a rotationally aligned system having a small gap distance would be better. It should be noted that the effects of rotational offset and intermagnet gap have been discussed here in only a very limited context, and for example's sake only. As is discussed herein there are additional ranges and variables that may be altered to either increase or decrease the magnetic flux density experienced at a given point.

Figure 24:
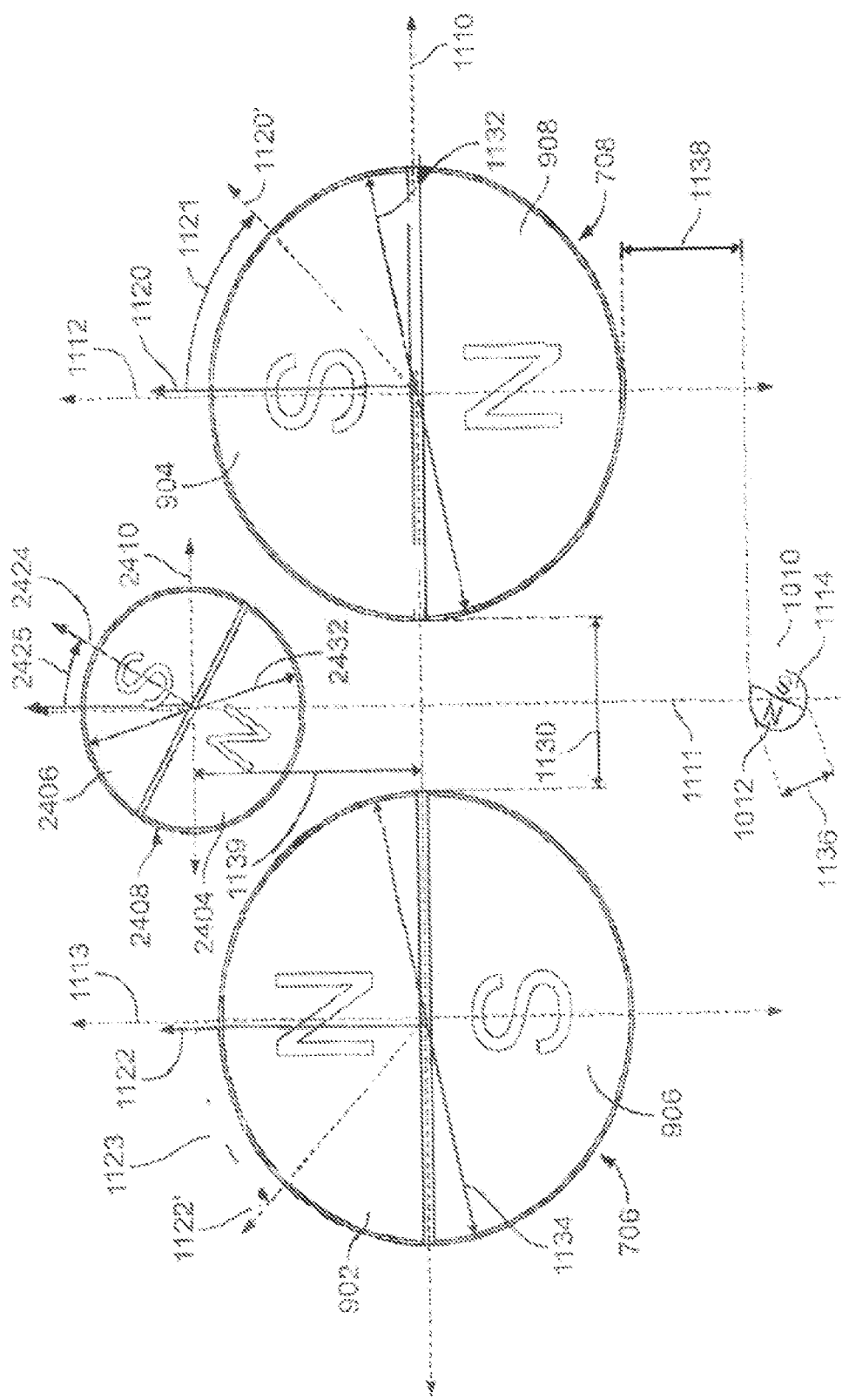
FIG. 24 illustrates the orientation of three external magnets of an external adjustment device in relation to an internal, implanted magnet.

FIG. 24 illustrates another magnet system similar to that shown in FIG. 11, except that a third external magnet 2408 has been added to further shape the magnetic fields created by the system. Like the first external magnet 706 and the second external magnet 708, the third external magnet 2408 has a south pole 2406, a north pole 2404, a third magnet diameter 2432, and a third elongate rotational axis. While the third external magnet 2408 is shown here as having a third magnet diameter 2432 that is smaller than the second magnet diameter 1132 or the first magnet diameter 1134, it should be understood that this is for illustration purposes only. Depending on the flux shaping goals of any given system, the third magnet diameter 2432 may be smaller than, the same as, or larger than the second magnet diameter 1132 and/or the first magnet diameter 1134.

With continued reference to FIG. 24, the third elongate rotational axis (like the first and second elongate rotational axes) is a line through the center of the third external magnet 2408 extending into the page through the center of the third external magnet 2408. While the first external magnet 706 has its first magnet vertical axis 1113 and the second external magnet 708 has its second magnet vertical axis 1112, the third external magnet 2408 is shown as lying directly on the central vertical axis 1111, the line bisecting the intermagnet gap 1130. Placing the third external magnet 2408 on the central vertical axis 1111 may allow an advantageously uniform system across the central vertical axis 1111. However, it should also be understood that the third external magnet 2408 may be placed at anywhere with respect to the first external magnet 706 and the second external magnet 708. As shown in FIG. 24, the position of the third external magnet 2408 is also defined by the third magnet vertical offset 1139, which is the distance along the central vertical axis 1111 from the horizontal axis 1110 to the third external magnet 2408's third magnet horizontal axis 2410.

The third external magnet 2408 may be rotated by a third angle of rotation 2425 to a third central magnetic axis 2424 (shown in FIG. 24). The third external magnet 2408 has a reference configuration such that. The frame of reference for the third external magnet 2408 is the same as that for the second external magnet 708. That is to say that rotations of the third external magnet 2408 about the third elongate rotational axis in a clockwise direction are denoted as being positive, while rotations of the third external magnet 2408 about the third elongate rotational axis in a counterclockwise direction are denoted as being negative. The third external magnet 2408 may also have a rotational offset, just like the first external magnet 706 and the second external magnet 708. In some embodiments, the third angle of rotation 2425 is positive, and in some embodiments the third angle of rotation 2425 is negative. The third external magnet 2408, including the third central magnetic axis 2424, may be rotated by a third angle of rotation 2425 in a positive direction from 0° to 360°. Additionally, the third external magnet 2408, including third central magnetic axis 2424, may be rotated by a third angle of rotation 2425 in a negative direction from 0° to −360°. Like the second external magnet 708, rotations of the third external magnet 2408 such that the third central magnetic axis 2424 is rotationally offset by a third angle of rotation 2425 of >0° to <180° are uniquely positive rotational offsets. In the same way, rotations of the third external magnet 2408 such that the third central magnetic axis 2424 is rotationally offset by third angle of rotation 2425 of <0° to >−180° are uniquely negative rotational offsets. As will be readily understood, rotations of the third external magnet 2408 by a third angle of rotation 2425 of >180° to <360° are equivalent to rotations of the third external magnet 2408 by a third angle of rotation 2425 of <0° to >−180°, and rotations of the third external magnet 2408 by a third angle of rotation 2425 of <−180° to <−360° are equivalent to rotations of the third external magnet 2408 by third angle of rotation 2425 of >0° to <180°. Rotations of the third external magnet 2408 by a third angle of rotation 2425 of >0° to <180° are uniquely positive rotational offsets that are known as "upward rotations" or "upward offsets." By contrast, rotations of the third external magnet 2408 by a third angle of rotation 2425 of <0° to >−180° are uniquely negative rotational offsets that are known as "downward rotations" or "downward offsets."

Figure 25A:
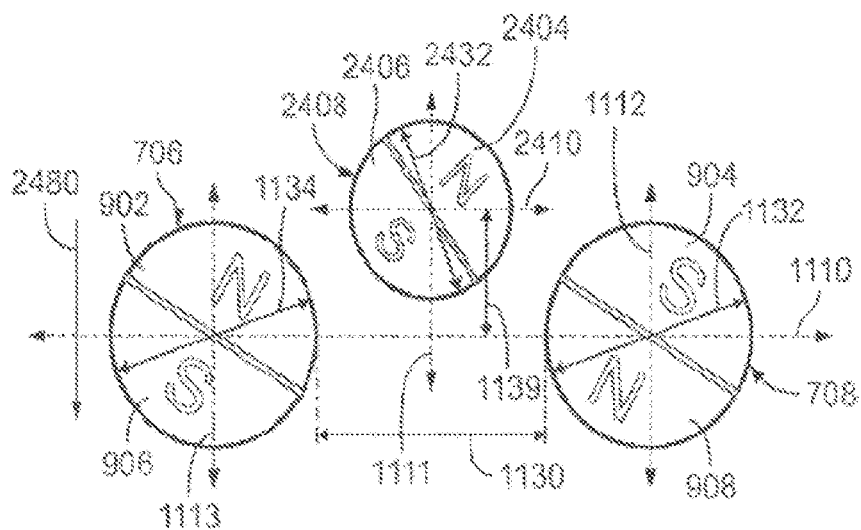
FIGS. 25A-25C illustrate various orientations of three external magnets of an external adjustment device.
Figure 25B:
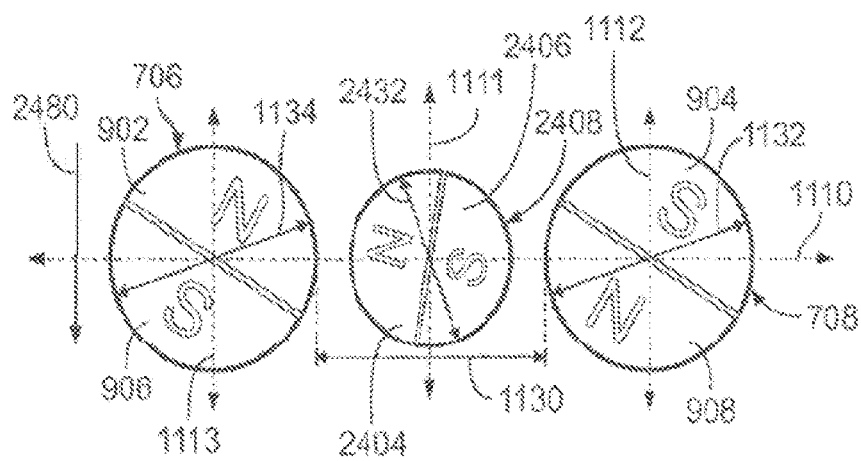
Figure 25C:
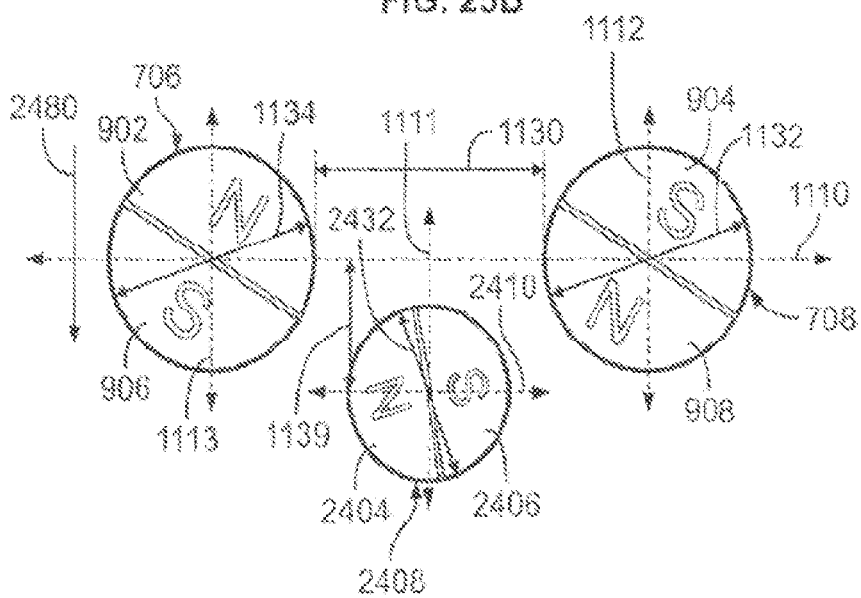

While FIG. 24 illustrates the third magnet horizontal axis 2410 of the third external magnet 2408 as being between the horizontal axis 1110 and the implanted magnet 1010, other placements are possible. FIGS. 25A-25C illustrate various examples of where the third external magnet 2408 may be placed. In FIGS. 25A-25C, the position of the implanted magnet 1010 is identified by the direction of orientation 2480: while the implanted magnet 1010 in FIG. 24 is shown as being "above" the first external magnet 706, second external magnet 708 and third external magnet 2408, in FIGS. 25A-25C it is noted as being "below" the first external magnet 706, second external magnet 708, and third external magnet 2408.

FIG. 25A illustrates a three magnet system in which the third magnet vertical offset 1139 is positive, such that the third external magnet 2408 is positioned above the horizontal axis 1110, the first external magnet 706 and the second external magnet 708. The third magnet vertical offset 1139 may have any positive value that is magnetically meaningful. Because magnetic fields drop off at about an inverse square, as the third magnet vertical offset 1139 increases (as shown in FIG. 25), the effect of the third external magnet 2408 will rapidly drop off. In FIG. 25A, both the first external magnet 706 and the second external magnet 708 are closer to the implanted magnet 1010 (defined either by center to center distance). Therefore, as long as the first external magnet 706 and the second external magnet 708 have larger diameters than the third magnet diameter 2432, the effect felt by the implanted magnet 1010 from the third external magnet 2408 will be less than the effect felt by the implanted magnet 1010 from either the first external magnet 706 or the second external magnet 708. Of course, if the third magnet diameter 2432 were increased sufficiently, the third external magnet 2408 could have a sufficiently strong field that the opposite were true. By the same token, parameters could be optimized such that each of the three magnets affects the implanted magnet 1010 equally.

FIG. 25B illustrates a second three magnet system in which the third magnet vertical offset 1139 is zero (i.e., the third magnet horizontal axis 2410 and the horizontal axis 1110 lie on/are the same line). In FIG. 25B, the third external magnet 2408 will always be closer to the implanted magnet (when lying along the central vertical axis 1111 and defined by center to center distance). Therefore, to have an equal effect as the first external magnet 706 and the second external magnet 708, the third magnet diameter 2432 may be smaller than either the second magnet diameter 1132 and/or the first magnet diameter 1134 (at a threshold diameter). However, rather than having an equal effect, it may be desirable for the third external magnet 2408 to have a stronger effect than the first external magnet 706 or the second external magnet 708. In such a case, the third magnet diameter 2432 may be increased above the threshold diameter. Of course, in some embodiments, it is desirable to have a lesser effect produced by the third magnet diameter 2432 than that felt from the first external magnet 706 or the second external magnet 708. In those cases, the third magnet diameter 2432 may be decreased below the threshold diameter.

FIG. 25C illustrates a third three magnet system in which the third magnet vertical offset 1139 is negative, such that the third external magnet 2408 is positioned below the horizontal axis 1110, the first external magnet 706 and the second external magnet 708. The third magnet vertical offset 1139 may have any negative value that is magnetically meaningful. Because magnetic fields drop off at about an inverse square, as the third magnet vertical offset 1139 becomes increasingly negative, the effect (along the central vertical axis 1111) of the first external magnet 706 and the second external magnet 708 will rapidly drop off. FIG. 25C illustrates a third external magnet 2408 having a third magnet diameter 2432 that is smaller than the first magnet diameter 1134 and the second magnet diameter 1132. Because the third external magnet 2408 is further down the central vertical axis 1111 (e.g., closer to the theoretical implanted magnet 1010), the effect it has on flux density in the direction of orientation 2480 may be more pronounced than either the first external magnet 706 or the second external magnet 708. However, as described above, depending on system requirements, the diameters of the various magnets may be changed to balance or emphasize the magnetic input of one magnet over another (while the first external magnet 706 and the second external magnet 708 may generally have the same diameter, they may have different diameters). For example, the third magnet diameter 2432 could be increased to emphasize the effect of the third external magnet 2408. Or, one or more of the first magnet diameter 1134 and the second magnet diameter 1132 could be increased (while possibly decreasing the third magnet diameter 2432) to increase the effect of the first external magnet 706 and the second external magnet 708 vis-à-vis the third external magnet 2408.

In addition to simple magnets, such as a compass, a horseshoe magnet, or even a rotational poled cylindrical magnet such as the first external magnet 706 and second external magnet 708, it is possible to create complex magnets in which the flux direction for each pole may be selected at will. A common example of a complex magnet is the refrigerator magnet in which magnetism exists only on one side—the back of the magnet will stick to a refrigerator while the front will not. This phenomenon is due to selective orientation of the flux direction during construction of the magnet that allows magnetic field to only to be present on one side of the magnet. The phenomenon is known as the Halbach effect and the arrangement known as a Halbach array. Straight magnets may be created in Halbach arrays so that a magnetic field exists on only one side by simply arranging north-south poled pieces side-by-side so that each consecutive piece's north pole has been rotated a quarter turn from the previous magnet. Once aligned as described, the direction of magnetization will be rotating uniformly as you progress in a particular direction.

Generally a Halbach array is an arrangement of permanent magnets that can augment the magnetic field on one side of the Halbach array while canceling the magnetic field to near zero or substantially near zero on the other side of the Halbach array. For example, the magnetic field can be enhanced on the bottom side of the Halbach array and cancelled on the top side (a one-sided flux) of the Halbach array. The quarter turn rotating pattern of permanent magnets can be continued indefinitely and have the same effect. Increasingly complex Halbach arrays may be used to shape the magnetic field for any magnet, including cylindrical magnets.

Figure 26A:
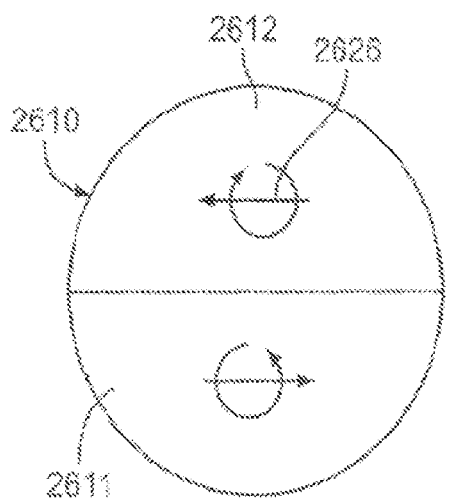
FIGS. 26A-26C illustrate various cylindrical magnets having shaped magnetic fields.
Figure 26B:
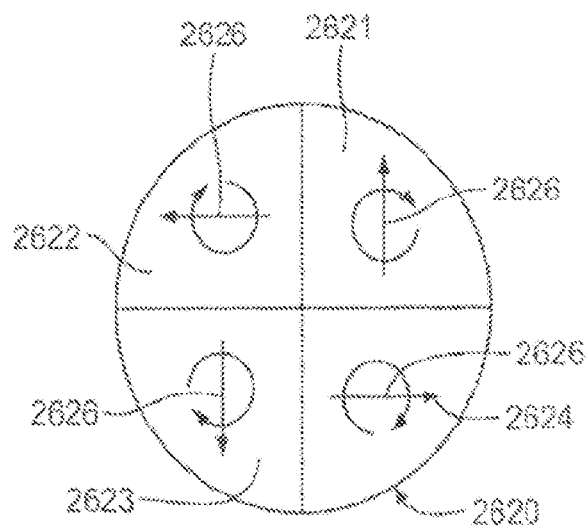
Figure 26C:
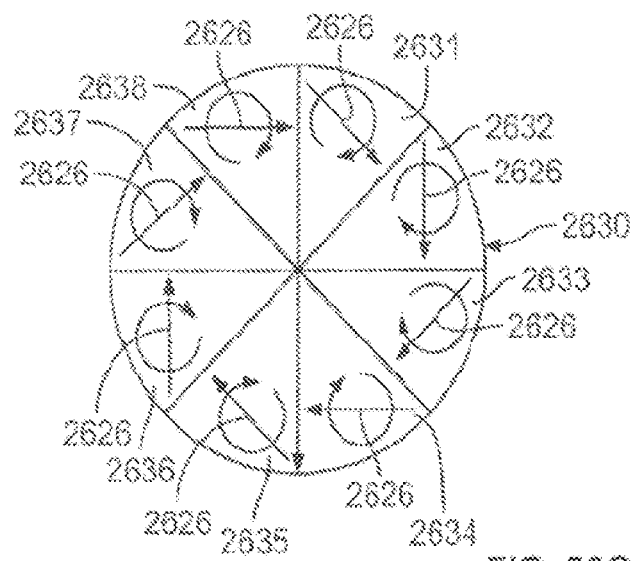

FIGS. 26A-26C illustrate various cylindrical magnets in which the magnetic flux direction of the individual poles may be manipulated. FIG. 26A illustrates a two-poled magnet 2610 having a first pole 2611 and a second pole 2612 each of which has a magnetic flux field 2626. Using Halbach arrays, the magnetic flux field 2626 may be "pointed" in any direction. For example, a magnetic field could be created substantially only one side of the magnet. FIG. 26B illustrates a four-poled magnet 2620 having a first pole 2621, a second pole 2622, a third pole 2623, and a fourth pole 2624, each of which has a magnetic flux field 2626. As described with respect to FIG. 26A, each magnetic flux field 2626 may be "pointed" in any direction. Finally, FIG. 26C illustrates an eight-poled magnet 2630 having a first pole 2631, a second pole 2632, a third pole 2633, a fourth pole 2634, a fifth pole 2635, a sixth pole 2636, a sixth pole 2636, and an eighth pole 2638, each of which has a magnetic flux field 2626. Using the principles of Halbach arrays with increasing numbers of poles, complex magnets with advantageous properties may be created. For example, it may be possible to create a cylindrical magnet having a single, intensely focused field on one side of the magnet. By contrast, it may be possible to create a cylindrical magnet having four, less weaker fields that are separated by magnetic dead zones (i.e., a zone in which there is little to no magnetic flux present). These complex magnets may be advantageously applied to implants, such as the implanted magnet 1010. Implanted magnets with more intensely focused magnetic fields may be able to generate higher coupling torques. Alternatively, rather than increasing torques, it may be possible to decrease the size of the implanted magnet 1010. For example focused magnetic fields on a smaller, complex implanted magnet 1010 (having one or more Halbach array) may be capable of generating coupling torques equivalent, or even greater, than a standard two-poled magnet with comparatively unfocused magnetic fields. Such complex magnets may also be incorporated into the external adjustment device 700. Again, the one or more Halbach array may allow a decrease in magnet size, an increase in coupling torque, or even both. The effect may be increased if complex magnets were used in both the implanted magnet 1010 and the external adjustment device 700.

Figure 27:
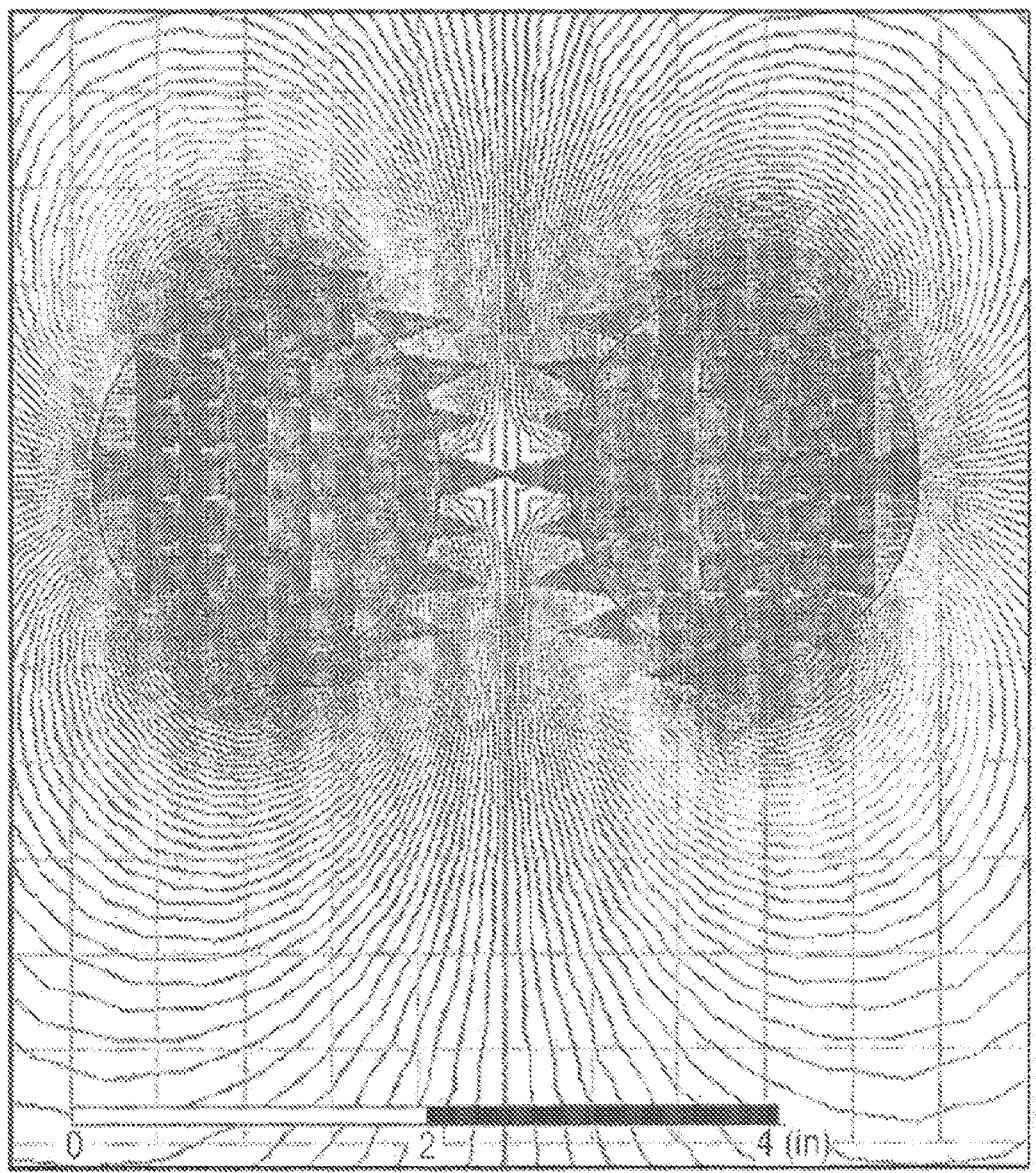
FIG. 27 illustrates a magnetic flux map of a two magnet system

FIG. 27 illustrates a magnetic flux map of a two magnet system, such as that shown in FIG. 11. By contrast to FIG. 11, both magnets have been rotated 90 degrees in the clockwise direction. Therefore, the north pole 902 of the first external magnet 706 is directly facing the north pole 908 of the south pole 904. This flux map is very similar to the flux map shown in FIG. 13B.

Figure 28A:
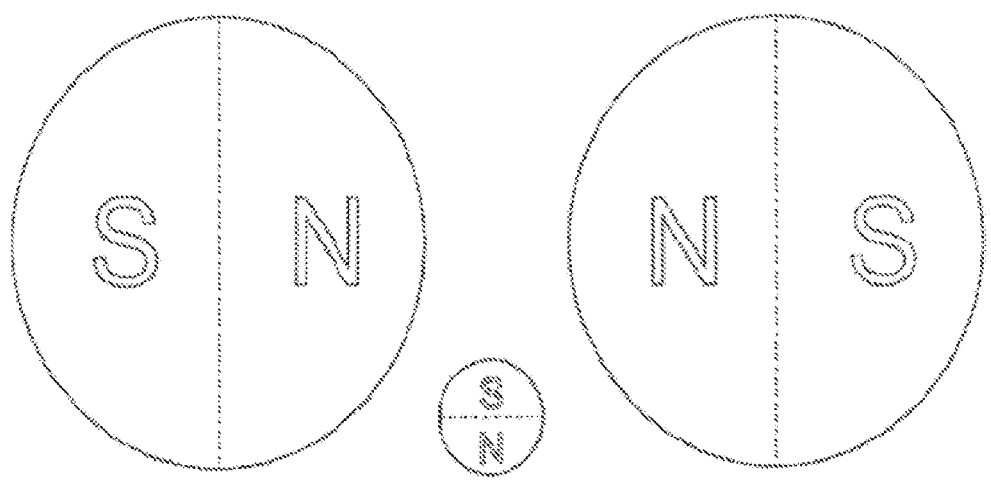
FIG. 28A illustrates a schematic diagram of three magnet system

FIG. 28A illustrates a schematic diagram of three magnet system, similar to that illustrated in FIG. 24, and FIGS. 25A-25C. In FIG. 28A, the implanted magnet is "below" the three magnet system, such that the smaller of the three magnets is on the same side of the horizontal axis 1110 as the implanted magnet 1010. FIG. 28A illustrates one potential configuration of a three magnet system. The larger two of the three magnets are configured just as shown in FIG. 27. However, the smaller of the three magnets (similar to the third external magnet 2408 of FIG. 24), has a south pole that is 90 degrees offset from the larger magnets. That is to say that the line dividing the north and south poles on the small magnet is perpendicular to the (parallel) lines dividing the south and north poles of the larger magnets. It has been observed that this configuration may shape the magnetic field toward the direction of the implanted magnet to provide an increased magnetic field density at that location. In at least one embodiment, this configuration (depending on the distances between magnets, magnet size, gap distance, etc.) can provide 50% more magnetic flux density, and therefore 50% more force than 2 magnet systems (such as that shown in FIG. 27).

Figure 28B:
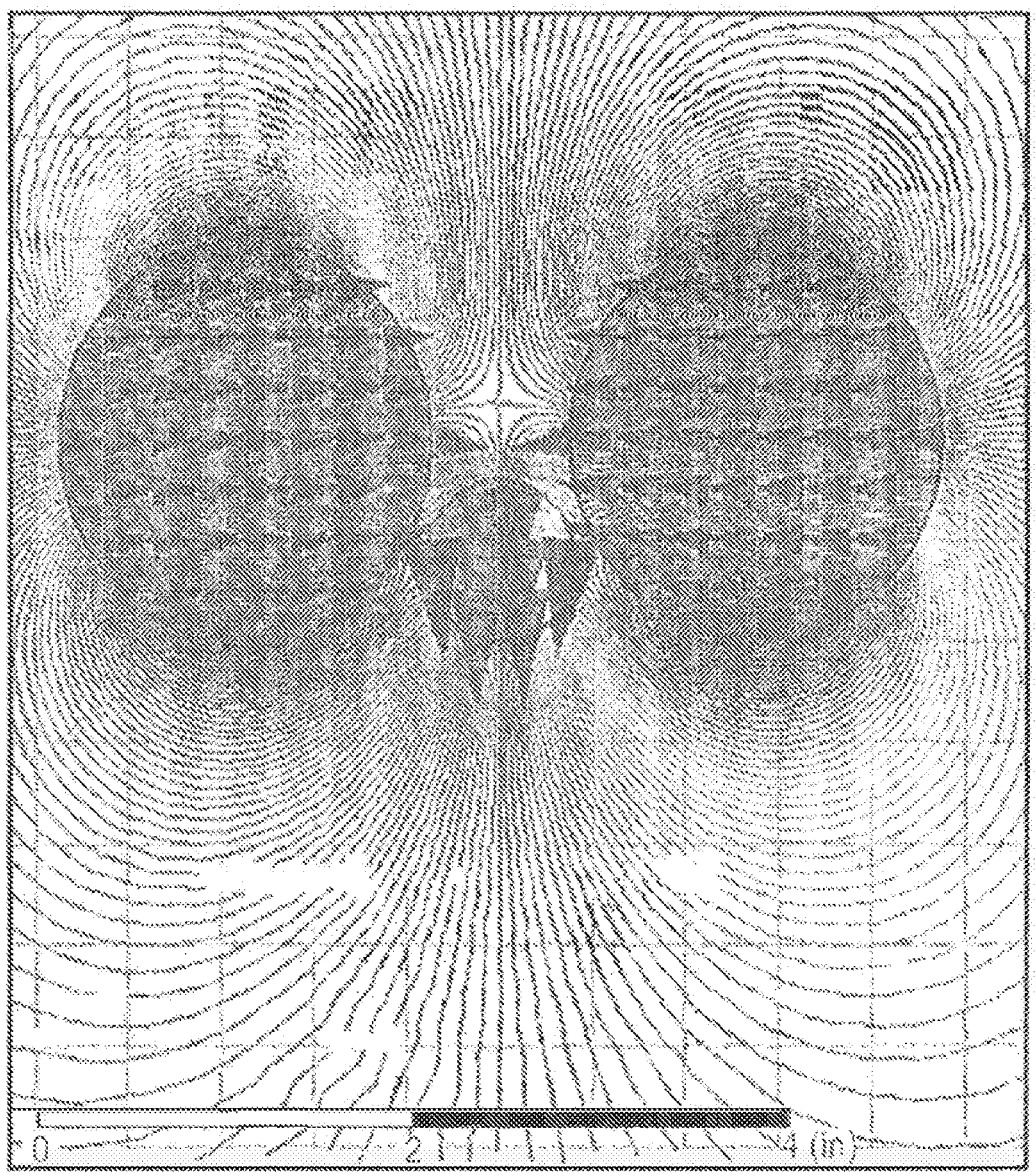
FIGS. 28B-C illustrate flux maps of three magnet systems.
Figure 28C:
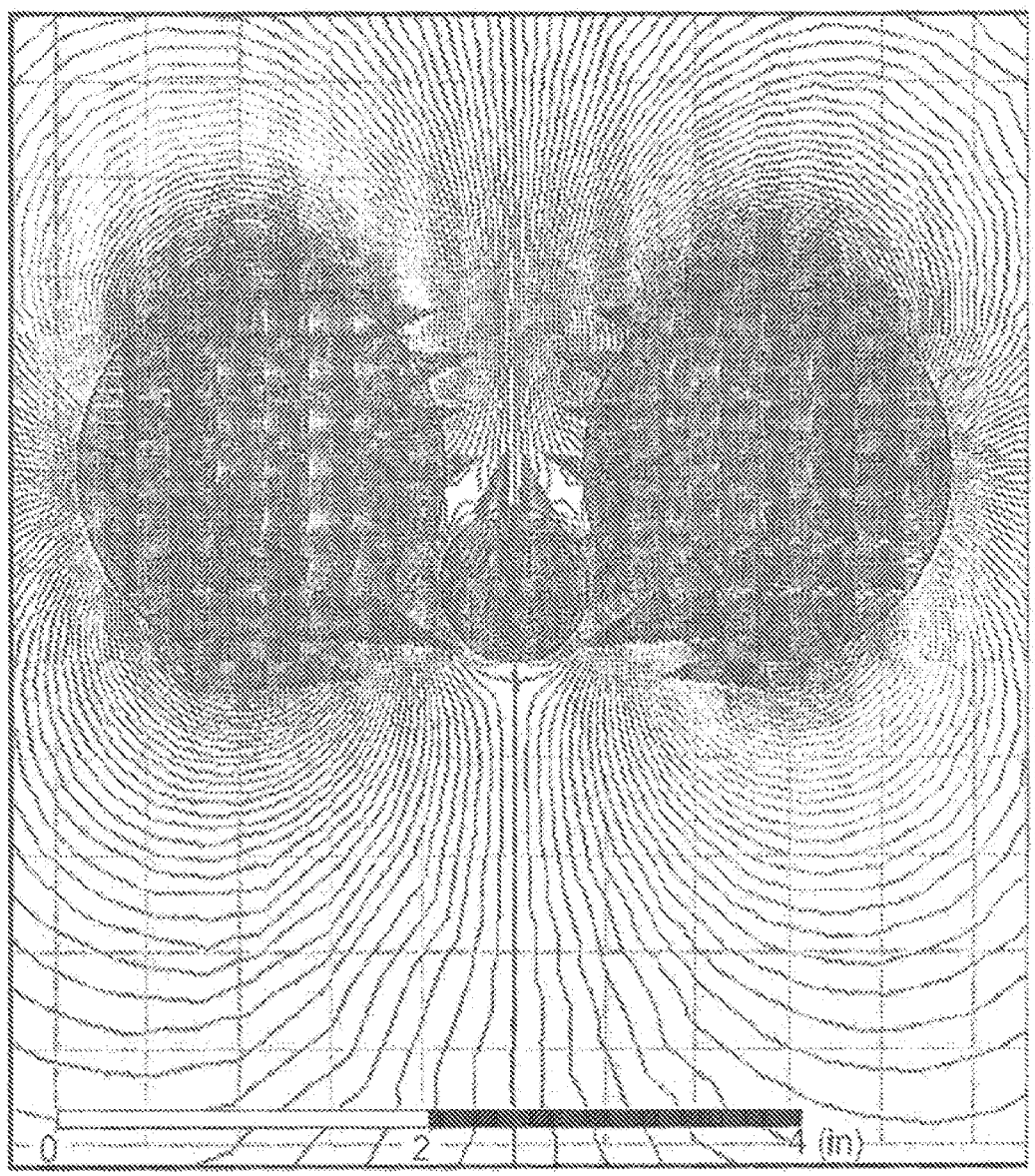

FIG. 28B illustrates a flux map of a three magnet system similar to that shown in FIG. 28A. The north poles of both larger magnets are, again, pointed toward the vertical line dividing the two magnets. Additionally, the north pole of the smaller third magnet is pointed downward, toward the implanted magnet. In this way, the magnetic flux density on the implanted magnet side of the three-magnet system may be increased. FIG. 28B illustrates an increased density of magnetic flux density lines. FIG. 28C, by contrast, illustrates the larger magnets in the same position, but the smaller magnet with the north pole pointed up, and away from the implanted magnet. In this configuration, the system decreases the flux density observed by the implanted magnet. Depending on the distances between magnets, magnet size, gap distance, etc.) this configuration can provide 50% less (decreased) magnetic flux density and therefore 50% less force than two magnet systems (such as that shown in FIG. 27.

The International Commission on Non-Ionizing Radiation Protection has issued "Guidelines for Limiting Exposure to Time-Varying Electric, Magnetic, and Electromagnetic Fields (Up To 300 GHz)" and "Guidelines on Limits of Exposure to Static Magnetic Fields." Both sets of guidelines are incorporated by reference in their entirety herein. These guidelines limit exposure to both time-varying magnetic fields and static magnetic fields to protect health. The limits are, however, different for different areas of the body. For example, a finger may have a higher limit than the brain. For time varying magnetic field limits, two variables are particularly important: field strength and field movement speed (e.g., with respect to the body). A weak magnetic field could generally be moved around the body relatively quickly while staying within the prescribed limits. By contrast, a very strong magnet would need to be move very slowly around the body to stay within the prescribed limits. This is one reason that patients undergoing MRI scans are told not to move—they are being subjected to incredibly strong magnetic fields. Much movement by a person in an MRI machine would likely exceed the prescribed limits. By contrast to time varying magnetic field limits, static field limits are concerned primarily with field strength. However, the guidelines note that they "do not apply to the exposure of patients undergoing medical diagnosis or treatment." If they did apply, it is almost certain that MRI machines would fall outside the limits.

In view of the guidelines discussed above, it can be seen that magnetic medical devices should ideally use the weakest magnetic field possible in the slowest manner possible to still achieve the desired clinical outcome. Several of the systems disclosed herein, including the external adjustment device 700 shown in FIG. 1, have many fixed parameters, including magnet sizes, intermagnet gaps, etc. For such an external adjustment device 700, there are not many ways to decrease the time-varying magnetic field exposure. Some might include increasing the gap distance (which may be difficult as stabilization against the patient is likely beneficial) and decreasing the rotation speed of the first external magnet 706 and the second external magnet 708.

Parameters that may be varied by a user in an external adjustment device 700 or by a "smart" external adjustment device 700 itself, include: intermagnet gap; gap distance; rotational offset (unilateral and bilateral); and magnet rotational velocity. Selectively varying one or more of these variable may allow the user or the "smart" external adjustment device 700 to optimize the system to have the lowest flux (weakest magnetic field) that is still clinically effective.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

The invention claimed is:

1. A system comprising:
    an implantable actuation device comprising a magnetic element configured to rotate in response to an external magnetic field; and
    a controller generating an external magnetic field and rotate the magnetic element of the implantable actuation device, the controller comprising:
        a first driver magnet defining a first rotational axis and a first central magnetic axis transverse to the first rotational axis, the first driver magnet having a first north pole at a first end of the first central magnetic axis and a first south pole at a second end of the first central magnetic axis;
        a second driver magnet defining a second rotational axis and a second central magnetic axis transverse to the second rotational axis, the second driver magnet having a second north pole at a second end of the second central magnetic axis and a second south pole at a second end of the second central magnetic axis, wherein at least one of the first and second central magnetic axes is oriented at a rotational offset relative to a flux reference point that is equidistant from the first driver magnet and the second driver magnet; and
        a drive system configured to generate synchronous rotation of the first and second driver magnets about the first and second rotational axes,
    wherein the controller is disposed sufficiently close to the distraction device that the magnetic element of the distraction device is affected by the external magnetic field.

2. The system of claim 1, wherein one or both of the first and second driver magnets comprises a permanent magnet.

3. The system of claim 1, wherein one or both of the first and second driver magnets comprises an electromagnet.

4. The system of claim 1, wherein the magnetic element comprises a permanent magnet.

5. The system of claim 1, wherein the controller further comprises a control circuit, a control device, a control unit, or a control mechanism for adjusting an angle between the first and second central magnetic axes.

6. The system of claim 1, wherein the first and second central magnetic axes are oriented at an angular offset relative to each other.

7. The system of claim 1, wherein the at least one of the first and second central magnetic axes is at a rotational offset of about 5° to about 135°.

8. The system of claim 1, wherein the controller comprises a third driver magnet.

9. The system of claim 8, wherein the third driver magnet is vertically offset from the first driver magnet and the second driver magnet.

10. The system of claim 8, wherein the third driver magnet includes a diameter that differs from a diameter of each of the first driver magnet and the second driver magnet.

11. The system of claim 8, wherein the first, second and third driver magnets are arranged in a Halbach array.

12. The system of claim 1, wherein the device comprises a first portion and a second portion, wherein the magnetic element is configured to move the second portion relative to the first portion in response to the external magnetic field.

13. The system of claim 1, wherein the magnetic element is configured to rotate in either of a first direction or a second direction corresponding to distraction or retraction of the device, respectively.

* * * * *